United States Patent
Aifantis et al.

(10) Patent No.: US 9,683,039 B2
(45) Date of Patent: Jun. 20, 2017

(54) NOTCH AGONISTS FOR THE TREATMENT OF CANCER

(71) Applicants: Iannis Aifantis, Brooklyn, NY (US); Camille Lobry, New York, NY (US)

(72) Inventors: Iannis Aifantis, Brooklyn, NY (US); Camille Lobry, New York, NY (US)

(73) Assignee: New York University, New York, NY (US)

(*) Notice: Subject to any disclaimer, the term of this patent is extended or adjusted under 35 U.S.C. 154(b) by 159 days.

(21) Appl. No.: 14/212,418

(22) Filed: Mar. 14, 2014

(65) Prior Publication Data

US 2014/0286955 A1 Sep. 25, 2014

Related U.S. Application Data

(60) Provisional application No. 61/782,025, filed on Mar. 14, 2013.

(51) Int. Cl.

| | |
|---|---|
| *A61K 38/16* | (2006.01) |
| *A61K 38/17* | (2006.01) |
| *A61K 38/18* | (2006.01) |
| *A61K 39/395* | (2006.01) |
| *C07K 16/28* | (2006.01) |
| *A61K 45/06* | (2006.01) |
| *C07K 14/475* | (2006.01) |

(Continued)

(52) U.S. Cl.
CPC ............ *C07K 16/28* (2013.01); *A61K 38/17* (2013.01); *A61K 39/3955* (2013.01); *A61K 45/06* (2013.01); *A61K 38/18* (2013.01); *A61K 38/19* (2013.01); *A61K 39/39558* (2013.01); *A61K 2039/505* (2013.01); *C07K 14/47* (2013.01); *C07K 14/705* (2013.01); *C07K 16/18* (2013.01); *C07K 16/22* (2013.01); *C07K 16/24* (2013.01); *C07K 16/30* (2013.01); *C07K 2317/73* (2013.01); *C07K 2317/75* (2013.01)

(58) Field of Classification Search
CPC ........ C07K 16/00; C07K 16/18; C07K 16/22; C07K 16/24; C07K 16/28; C07K 16/30; C07K 14/47; C07K 14/475; C07K 14/52; C07K 14/705; A61K 2300/00; A61K 2039/505; A61K 38/00; A61K 38/19; A61K 38/17; A61K 39/395; A61K 39/3955; A61K 39/39558

See application file for complete search history.

(56) References Cited

U.S. PATENT DOCUMENTS

| | | |
|---|---|---|
| 6,689,744 B2 | 2/2004 | Gao et al. |
| 7,915,390 B2 * | 3/2011 | Li .................... C07K 16/00 530/350 |

(Continued)

OTHER PUBLICATIONS

Chadwick et al. Notch induces cell cycle arrest and apoptosis in human erythroleukaemic TF-1 cells. Blood Cells, Molecules, and Diseases 41(3): 270-277, 2008.*

(Continued)

*Primary Examiner* — Bridget E Bunner
(74) *Attorney, Agent, or Firm* — LeCLairRyan, a Professional Corporation

(57) ABSTRACT

The present invention is directed to methods of treating and preventing acute myeloid leukemia and acute myeloid leukemia relapse disease in a subject that involve administering a Notch receptor agonist.

21 Claims, 24 Drawing Sheets

(51) Int. Cl.
| | |
|---|---|
| C07K 14/52 | (2006.01) |
| C07K 14/435 | (2006.01) |
| C07K 14/705 | (2006.01) |
| C07K 16/18 | (2006.01) |
| A61K 39/00 | (2006.01) |
| A61K 38/19 | (2006.01) |
| C07K 16/30 | (2006.01) |
| C07K 16/24 | (2006.01) |
| C07K 16/22 | (2006.01) |
| C07K 14/47 | (2006.01) |

(56) References Cited

U.S. PATENT DOCUMENTS

| | | | |
|---|---|---|---|
| 2013/0089562 A1* | 4/2013 | French | C07K 16/28 424/172.1 |
| 2014/0127211 A1* | 5/2014 | Geles | A61K 47/48569 424/138.1 |

OTHER PUBLICATIONS

Conboy et al. Notch-mediated restoration of regenerative potential to aged muscle. Science 302: 1575-1577, 2003 (plus supplemental materials).*

Haraguchi et al. Notch activation induces the generation of functional NK cells from human cord blood CD34-positive cell devoid of IL-15. J Immunol 182: 6168-6178, 2009.*

Kannan et al. Notch activation inhibits AML growth and survival: a potential therapeutic approach. J Exp Med 210(2): 321-327, 2013.*

Kijima et al. Dendritic cell-mediated NK cell activation is controlled by Jagged2-Notch interaction. Proc Natl Acad Sci USA 105(19): 7010-7015, 2008.*

Lee et al. Molecular cloning of agonistic and antagonistic monoclonal antibodies against human 4-1 BB. Eur J Immunogenet 29: 449-452, 2002.*

Li et al. Modulation of Notch signaling by antibodies specific for the extracellular negative regulatory region of Notch3. J Biol Chem 283(12): 8046-8054, 2008.*

Lobry et al. Notch pathway inhibition activation targets AML-initiating cell homeostasis and differentiation. J Exp Med 210(2): 301-319, 2013.*

Lobry et al. Notch signaling: switching an oncogene to a tumor suppressor. Blood 123(16): 2451-2459, 2014.*

Richter et al. Antagonistic TNF receptor one-specific antibody (ATROSAB): receptor binding and in vitro bioactivity. PLOS One 8(8): e72156, 2013.*

Rimm et al. J Cell Biol 111(No. 6 Pt 1): 2405-2416, 1990.*

Shipley et al. Acute myelogenous leukemia. Exp Hematol 37: 649-658, 2009.*

Sutphin et al. Notch agonists: Emerging as a feasible therapeutic. Blood 108(11): 412A, 2006.*

Chen et al., "Down-Regulation of Notch-1 Expression Decreases PU.1-Mediated Myeloid Differentiation Signaling in Acute Myeloid Leukemia," Int. J. Oncol. 32:1335-1341 (2008).

Chiaramonte et al., "A Wide Role for Notch1 Signaling in Acute Leukemia," Cancer Lett. 219(1):113-20 (2005).

Ersvaer et al., "Future Perspectives: Therapeutic Targeting of Notch Signalling May Become a Strategy in Patients Receiving Stem Cell Transplantation of Hematologic Malignancies," Bone Marrow Res. 2011:570796 (15 pages) (2011).

Ferrara & Musto, "Hypomethylating Agents for the Treatment of Acute Myeloid Leukemia in the Elderly: For All, None, or Which Patients?" Cancer 117(17):3879-81 (2011).

Fu et al., "Transition of Cleaved Notch1 and Gene Expression Changes in Myeloblastic Leukemia Cells Stimulated with Notch Ligands," Anticancer Res. 29:3967-3970 (2009).

Kawaguchi-Ihara et al., "Promotion of the Self-Renewal Capacity of Human Acute Leukemia Cells by Wnt3A," Anticancer Res. 28:2701-2704 (2008).

Lam & Adams, "Blocking HIF1Alpha Activity Eliminates Hematological Cancer Stem Cells," Cell Stem Cell 8:354-356 (2011).

Li et al., "Notch Signaling Maintains Proliferation and Survival of the HL60 Human Promyelocytic Leukemia Cell Line and Promotes the Phosphorylation of the Rb Protein," Mol. Cell. Biochem. 340(1-2):7-14 (2010).

Lobry et al., "Oncogenic and Tumor Suppressor Functions of Notch in Cancer. It's Notch What You Think," J. Exp. Med. 208(10):1931-1935 (2011).

Miyazato et al., "Identification of Myelodysplastic Syndrome-Specific Genes by DNA Microarray Analysis With Purified Hematopoietic Stem Cell Fraction," Blood 98(2):422-427 (2001).

Murata-Ohsawa et al., "Cellular Analysis of Growth Suppression Induced by the Notch Ligands, Delta-1 and Jagged-1 in Two Myeloid Leukemia Cell Lines," Int. J. Mol. Med. 14(2):223-6 (2004).

Roboz, "Novel Approaches to the Treatment of Acute Myeloid Leukemia," Hematology Am. Soc. Hematol. Educ. Program 2011:43-50 (2011).

Schwarz et al., "The Deacetylase Inhibitor LAQ824 Induces Notch Signalling in Haematopoietic Progenitor Cells," Leuk. Res. 35(1):119-25 (2011).

Stankiewicz & Crispin, "AKT Collaborates with ERG and Gata1s to Dysregulate Megakaryopoiesis and Promote AMKL," Leukemia 27(6)1339-1347 (2013).

Sugimoto et al., "Notch2 Signaling Is Required for Potent Antitumor Immunity In Vivo," J. Immunol. 184:4673-4678 (2010).

Tohda & Nara, "Expression of Notch1 and Jagged1 Proteins in Acute Myeloid Leukemia Cells," Leuk. Lymphoma 42 (3):467-72 (2001).

Tohda et al., "Notch Ligands, Delta-1 and Delta-4 Suppress the Self-Renewal Capacity and Long-Term Growth of Two Myeloblastic Leukemia Cell Lines," Int. J. Oncol. 22(5):1073-9 (2003).

Tohda et al., "Diverse Effects of the Notch Ligands Jagged1 and Delta1 on the Growth and Differentiation of Primary Acute Myeloblastic Leukemia Cells," Exp. Hematol. 33:558-563 (2005).

Wang et al., "Overexpression of Human CAP10-Like Protein 46 KD in T-Acute Lymphoblastic Leukemia and Acute Myelogenous Leukemia," Genet. Test. Mol. Biomarkers 14(1):127-33 (2010).

Wang et al., "Targeting HIF1Alpha Eliminates Cancer Stem Cells in Hematological Malignancies," Cell Stem Cell 8 (4):399-411 (2011).

Zhang et al., "Cross-Talk Between Leukemic and Endothelial Cells Promotes Angiogenesis by VEGF Activation of the Notch/Dll4 Pathway," Carcinogenesis 34(3):667-677 (2013).

Zhang et al., "Prognostic Impact of Delta-Like Ligand 4 and Notch1 in Acute Myeloid Leukemia," Oncol. Reports 28:1503-1511 (2012).

Zweidler-McKay et al., "Notch Signaling Is a Potent Inducer of Growth Arrest and Apoptosis in a Wide Range of B-Cell Malignancies," Blood 106(12):3898-3906 (2005).

* cited by examiner

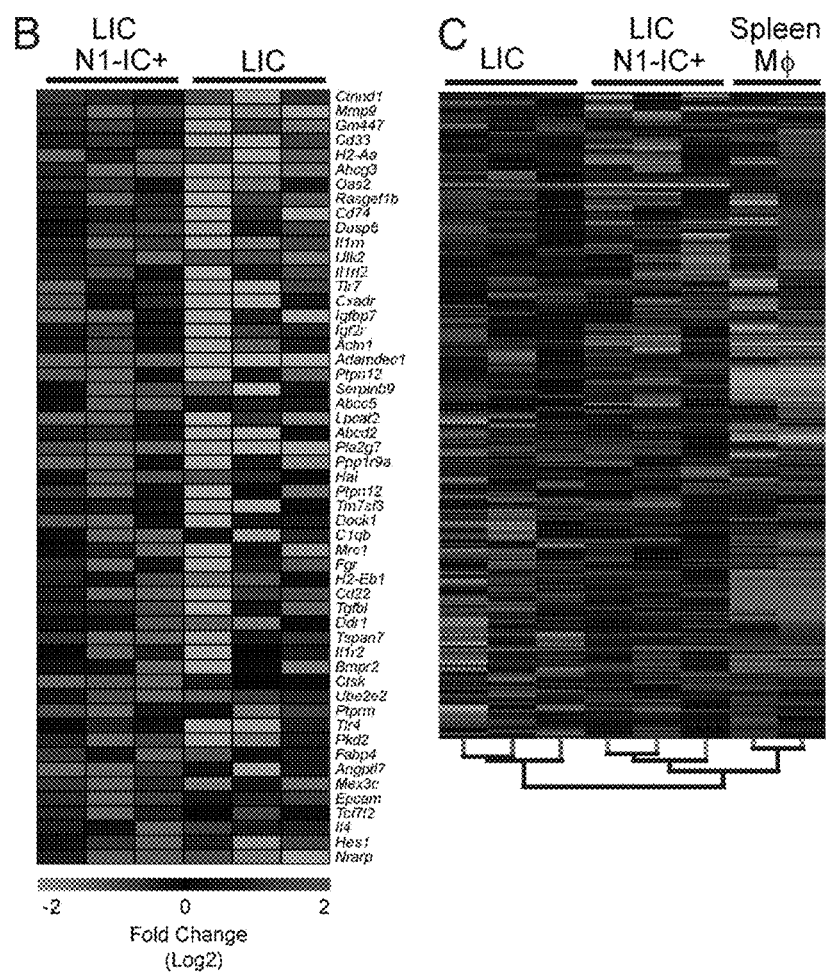
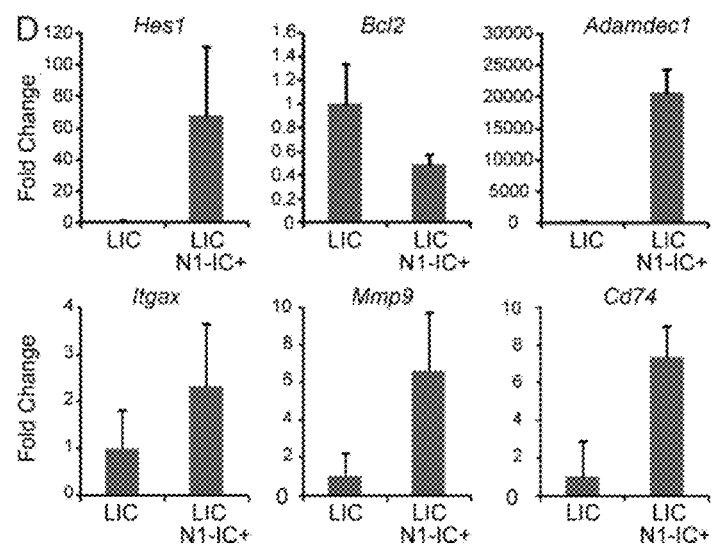
Figures 5B–5D

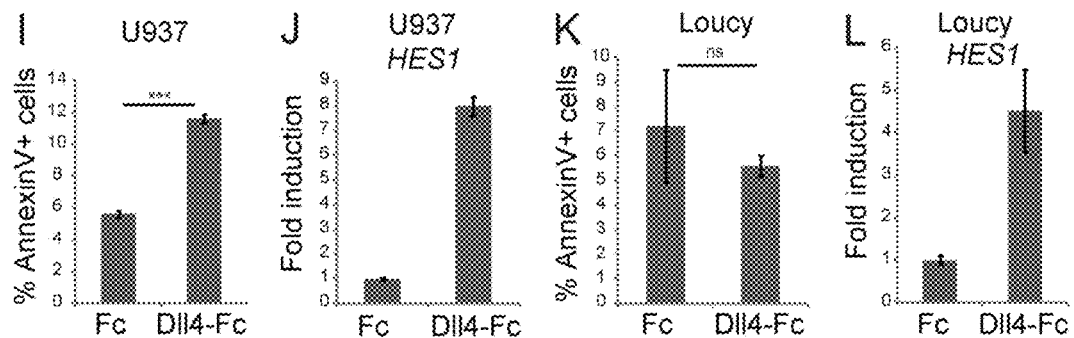
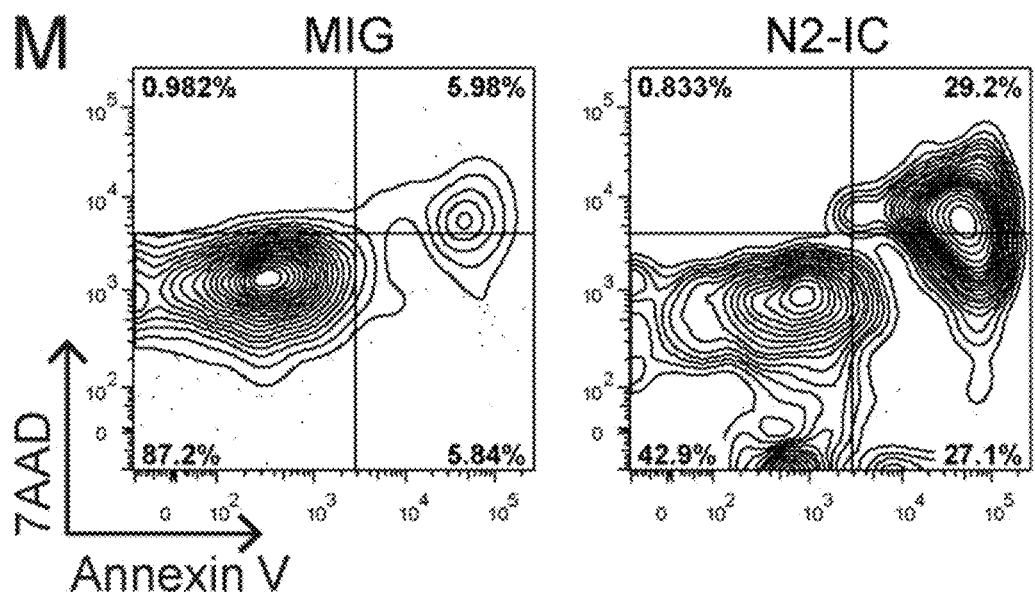
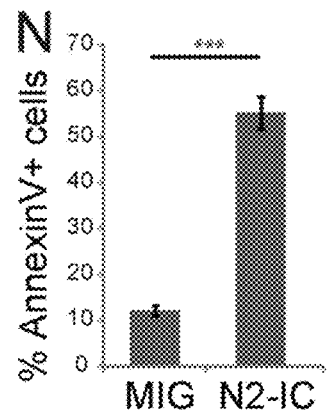
Figures 7I–7N

NOTCH AGONISTS FOR THE TREATMENT OF CANCER

This application claims the benefit of U.S. Provisional Patent Application Ser. No. 61/782,025, filed Mar. 14, 2013, which is hereby incorporated by reference in its entirety.

This invention was made with government support under grant number 5R01CA105129 awarded by the National Institutes of Health. The government has certain rights in this invention.

FIELD OF THE INVENTION

The present invention is directed to methods of treating and preventing malignancies by inducing Notch receptor signaling.

BACKGROUND OF THE INVENTION

Notch signaling is a highly evolutionarily conserved pathway implicated in diverse functions including stem cell maintenance, cell fate specification, cell proliferation, and apoptosis. When membrane-bound Notch receptors recognize ligands of the Delta and Jagged families, they are cleaved by metalloproteases and the γ-secretase complex, allowing the release of the intracellular domain into the nucleus where it associates with co-factors to control a significant number of targets including the Hes family of genes (Artavanis-Tsakonas et al., "Notch Signaling: Cell Fate Control and Signal Integration in Development," *Science* 284:770-776 (1999); Ilagan and Kopan, "SnapShot: Notch Signaling Pathway," *Cell* 128:1246 (2007)). In the hematopoietic system, Notch is essential for the emergence of definitive hematopoietic stem cells (HSC) during fetal life (Robert-Moreno et al., "Impaired Embryonic Haematopoiesis Yet Normal Arterial Development in the Absence of the Notch Ligand Jagged1," *Embo J.* 27:1886-1895 (2008)) and indispensable for the commitment of progenitors to the T cell lineage (Zuniga-Pflucker, J. C. "T-cell Development Made Simple," *Nat. Rev. Immunol.* 4:67-72 (2004)). Moreover, Notch1 appears to be the central oncogenic trigger in T cell acute lymphoblastic leukemia (T-ALL) in both humans and mice (Weng et al., "Activating Mutations of NOTCH1 in Human T Cell Acute Lymphoblastic Leukemia," *Science* 306:269-271 (2004)). Indeed, Notch1 (or its regulator Fbw7) are commonly mutated leading to constitutive activation of the Notch pathway in the majority of T-ALL patients (Malyukova et al., "The Tumor Suppressor Gene hCDC4 is Frequently Mutated in Human T-Cell Acute Lymphoblastic Leukemia With Functional Consequences for Notch Signaling," *Cancer Res.* 67:5611-5616 (2007); Maser et al., "Chromosomally Unstable Mouse Tumours Have Genomic Alterations Similar to Diverse Human Cancers," *Nature* 447:966-971 (2007); Thompson et al., "The SCFFBW7 Ubiquitin Ligase Complex as a Tumor Suppressor in T Cell Leukemia," *J. Exp. Med.* 204:1825-1835 (2007)). In contrast to the T cell lineage where the role of Notch signaling is well defined, there is conflicting information on the role of Notch signaling in the function of adult stem cells (HSC), multipotential progenitors (MPP) and in the myelo-erythroid compartment (Dahlberg et al., "Ex vivo Expansion of Human Hematopoietic Stem and Progenitor Cells," *Blood* 117:6083-6090 (2011); Delaney et al., "Notch-Mediated Expansion of Human Cord Blood Progenitor Cells Capable of Rapid Myeloid Reconstitution," *Nat. Med.* 16:232-236 (2010); Maillard et al., "Canonical Notch Signaling is Dispensable for the Maintenance of Adult Hematopoietic Stem Cells," *Cell Stem Cell* 2:356-366 (2008)). Initial in vitro reports suggested that Notch signaling accelerates myeloid differentiation (Schroeder et al., "Notch Signaling Induces Multilineage Myeloid Differentiation and Up-Regulates PU.1 Expression," *J. Immunol.* 170:5538-5548 (2003); Tan-Pertel et al., "Notch Signaling Enhances Survival and Alters Differentiation of 32D Myeloblasts," *J. Immunol.* 165:4428-4436 (2000)). However, subsequent studies contested this conclusion. Most notably, it was shown that Notch can suppress myelopoiesis in vitro (de Pooter et al., "Notch Signaling Requires GATA-2 to Inhibit Myelopoiesis From Embryonic Stem Cells and Primary Hemopoietic Progenitors," *J. Immunol.* 176:5267-5275 (2006)), and Gilliland and colleagues reported that Notch signaling can induce megakaryocyte differentiation (Mercher et al., "Notch Signaling Specifies Megakaryocyte Development From Hematopoietic Stem Cells," *Cell Stem Cell* 3:314-326 (2008)). It has recently been shown that Notch signaling can function as an antagonist of the granulomonocytic progenitor (GMP) cell fate and that loss of Notch signaling biases commitment towards GMP differentiation, eventually resulting in chronic myelomonocytic leukemia (CMML) (Klinakis et al., "A Novel Tumour-Suppressor Function for the Notch Pathway in Myeloid Leukaemia," *Nature* 473:230-233 (2011)), a myelodysplastic/myeloproliferative overlap syndrome. Inactivating mutations in the Notch pathway were also observed in a fraction of CMML patients, suggesting that this pathway is targeted by genetic alterations. These data are consistent with subsequent reports of inactivating Notch pathway mutations in head and neck cancer (Agrawal et al., "Exome Sequencing of Head and Neck Squamous Cell Carcinoma Reveals Inactivating Mutations in NOTCH1," *Science* 333:1154-1157 (2011); Stransky et al., "The Mutational Landscape of Head and Neck Squamous Cell Carcinoma," *Science* 333:1157-1160 (2011)). However, none of these studies were able to prove that Notch could function as a tumor suppressor in vivo. For example the data was not able to prove direct involvement of Notch signaling in myeloid disease, as Notch deletion did not lead to transplantable frank myeloid leukemia. These studies also did not test whether Notch pathway activation can target established disease, something of unique clinical significance.

Acute Myeloid Leukemia (AML) is a clonal hematopoietic neoplasm characterized by the proliferation and accumulation of myeloid progenitor cells in bone marrow, and is the most common acute leukemia diagnosed in adults. Outcomes for AML patients remain poor, despite the use of cytotoxic chemotherapy and stem cell transplantation most patients die of relapsed, refractory AML (Frohling et al., "Genetics of Myeloid Malignancies: Pathogenetic and Clinical Implications," *J. Clin. Oncol.* 23:6285-6295 (2005)). Cytogenetic and molecular studies have shown that AML is a heterogeneous disease in which a variety of cytogenetic and molecular alterations have biologic and clinical relevance (Armstrong et al., "MLL-Rearranged Leukemias: Insights From Gene Expression Profiling," *Semin. Hematol.* 40:268-273 (2003); Dash and Gilliland, "Molecular Genetics of Acute Myeloid Leukaemia," *Best Pract. Res. Clin. Haematol.* 14:49-64 (2001); Dohner et al., "Diagnosis and Management of Acute Myeloid Leukemia in Adults: Recommendations From an International Expert Panel, on Behalf of the European LeukemiaNet," *Blood* 115:453-474 (2010)). These include chromosomal abnormalities, which lead to generation of leukemogenic fusion oncoproteins, including Mixed Lineage Leukemia (MLL) gene fusions which are associated with adverse outcome. In addition, somatic mutations in tumor suppressors have been shown to contribute to leukemogenesis and improve AML risk classification (Bacher et al., "Molecular Genetics in Acute Myeloid Leukemia," Curr. Opin. Oncol. 22:646-655 (2010)). However, molecular mechanisms linking these mutations to transformation are incompletely understood, and the role of the most recently identified genes, including TET2, ASXL1 and IDH1/2 in AML pathogenesis has not been fully delineated. Current treatments for AML patients include dose-intensive chemotherapy and stem cell transplantation, which are associated with significant toxicities and high relapse rates. Thus, identification of new signaling pathways of which activation or inhibition will lead to therapeutic targeting of AML cells is of urgent clinical significance

SUMMARY OF THE INVENTION

A first aspect of the present invention is directed to a method of inducing cell differentiation and cell death in a population of acute myeloid leukemia leukemia-initiating cells (LICs). This method involves administering a Notch receptor agonist to the population of acute myeloid leukemia LICs under conditions effective to induce cell differentiation and cell death in the population of acute myeloid leukemia LICs.

Another aspect of the present invention is directed to a method of treating acute myeloid leukemia in a subject. This method involves selecting a subject having acute myeloid leukemia and administering to the selected subject, a Notch receptor agonist under conditions effective to treat the acute myeloid leukemia in the subject.

Another aspect of the present invention is directed to a method of inhibiting the development of acute myeloid leukemia relapse disease in a subject. This method involves selecting a subject having had acute myeloid leukemia and administering, to the selected subject, a Notch receptor agonist under conditions effective to inhibit the development of acute myeloid leukemia relapse disease in the subject.

As described herein, applicants have analyzed Notch pathway activation status in cytogenetically normal AML patient samples, and demonstrated that Notch signaling is silenced in the majority of AML patients. Re-activation of the Notch signaling pathway both in vivo, using conditional inducible alleles of the active form of NOTCH1 or NOTCH2 as well as in vitro, using recombinant ligand-mediated activation induced rapid cell cycle arrest, aberrant differentiation and rapid apoptosis of AML cells. Furthermore, genetic inactivation of Notch signaling combined with deletion of the frequently mutated in AML TET2 gene (Abdel-Wahab et al., "Genetic Characterization of TET1, TET2, and TET3 Alterations in Myeloid Malignancies," Blood 114:144-147 (2009); Delhommeau et al., "Mutation in TET2 in Myeloid Cancers," N. Engl. J. Med. 360:2289-2301 (2009), which are hereby incorporated by reference in their entirety) collaborated to induce AML-like disease in vivo, strongly suggesting that Notch signaling inhibition is able to promote AML. The data presented herein demonstrates that Notch signaling acts as a tumor suppressor in AML and advocates the therapeutic use of Notch agonists to induce Notch re-activation to treat this type of leukemia as well as other malignancies where Notch signaling is tumor suppressive.

BRIEF DESCRIPTION OF THE DRAWINGS

FIG. 1A is a heatmap showing relative expression levels of Notch signaling pathway target genes in 187 AML and normal $Lin^{neg}CD34^+CD38^-$ bone marrow cells. FIG. 1B is a bar graph representing expression value of Notch receptors NOTCH1 and NOTCH2 in the same samples. Expression is normalized to GAPDH expression. FIG. 1C is a heatmap showing relative expression levels of Notch signaling pathway target genes in $Lin^{neg}CD34^+CD38^-$ and $Lin^{neg}CD34^+CD38^+$ populations from 12 AML patients compared to normal $Lin^{neg}CD34^+CD38^-$ bone marrow cells. FIG. 1D shows the results of quantitative RT-PCR analysis for HES1 gene in CD34+ cord blood stem cells and 4 AML patient samples (left panel) and Chromatin immuno-precipitation of H3K27me3 on the promoter of the same samples (right panel). FIG. 1E shows the results of a quantitative RT-PCR analysis for NRARP gene expression in CD34+ cord blood stem cells and 4 AML patient samples (left panel) and Chromatin immuno-precipitation of H3K27me3 on the promoter of the same samples (right panel). FIG. 1F shows the results of quantitative RT-PCR analysis for HES1 gene in THP1 and DND41 cell lines (left panel) and Chromatin immuno-precipitation of H3K27me3 on the promoter of HES1 gene in THP1 and DND41 cell lines (right panel). ***=p-value<0.001

FIG. 2A is a heatmap showing relative expression levels of Notch signaling pathway target genes and Notch receptors in LSK, murine MLL-AF9-induced AML leukemia initiating cells (LIC) and murine NOTCH1-IC driven T-ALL cells. FIG. 2B is a bar graph showing raw expression values of Notch1-4 receptors from different biological replicates of normal murine LSK population, murine AML LIC and T-ALL. FIG. 2C shows the results of FACS analysis using antibodies specific for extracellular domains of Notch1 and Notch2. The black line represents Ig control staining, blue line represents Notch1 antibody and red line represents Notch2 antibody. FIG. 2D shows ChIP-seq analysis of H3K4me3 and H3K27me3 on promoter and gene body of Notch target genes Hes1, Nrarp and Gata3 in LSK and AML LIC. FIG. 2E depicts the raw expression values of Hes1, Nrarp and Gata3 in LSK and AML LIC. Data represent mean±SD of 3 biological replicates.

FIG. 3A shows peripheral white blood cell counts before and 6 days after tamoxifen treatment of and $Rosa^{wt/CreERT2}$ and $EF1\alpha^{wt/lsl-N1-IC} Rosa^{wt/CreERT2}$ mice. FIG. 3B shows representative H&E stained liver sections from $Rosa^{wt/CreERT2}$ and $EF1\alpha^{wt/lsl-N1-IC} Rosa^{wt/CreERT2}$ mice sacrificed 6 days after tamoxifen treatment (upper panel) and Representative TUNEL staining on spleen sections from $Rosa^{wt/CreERT2}$ and $EF1\alpha^{wt/lsl-N1-IC} Rosa^{wt/CreERT2}$ mice sacrificed 6 days after tamoxifen treatment (lower panel). Scale bars=200 µm. FIG. 3C is a graph showing weight in grams of spleens from $Rosa^{wt/CreERT2}$ and $EF1\alpha^{wt/lsl-N1-IC} Rosa^{wt/CreERT2}$ mice sacrificed 6 days after tamoxifen treatment (*=p-value<0.05). FIG. 3D shows a representative FACS analysis (gated on $Lin^{neg}/Sca1^-$ cells) and FIG. 3E is a bar graph showing absolute number of bone marrow AML LICs. FIG. 3F is a Kaplan-Meier survival analysis of secondary recipients transplanted with 5000 non-treated LICs from $Rosa^{wt/CreERT2}$ and $EF1\alpha^{wt/lsl-N1-IC}$ mice. Tamoxifen is injected once 21 days after transplantation. Each cohort is constituted of 7 mice. FIG. 3G is a graph showing the percentage of YFP+ peripheral white blood cells and FIG. 3H is a graph showing total white blood cell counts before and after Tamoxifen treatment of $Rosa^{wt/CreERT2}$ and Rosa$^{lsl-N2-IC/CreERT2}$ mice. FIG. 3I is a graph showing the percentage of YFP+ peripheral white blood cells, and FIG. 3J is a graph showing total white blood cell counts of secondary recipients transplanted with 10000 LICs isolated from Rosa$^{wt/CreERT2}$ and Rosa$^{lsl-N2-IC/CreERT2}$ mice 3 weeks after transplantation. FIG. 3K is a Kaplan-Meier survival analysis of secondary recipients transplanted with 10000 LICs isolated from Rosa$^{wt/CreERT2}$ and Rosa$^{lsl-N2-IC/CreERT2}$ mice. FIG. 3L shows relative proportion of CD4/CD8 double positive (DP) T cells in peripheral blood of mice transplanted with total bone marrow from Rosa$^{lsl-N1-IC/wt}$ UbcCreER (N1-IC), Rosa$^{lsl-N2-IC/wt}$ UbcCreERT2 (N2-IC) and UbcCreER (Ctrl) at the indicated time periods after tamoxifen injection of the recipient mice. FIG. 3M is a Kaplan-Meier survival analysis of mice transplanted with total bone marrow from Rosa$^{lsl-N1-IC/wt}$ UbcCreER (N1-IC), Rosa$^{lsl-N2-IC/wt}$ UbcCreERT2 (N2-IC) and UbcCreER (Ctrl). N=5 in each cohort).

FIG. 4A shows colony morphology in methylcellulose culture and Wright-Giemsa staining of cytospin of LIC from Rosa$^{wt/CreERT2}$ and EF1α$^{wt/lsl-N1-IC}$ mice treated with DMSO or with 4-hydroxy-tamoxifen (4OHT). FIG. 4B is a bar graph showing total colony count of LIC from Rosa$^{wt/CreERT2}$ and EF1α$^{wt/lsl-N1-IC}$ mice treated with DMSO or with 4-hydroxy-tamoxifen (4OHT), 8 days after methylcellulose culture initiation. FIG. 4C shows Annexin V staining of LIC from Rosa$^{wt/CreERT2}$ and EF1α$^{wt/lsl-N1-IC}$ mice treated with DMSO or with 4-hydroxy-tamoxifen (4OHT), 8 days after methylcellulose culture initiation. FIG. 4D shows colony morphology in methylcellulose culture and Wright-Giemsa staining of cytospin of MLL-AF9 or AML1-ETO (EA9a) transformed HSPC from Rosa$^{lsl-N2-IC/CreERT2}$ mice treated with DMSO or with 4-hydroxy-tamoxifen (4OHT). FIG. 4E shows total colony count of MLL-AF9 or AML1-ETO (EA9a) transformed HSPC from Rosa$^{wt/CreERT2}$ and Rosa$^{lsl-N2-IC/CreERT2}$ mice treated with DMSO or with 4-hydroxy-tamoxifen (4OHT), 8 days after methylcellulose culture initiation.

FIGS. 5A-5D demonstrate that Notch activation induces differentiation associated genes in AML LIC in vivo. FIG. 5A shows the GeneSet Enrichment Analysis for the indicated genesets of LIC N1-IC+ versus LIC. FIG. 5B is a heatmap representing the top significantly upregulated genes in LIC N1-IC+ compared to LIC. FIG. 5C shows a hierarchical clustering of LIC, LIC expressing NOTCH1-IC (LIC N1-IC+) and spleen macrophages. FIG. 5D shows the results of quantitative RT-PCR expression analysis of the indicated genes on LIC and LIC N1-IC+. Data represent mean±SD of 3 biological replicates.

FIG. 6A shows a representative Wright-Giemsa stained cytospins of LIC treated with Fc control (left) or Dll4-Fc (right). Scale bar=50 μm FIG. 6B depicts representative FACS staining for apoptosis of LIC treated with Fc control or Dll4-Fc using AnnexinV/7AAD FACS staining after 24 h of treatment. FIG. 6C shows quantification of the proportion of apoptotic cells upon Fc or Dll4-Fc treatment (data represent mean±SD of 3 independent experiments). FIG. 6D shows the results of quantitative RT-PCR expression analysis of indicated genes in LIC cultured on Dll4-Fc or control Fc for 24 h. (Data represent mean±SD of 3 biological replicates). FIG. 6E shows chromatin immuno-precipitation of H3K27me3 on the promoter of HES1 gene in LIC cultured on Dll4-Fc or control Fc for 24 h (Data represent mean±SD of 2 biological replicates). FIG. 6F shows representative FACS staining for CD11c of LIC treated with Fc control or Dll4-Fc. FIG. 6G is a bar graph showing the mean fluorescence intensity quantification of CD11c staining (Data represent mean±SD of 3 biological replicates). FIG. 6H depicts an analysis of apoptosis in LIC co-cultured with OP9-MIG or OP9-Dll4 using AnnexinV/7AAD FACS staining after 48 h of culture. ***=p-value<0.001.

FIGS. 7A-7P show that recombinant Dll4-Fc ligand mediated Notch activation induces differentiation and apoptosis of AML cells. FIG. 7A is a FACS analysis of THP1 using antibodies specific for extracellular domains of Notch1 and Notch2. The grey line represents Ig control staining, blue line represents Notch1 antibody and red line represents Notch2 antibody staining. FIG. 7B shows representative Wright-Giemsa stained cytospins of THP1 cells treated with Fc control or Dll4-Fc for 48 h. Scale bar=50 μm. FIG. 7C shows the result of quantitative RT-PCR expression analysis of Notch1-4 receptors in THP1 cells. (Data represent mean±SD of 3 biological replicates). FIG. 7D is a bar graph quantifying the proportion of apoptotic THP1 cells by AnnexinV staining upon Fc or Dll4-Fc treatment (data represent mean±SD of 3 independent experiments). FIG. 7E is a graph showing quantitative RT-PCR expression analysis of indicated genes in THP1 cultured on Dll4-Fc or control Fc for 48 h. (Data represent mean±SD of 3 biological replicates). FIG. 7F shows chromatin immuno-precipitation of H3K27me3 on the promoter of HES1 and NRARP genes in THP1 cells cultured on Dll4-Fc or control Fc for 24 h (Data represent mean±SD of 2 biological replicates). FIG. 7G shows a FACS analysis of U937 cells using antibodies specific for extracellular domains of Notch1 and Notch2. The grey line represents Ig control staining, blue line represents Notch1 antibody, and red line represents Notch2 antibody staining. FIG. 7H shows a representative Wright-Giemsa stained cytospins of U937 cells treated with Fc control or Dll4-Fc for 48 h. Scale bar=50 μm. FIG. 7I is a bar graph quantifying the proportion of apoptotic U937 cells by AnnexinV staining upon Fc or Dll4-Fc treatment (data represent mean±SD of 3 independent experiments). FIG. 7J is a graph showing quantitative RT-PCR analysis of HES1 gene expression in U937 cells cultured on Dll4-Fc or control Fc for 48 h. (Data represent mean±SD of 3 biological replicates). FIG. 7K is a bar graph quantifying the proportion of apoptotic Loucy cells by AnnexinV staining upon Fc or Dll4-Fc treatment (data represent mean±SD of 3 independent experiments). FIG. 7L is a bar graph showing HES1 gene expression in Loucy cells cultured on Dll4-Fc or control Fc for 48 h quantified by RT-PCR analysis (Data represent mean±SD of 3 biological replicates). FIG. 7M shows a representative apoptosis analysis of THP1, using AnnexinV/7AAD FACS staining 6 days after infection with pMIG or pMIG-NOTCH2-IC. FIG. 7N is a graph quantifying the proportion of apoptotic THP1 cells 6 days after infection with pMIG or pMIG-NOTCH2-IC (N2-IC). FIG. 7O shows a representative cell cycle analysis of THP1 using Ki67 and DAPI FACS staining and FIG. 7P is a graph quantification of proportion of cells in each cell cycle phase 6 days after infection with pMIG or pMIG-NOTCH2-IC (N2-IC). (Data represent mean±SD of 3 biological replicates). ***=p-value<0.001.

FIG. 8A is a heatmap representing the top significantly upregulated genes in THP1 treated with Dll4-Fc compared to vehicle treated THP1 for 48 h. FIG. 8B shows the GeneSet Enrichment Analysis for the indicated gene sets of THP1 treated with Dll4-Fc versus THP1 treated with control vehicle. FIG. 8C is a bar graph showing quantitative RT-PCR expression analysis of the indicated genes in vehicle and Dll4-Fc treated THP1. Data represent mean±SD of 3 biological replicates. FIG. 8D shows the proportion of apoptotic cells revealed by AnnexinV staining of AML patient samples treated with control vehicle or Dll4-Fc for 24 h. Data represent mean±SD of 3 replicates. FIG. 8E shows representative bright field pictures of AML patient #6 cells treated with vehicle or Dll4-Fc for 24 h. Scale bar=100 μm. FIG. 8F shows FACS analyses using antibodies specific for extracellular domain of Notch2. Grey line represents Ig control staining and red line represents Notch2 antibody staining. FIG. 8G is a series of bar graphs showing HES1 gene expression in cells of four AML patients cultured on Dll4-Fc or control Fc for 24 h and assessed by a quantitative RT-PCR. (Data represent mean±SD of 3 biological replicates)

FIG. 9A is a representative FACS analysis of myeloid cells from peripheral blood of WT, $Ncstn^{-/-}$ and $Ncstn^{-/-}Tet2^{-/-}$ littermates 7 weeks after birth. FIG. 9B shows the peripheral white blood cell counts of WT, $Tet2^{-/-}$, $Ncstn^{-/-}$ and $Ncstn^{-/-}Tet2^{-/-}$ mice 7 weeks after birth. Data represent mean±SD of 5 different mice per cohort. FIG. 9C shows a representative Wright-Giemsa stained blood smear of $Ncstn^{-/-}Tet2^{-/-}$ mouse 7 weeks after birth. Scale bar=50 μm. FIG. 9D is a representative spleen picture of WT, $Ncstn^{-/-}$ and $Ncstn^{-/-}Tet2^{-/-}$ littermates 7 weeks after birth. FIG. 9E shows a representative FACS analysis of myeloid cells from bone marrow and spleen of WT, $Ncstn^{-/-}$ and $Ncstn^{-/-}Tet2^{-/-}$ littermates 7 weeks after birth. FIG. 9F shows H&E staining of liver sections of WT, $Ncstn^{-/-}$ and $Ncstn^{-/-}Tet2^{-/-}$ littermates 7 weeks after birth. Scale bar=200 μm. FIG. 9G shows representative FACS analysis of bone marrow myeloid progenitors (Lineage$^-$/Sca1$^-$/cKit$^+$) showing CMP (CD34$^+$, FcγRII/III$^{lo}$), MEP (CD34$^-$/FcγRII/III$^-$) and GMP (CD34$^+$/FcγRII/III$^+$) of WT, $Ncstn^{-/-}$ and $Ncstn^{-/-}Tet2^{-/-}$ littermates 7 weeks after birth. FIG. 9H is a bar graph showing bone marrow GMP absolute cell number of WT, $Ncstn^{-/-}$ and $Ncstn^{-/-}Tet2^{-/-}$ mice 7 weeks after birth. Data represent mean±SD of 3 different mice per cohort. FIG. 9I is a Kaplan-Meier survival analysis of mice of indicated genotypes (n=4 per cohort). FIG. 9J is a representative FACS analysis of chimerism and myeloid cells from peripheral blood of mice transplanted with 2×10$^6$ splenocytes from $Ncstn^{-/-}$ and $Ncstn^{-/-}$ $Tet2^{-/-}$ (CD45.2) and 5×10$^5$ WT support bone marrow cells (CD45.1), 10 weeks after transplantation. 2 mice per cohort are shown. FIG. 9K is a graph depicting the evolution of peripheral white blood cell count in the two cohorts of transplanted mice. FIG. 9L is a Kaplan-Meier survival analysis of the two cohorts of transplanted mice. Data are representative of mean±SD. ($Ncstn^{-/-}$ cohort n=6; $Ncstn^{-/-}Tet2^{-/-}$ cohort n=4).

FIG. 10A shows representative Annexin V/7AAD FACS plot of THP1 cells treated with control IgG2a, Dll4-Fc or MHN2-25 Notch2 agonist antibody for 24 h. The bar graph of FIG. 10B shows quantification of apoptotic THP1 cells following treatment with IgG2a, Dll4-Fc or MHN2-25. FIG. 10C is a graph showing quantitation of HES1 expression following treatment of THP1 cells with IgG2a, Dll4-Fc or MHN2-25. Expression analysis was carried out using quantitative RT-PCR. All data are representative of mean±SD, n=3, ** represent pvalue <0.01.

DETAILED DESCRIPTION OF THE INVENTION

Figures 1A, 1B, 1C, 1D, 1E, 1F:
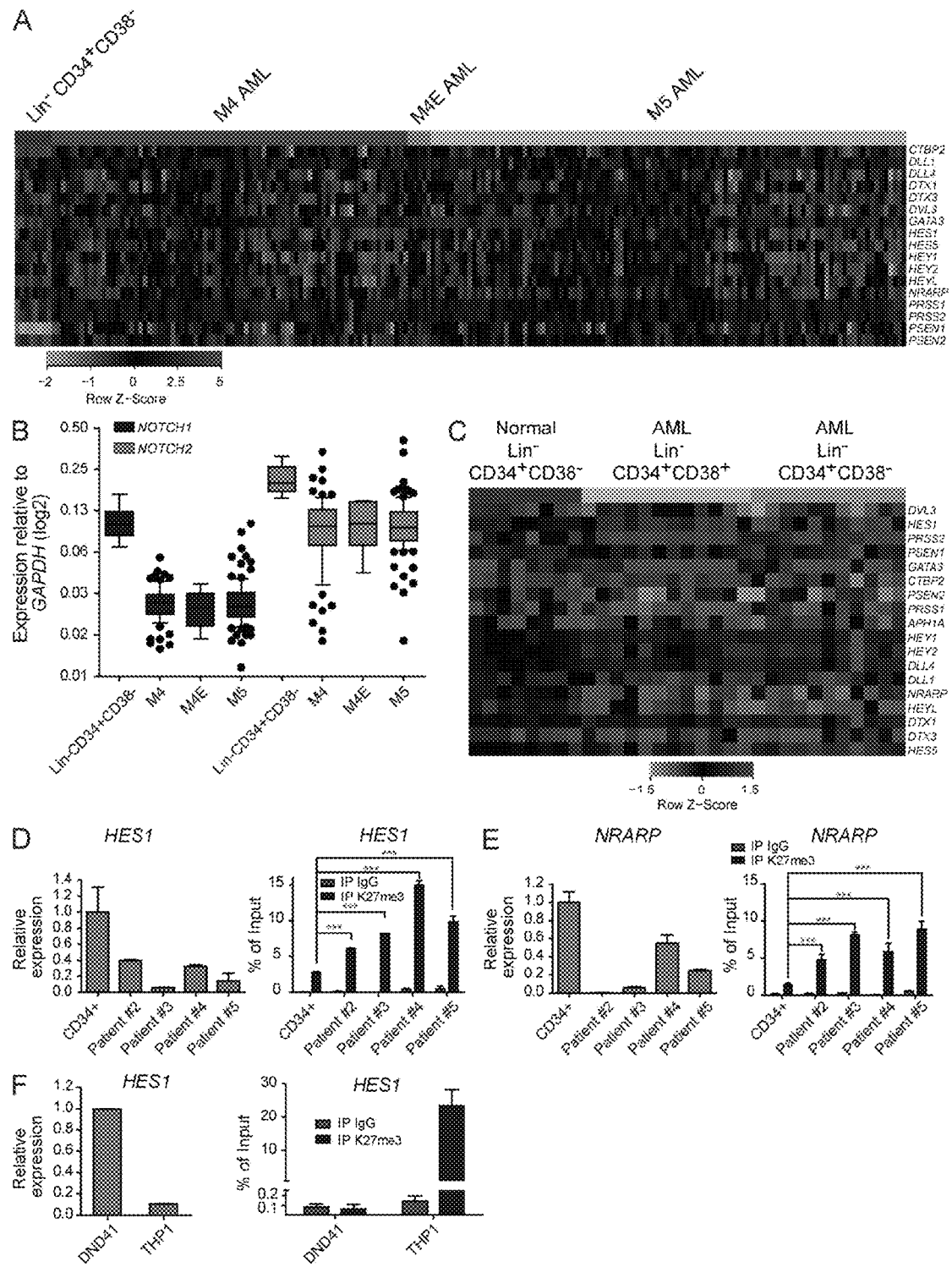
FIGS. 1A-1F demonstrate Notch signaling pathway silencing in AML patients.

A first aspect of the present invention is directed to a method of inducing cell differentiation and cell death in a population of leukemia-initiating cells (LICs). This method involves administering a Notch receptor agonist to the population of LICs under conditions effective to induce cell differentiation and cell death in the population of leukemia LICs.

As described herein, leukemia initiating cells represent a subset of leukemic cells that possess properties similar to normal hematopoietic stem cells such as self-renewal, quiescence, and resistance to traditional chemotherapy (Bonnet & Dick, "Human Acute Myeloid Leukemia is Organized as a Hierarchy That Originates From a Primitive Hematopoietic Cell," *Nat. Med.* 3:730-737 (1997); Huntly & Gilliland, "Leukaemia Stem Cells and the Evolution of Cancer-Stem-Cell Research," *Nat. Rev. Cancer* 5:311-321 (2005), which are hereby incorporated by reference in their entirety). As a result, the LIC subset acts as a reservoir of cells contributing to disease, in particular disease relapse. LIC populations have been identified in acute myeloid leukemia, chronic phase and blast crisis CML (Jamieson et al., "Granulocyte-Macrophage Progenitors as Candidate Leukemic Stem Cells In Blast-Crisis CML," *N. Engl. J. Med.* 351:657-667 (2004); Sirard et al., "Normal and Leukemic SCID-Repopulating Cells (SRC) Coexist in the Bone Marrow and Peripheral Blood From CML Patients in Chronic Phase, Whereas Leukemic SRC are Detected in Blast Crisis," *Blood* 87:1539-1548 (1996); Wang et al., "High Level Engraftment of NOD/SCID Mice by Primitive Normal and Leukemic Hematopoietic Cells From Patients With Chronic Myeloid Leukemia in Chronic Phase," *Blood* 91:2406-2414 (1998), which are hereby incorporated by reference in their entirety), and B-cell acute lymphoblastic leukemia (Castro Alves et al., "Leukemia-initiating Cells of Patient-Derived Acute Lymphoblastic Leukemia Xenografts are Sensitive Toward TRAIL," *Blood* 119(18):4224-7 (2012), which is hereby incorporated by reference).

In accordance with this aspect of the present invention, leukemic initiating cells in which Notch signaling is tumor suppressive are administered a Notch receptor agonist. In one embodiment of the present invention, the LIC population is a population of acute myeloid leukemia (AML) LICs. Data suggests that AML is composed of biologically distinct leukemic stem (initiating cells), progenitor, and blast populations in which the stem cells comprise 0.1%-1% of the blasts and are largely quiescent but capable of endless renewal (Roboz, G., "Novel Approaches to the Treatment of Acute Myeloid Leukemia," *Hematology* 1:43-49 (2011), which is hereby incorporated by reference in its entirety). Acute myeloid leukemia LICs, like other LIC populations can be identified by their ability to recapitulate disease in animal models and by their cell surface marker expression. Acute myeloid leukemia LICs comprises a population of Lin$^-$ CD34$^+$ acute myeloid leukemia cells. Acute myeloid leukemia LICs can further be identified by Lin$^-$ CD34$^+$ CD38$^-$ cell surface expression profile, or a Lin$^-$CD34$^+$ CD38$^{-/+}$ cell surface expression profile. Other antigens preferentially expressed by AML LICs include, without limitation, CD123, CD44, CD47, and CLL01.

In accordance with this aspect of the present invention, the Notch receptor agonist can be administered in vivo or in vitro to induce LIC differentiation and cell death. Administration of the Notch receptor agonist can be repeated periodically as needed (e.g., hourly, daily, weekly, monthly, yearly) to induce cell differentiation and cell death of LICs in a population of AML cells.

Humans possess four heterodimeric transmembrane Notch receptors, i.e., Notch receptors 1-4. In accordance with this and all aspects of the present invention, a Notch receptor agonist binds to a Notch receptor and has a direct effect on a Notch receptor bearing cell. The Notch receptor agonist will bind Notch receptor and initiate or induce Notch mediated signaling events, such as, e.g., cause the intracellular domain of Notch to be cleaved and translocated to the nucleus. In one embodiment of the present invention, the Notch receptor agonist is a Notch 1 receptor agonist. In another embodiment of the present invention, the Notch receptor agonist is a Notch 2 receptor agonist. In yet another embodiment of the present invention, the Notch receptor agonist is capable of binding to and activating both Notch 1 and Notch 2 receptors.

Suitable Notch receptor agonists include, without limitation, Notch receptor agonist antibodies or active binding fragments thereof, Notch receptor-activating ligands, and Notch receptor small molecule agonists.

In one embodiment of the present invention, the Notch receptor agonist is a Notch agonist antibody. A Notch receptor agonist antibody of the present invention encompasses any immunoglobulin molecule that specifically binds to an epitope of a Notch receptor and induces Notch receptor mediated signaling. As used herein, "epitope" refers to a region of the Notch receptor that is recognized by the isolated antibody and involved in mediating the downstream molecular signaling pathway triggered by Notch receptor-Notch ligand binding interaction. Li et al., "Modulation of Notch Signaling by Antibodies Specific for the Extracellular Negative Regulatory Region of NOTCH3," *J. Biol. Chem.* 283(12):8046-54 (2008), which is hereby incorporated by reference in its entirety, has reported the generation of specific Notch3 agonist antibodies. These antibodies recognize the negative regulatory region (NRR) of the Notch3 receptor which consists of three Lin12/Notch repeats (LNR1-3) and a heterodimerization domain (HD). Notch1 and Notch2 receptors share similar domains to Notch3. Accordingly, in one embodiment of the present invention, the antibody of the present invention binds specifically to an epitope present on the Notch 1 receptor with or without binding to any of the other Notch receptors. Suitable epitopes include the NRR domain, comprising amino acid residues 1446-1733 of the human Notch 1 receptor which has the amino acid sequence of SEQ ID NO: 1 (UnitProtKB Accession No. P46531) as shown below. Particular epitopes within the NRR domain that a Notch agonist antibody of the present invention can recognize include any one of the LIN repeat domains which comprise amino acid residues 1449-1489, 1490-1531, and 1532-1571 of SEQ ID NO: 1. Alternatively, a suitable Notch 1 receptor agonist antibody recognizes and binds to an epitope within the EGF domain of Notch 1 corresponding to amino acid residues 20-1426 of SEQ ID NO: 1.

```
Met Pro Pro Leu Leu Ala Pro Leu Leu Cys Leu Ala Leu Leu Pro Ala
1               5                   10              15

Leu Ala Ala Arg Gly Pro Arg Cys Ser Gln Pro Gly Glu Thr Cys Leu
            20              25                  30

Asn Gly Gly Lys Cys Glu Ala Ala Asn Gly Thr Glu Ala Cys Val Cys
            35              40                  45

Gly Gly Ala Phe Val Gly Pro Arg Cys Gln Asp Pro Asn Pro Cys Leu
        50              55              60

Ser Thr Pro Cys Lys Asn Ala Gly Thr Cys His Val Val Asp Arg Arg
65                  70              75                      80

Gly Val Ala Asp Tyr Ala Cys Ser Cys Ala Leu Gly Phe Ser Gly Pro
                85              90              95

Leu Cys Leu Thr Pro Leu Asp Asn Ala Cys Leu Thr Asn Pro Cys Arg
            100             105                 110

Asn Gly Gly Thr Cys Asp Leu Leu Thr Leu Thr Glu Tyr Lys Cys Arg
            115             120                 125

Cys Pro Pro Gly Trp Ser Gly Lys Ser Cys Gln Gln Ala Asp Pro Cys
    130             135                 140

Ala Ser Asn Pro Cys Ala Asn Gly Gly Gln Cys Leu Pro Phe Glu Ala
145                 150             155                     160

Ser Tyr Ile Cys His Cys Pro Pro Ser Phe His Gly Pro Thr Cys Arg
                165             170             175

Gln Asp Val Asn Glu Cys Gly Gln Lys Pro Gly Leu Cys Arg His Gly
            180             185                 190

Gly Thr Cys His Asn Glu Val Gly Ser Tyr Arg Cys Val Cys Arg Ala
            195             200                 205

Thr His Thr Gly Pro Asn Cys Glu Arg Pro Tyr Val Pro Cys Ser Pro
    210             215                 220

Ser Pro Cys Gln Asn Gly Gly Thr Cys Arg Pro Thr Gly Asp Val Thr
225                 230             235                     240
```

-continued

His Glu Cys Ala Cys Leu Pro Gly Phe Thr Gly Gln Asn Cys Glu Glu
            245                 250                 255

Asn Ile Asp Asp Cys Pro Gly Asn Asn Cys Lys Asn Gly Gly Ala Cys
        260                 265                 270

Val Asp Gly Val Asn Thr Tyr Asn Cys Arg Cys Pro Glu Trp Thr
        275                 280                 285

Gly Gln Tyr Cys Thr Glu Asp Val Asp Glu Cys Gln Leu Met Pro Asn
        290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
            325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
            355                 360                 365

Leu Cys His Leu Asn Asp Ala Cys Ile Ser Asn Pro Cys Asn Glu Gly
            370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
            405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg
            435                 440                 445

Cys Glu Ile Asp Val Asn Glu Cys Val Ser Asn Pro Cys Gln Asn Asp
450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
            485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
            515                 520                 525

Val Asp Glu Cys Ala Ser Thr Pro Cys Lys Asn Gly Ala Lys Cys Leu
            530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
            565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
            595                 600                 605

Ser Gln Pro Cys Arg His Gly Gly Thr Cys Gln Asp Arg Asp Asn Ala
            610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
            645                 650                 655

Asp Lys Ile Asp Gly Tyr Glu Cys Ala Cys Glu Pro Gly Tyr Thr Gly
            660                 665                 670

-continued

```
Ser Met Cys Asn Ile Asn Ile Asp Glu Cys Ala Gly Asn Pro Cys His
            675                 680                 685
Asn Gly Gly Thr Cys Glu Asp Gly Ile Asn Gly Phe Thr Cys Arg Cys
            690                 695                 700
Pro Glu Gly Tyr His Asp Pro Thr Cys Leu Ser Glu Val Asn Glu Cys
705                 710                 715                 720
Asn Ser Asn Pro Cys Val His Gly Ala Cys Arg Asp Ser Leu Asn Gly
                725                 730                 735
Tyr Lys Cys Asp Cys Asp Pro Gly Trp Ser Gly Thr Asn Cys Asp Ile
            740                 745                 750
Asn Asn Asn Glu Cys Glu Ser Asn Pro Cys Val Asn Gly Gly Thr Cys
            755                 760                 765
Lys Asp Met Thr Ser Gly Tyr Val Cys Thr Cys Arg Glu Gly Phe Ser
            770                 775                 780
Gly Pro Asn Cys Gln Thr Asn Ile Asn Glu Cys Ala Ser Asn Pro Cys
785                 790                 795                 800
Leu Asn Gln Gly Thr Cys Ile Asp Asp Val Ala Gly Tyr Lys Cys Asn
                805                 810                 815
Cys Leu Leu Pro Tyr Thr Gly Ala Thr Cys Glu Val Val Leu Ala Pro
            820                 825                 830
Cys Ala Pro Ser Pro Cys Arg Asn Gly Gly Glu Cys Arg Gln Ser Glu
            835                 840                 845
Asp Tyr Glu Ser Phe Ser Cys Val Cys Pro Thr Gly Trp Gln Gly Gln
            850                 855                 860
Thr Cys Glu Val Asp Ile Asn Glu Cys Val Leu Ser Pro Cys Arg His
865                 870                 875                 880
Gly Ala Ser Cys Gln Asn Thr His Gly Gly Tyr Arg Cys His Cys Gln
                885                 890                 895
Ala Gly Tyr Ser Gly Arg Asn Cys Glu Thr Asp Ile Asp Asp Cys Arg
            900                 905                 910
Pro Asn Pro Cys His Asn Gly Gly Ser Cys Thr Asp Gly Ile Asn Thr
            915                 920                 925
Ala Phe Cys Asp Cys Leu Pro Gly Phe Arg Gly Thr Phe Cys Glu Glu
            930                 935                 940
Asp Ile Asn Glu Cys Ala Ser Asp Pro Cys Arg Asn Gly Ala Asn Cys
945                 950                 955                 960
Thr Asp Cys Val Asp Ser Tyr Thr Cys Thr Cys Pro Ala Gly Phe Ser
                965                 970                 975
Gly Ile His Cys Glu Asn Asn Thr Pro Asp Cys Thr Glu Ser Ser Cys
            980                 985                 990
Phe Asn Gly Gly Thr Cys Val Asp Gly Ile Asn Ser Phe Thr Cys Leu
            995                 1000                1005
Cys Pro Pro Gly Phe Thr Gly Ser Tyr Cys Gln His Asp Val Asn
            1010                1015                1020
Glu Cys Asp Ser Gln Pro Cys Leu His Gly Gly Thr Cys Gln Asp
            1025                1030                1035
Gly Cys Gly Ser Tyr Arg Cys Thr Cys Pro Gln Gly Tyr Thr Gly
            1040                1045                1050
Pro Asn Cys Gln Asn Leu Val His Trp Cys Asp Ser Ser Pro Cys
            1055                1060                1065
Lys Asn Gly Gly Lys Cys Trp Gln Thr His Thr Gln Tyr Arg Cys
            1070                1075                1080
Glu Cys Pro Ser Gly Trp Thr Gly Leu Tyr Cys Asp Val Pro Ser
            1085                1090                1095
```

-continued

Val Ser Cys Glu Val Ala Ala Gln Arg Gln Gly Val Asp Val Ala
    1100                1105                1110

Arg Leu Cys Gln His Gly Gly Leu Cys Val Asp Ala Gly Asn Thr
    1115                1120                1125

His His Cys Arg Cys Gln Ala Gly Tyr Thr Gly Ser Tyr Cys Glu
    1130                1135                1140

Asp Leu Val Asp Glu Cys Ser Pro Ser Pro Cys Gln Asn Gly Ala
    1145                1150                1155

Thr Cys Thr Asp Tyr Leu Gly Gly Tyr Ser Cys Lys Cys Val Ala
    1160                1165                1170

Gly Tyr His Gly Val Asn Cys Ser Glu Glu Ile Asp Glu Cys Leu
    1175                1180                1185

Ser His Pro Cys Gln Asn Gly Gly Thr Cys Leu Asp Leu Pro Asn
    1190                1195                1200

Thr Tyr Lys Cys Ser Cys Pro Arg Gly Thr Gln Gly Val His Cys
    1205                1210                1215

Glu Ile Asn Val Asp Asp Cys Asn Pro Pro Val Asp Pro Val Ser
    1220                1225                1230

Arg Ser Pro Lys Cys Phe Asn Asn Gly Thr Cys Val Asp Gln Val
     1235                1240                 1245

Gly Gly Tyr Ser Cys Thr Cys Pro Pro Gly Phe Val Gly Glu Arg
    1250                1255                1260

Cys Glu Gly Asp Val Asn Glu Cys Leu Ser Asn Pro Cys Asp Ala
    1265                1270                1275

Arg Gly Thr Gln Asn Cys Val Gln Arg Val Asn Asp Phe His Cys
    1280                1285                1290

Glu Cys Arg Ala Gly His Thr Gly Arg Arg Cys Glu Ser Val Ile
    1295                1300                1305

Asn Gly Cys Lys Gly Lys Pro Cys Lys Asn Gly Gly Thr Cys Ala
    1310                1315                1320

Val Ala Ser Asn Thr Ala Arg Gly Phe Ile Cys Lys Cys Pro Ala
    1325                1330                1335

Gly Phe Glu Gly Ala Thr Cys Glu Asn Asp Ala Arg Thr Cys Gly
    1340                1345                1350

Ser Leu Arg Cys Leu Asn Gly Gly Thr Cys Ile Ser Gly Pro Arg
    1355                1360                1365

Ser Pro Thr Cys Leu Cys Leu Gly Pro Phe Thr Gly Pro Glu Cys
    1370                1375                1380

Gln Phe Pro Ala Ser Ser Pro Cys Leu Gly Gly Asn Pro Cys Tyr
    1385                1390                1395

Asn Gln Gly Thr Cys Glu Pro Thr Ser Glu Ser Pro Phe Tyr Arg
    1400                1405                1410

Cys Leu Cys Pro Ala Lys Phe Asn Gly Leu Leu Cys His Ile Leu
    1415                1420                1425

Asp Tyr Ser Phe Gly Gly Gly Ala Gly Arg Asp Ile Pro Pro Pro
    1430                1435                1440

Leu Ile Glu Glu Ala Cys Glu Leu Pro Glu Cys Gln Glu Asp Ala
    1445                1450                1455

Gly Asn Lys Val Cys Ser Leu Gln Cys Asn Asn His Ala Cys Gly
    1460                1465                1470

Trp Asp Gly Gly Asp Cys Ser Leu Asn Phe Asn Asp Pro Trp Lys
    1475                1480                1485

Asn Cys Thr Gln Ser Leu Gln Cys Trp Lys Tyr Phe Ser Asp Gly
    1490                1495                1500

-continued

```
His Cys Asp Ser Gln Cys Asn Ser Ala Gly Cys Leu Phe Asp Gly
    1505                1510                1515

Phe Asp Cys Gln Arg Ala Glu Gly Gln Cys Asn Pro Leu Tyr Asp
    1520                1525                1530

Gln Tyr Cys Lys Asp His Phe Ser Asp Gly His Cys Asp Gln Gly
    1535                1540                1545

Cys Asn Ser Ala Glu Cys Glu Trp Asp Gly Leu Asp Cys Ala Glu
    1550                1555                1560

His Val Pro Glu Arg Leu Ala Ala Gly Thr Leu Val Val Val Val
    1565                1570                1575

Leu Met Pro Pro Glu Gln Leu Arg Asn Ser Ser Phe His Phe Leu
    1580                1585                1590

Arg Glu Leu Ser Arg Val Leu His Thr Asn Val Val Phe Lys Arg
    1595                1600                1605

Asp Ala His Gly Gln Gln Met Ile Phe Pro Tyr Tyr Gly Arg Glu
    1610                1615                1620

Glu Glu Leu Arg Lys His Pro Ile Lys Arg Ala Ala Glu Gly Trp
    1625                1630                1635

Ala Ala Pro Asp Ala Leu Leu Gly Gln Val Lys Ala Ser Leu Leu
    1640                1645                1650

Pro Gly Gly Ser Glu Gly Gly Arg Arg Arg Arg Glu Leu Asp Pro
    1655                1660                1665

Met Asp Val Arg Gly Ser Ile Val Tyr Leu Glu Ile Asp Asn Arg
    1670                1675                1680

Gln Cys Val Gln Ala Ser Ser Gln Cys Phe Gln Ser Ala Thr Asp
    1685                1690                1695

Val Ala Ala Phe Leu Gly Ala Leu Ala Ser Leu Gly Ser Leu Asn
    1700                1705                1710

Ile Pro Tyr Lys Ile Glu Ala Val Gln Ser Glu Thr Val Glu Pro
    1715                1720                1725

Pro Pro Pro Ala Gln Leu His Phe Met Tyr Val Ala Ala Ala Ala
    1730                1735                1740

Phe Val Leu Leu Phe Phe Val Gly Cys Gly Val Leu Leu Ser Arg
    1745                1750                1755

Lys Arg Arg Arg Gln His Gly Gln Leu Trp Phe Pro Glu Gly Phe
    1760                1765                1770

Lys Val Ser Glu Ala Ser Lys Lys Lys Arg Arg Glu Pro Leu Gly
    1775                1780                1785

Glu Asp Ser Val Gly Leu Lys Pro Leu Lys Asn Ala Ser Asp Gly
    1790                1795                1800

Ala Leu Met Asp Asp Asn Gln Asn Glu Trp Gly Asp Glu Asp Leu
    1805                1810                1815

Glu Thr Lys Lys Phe Arg Phe Glu Glu Pro Val Val Leu Pro Asp
    1820                1825                1830

Leu Asp Asp Gln Thr Asp His Arg Gln Trp Thr Gln Gln His Leu
    1835                1840                1845

Asp Ala Ala Asp Leu Arg Met Ser Ala Met Ala Pro Thr Pro Pro
    1850                1855                1860

Gln Gly Glu Val Asp Ala Asp Cys Met Asp Val Asn Val Arg Gly
    1865                1870                1875

Pro Asp Gly Phe Thr Pro Leu Met Ile Ala Ser Cys Ser Gly Gly
    1880                1885                1890

Gly Leu Glu Thr Gly Asn Ser Glu Glu Glu Glu Asp Ala Pro Ala
    1895                1900                1905
```

-continued

```
Val Ile Ser Asp Phe Ile Tyr Gln Gly Ala Ser Leu His Asn Gln
1910                1915                1920

Thr Asp Arg Thr Gly Glu Thr Ala Leu His Leu Ala Ala Arg Tyr
    1925                1930                1935

Ser Arg Ser Asp Ala Ala Lys Arg Leu Leu Glu Ala Ser Ala Asp
    1940                1945                1950

Ala Asn Ile Gln Asp Asn Met Gly Arg Thr Pro Leu His Ala Ala
    1955                1960                1965

Val Ser Ala Asp Ala Gln Gly Val Phe Gln Ile Leu Ile Arg Asn
    1970                1975                1980

Arg Ala Thr Asp Leu Asp Ala Arg Met His Asp Gly Thr Thr Pro
    1985                1990                1995

Leu Ile Leu Ala Ala Arg Leu Ala Val Glu Gly Met Leu Glu Asp
    2000                2005                2010

Leu Ile Asn Ser His Ala Asp Val Asn Ala Val Asp Asp Leu Gly
    2015                2020                2025

Lys Ser Ala Leu His Trp Ala Ala Ala Val Asn Asn Val Asp Ala
    2030                2035                2040

Ala Val Val Leu Leu Lys Asn Gly Ala Asn Lys Asp Met Gln Asn
    2045                2050                2055

Asn Arg Glu Glu Thr Pro Leu Phe Leu Ala Ala Arg Glu Gly Ser
    2060                2065                2070

Tyr Glu Thr Ala Lys Val Leu Leu Asp His Phe Ala Asn Arg Asp
    2075                2080                2085

Ile Thr Asp His Met Asp Arg Leu Pro Arg Asp Ile Ala Gln Glu
    2090                2095                2100

Arg Met His His Asp Ile Val Arg Leu Leu Asp Glu Tyr Asn Leu
    2105                2110                2115

Val Arg Ser Pro Gln Leu His Gly Ala Pro Leu Gly Gly Thr Pro
    2120                2125                2130

Thr Leu Ser Pro Pro Leu Cys Ser Pro Asn Gly Tyr Leu Gly Ser
    2135                2140                2145

Leu Lys Pro Gly Val Gln Gly Lys Lys Val Arg Lys Pro Ser Ser
    2150                2155                2160

Lys Gly Leu Ala Cys Gly Ser Lys Glu Ala Lys Asp Leu Lys Ala
    2165                2170                2175

Arg Arg Lys Lys Ser Gln Asp Gly Lys Gly Cys Leu Leu Asp Ser
    2180                2185                2190

Ser Gly Met Leu Ser Pro Val Asp Ser Leu Glu Ser Pro His Gly
    2195                2200                2205

Tyr Leu Ser Asp Val Ala Ser Pro Pro Leu Leu Pro Ser Pro Phe
    2210                2215                2220

Gln Gln Ser Pro Ser Val Pro Leu Asn His Leu Pro Gly Met Pro
    2225                2230                2235

Asp Thr His Leu Gly Ile Gly His Leu Asn Val Ala Ala Lys Pro
    2240                2245                2250

Glu Met Ala Ala Leu Gly Gly Gly Gly Arg Leu Ala Phe Glu Thr
    2255                2260                2265

Gly Pro Pro Arg Leu Ser His Leu Pro Val Ala Ser Gly Thr Ser
    2270                2275                2280

Thr Val Leu Gly Ser Ser Ser Gly Gly Ala Leu Asn Phe Thr Val
    2285                2290                2295

Gly Gly Ser Thr Ser Leu Asn Gly Gln Cys Glu Trp Leu Ser Arg
    2300                2305                2310
```

-continued

```
Leu Gln Ser Gly Met Val Pro Asn Gln Tyr Asn Pro Leu Arg Gly
    2315                2320                2325

Ser Val Ala Pro Gly Pro Leu Ser Thr Gln Ala Pro Ser Leu Gln
    2330                2335                2340

His Gly Met Val Gly Pro Leu His Ser Ser Leu Ala Ala Ser Ala
    2345                2350                2355

Leu Ser Gln Met Met Ser Tyr Gln Gly Leu Pro Ser Thr Arg Leu
    2360                2365                2370

Ala Thr Gln Pro His Leu Val Gln Thr Gln Gln Val Gln Pro Gln
    2375                2380                2385

Asn Leu Gln Met Gln Gln Asn Leu Gln Pro Ala Asn Ile Gln
    2390                2395                2400

Gln Gln Gln Ser Leu Gln Pro Pro Pro Pro Pro Gln Pro His
    2405                2410                2415

Leu Gly Val Ser Ser Ala Ala Ser Gly His Leu Gly Arg Ser Phe
    2420                2425                2430

Leu Ser Gly Glu Pro Ser Gln Ala Asp Val Gln Pro Leu Gly Pro
    2435                2440                2445

Ser Ser Leu Ala Val His Thr Ile Leu Pro Gln Glu Ser Pro Ala
    2450                2455                2460

Leu Pro Thr Ser Leu Pro Ser Ser Leu Val Pro Pro Val Thr Ala
    2465                2470                2475

Ala Gln Phe Leu Thr Pro Pro Ser Gln His Ser Tyr Ser Ser Pro
    2480                2485                2490

Val Asp Asn Thr Pro Ser His Gln Leu Gln Val Pro Glu His Pro
    2495                2500                2505

Phe Leu Thr Pro Ser Pro Glu Ser Pro Asp Gln Trp Ser Ser Ser
    2510                2515                2520

Ser Pro His Ser Asn Val Ser Asp Trp Ser Glu Gly Val Ser Ser
    2525                2530                2535

Pro Pro Thr Ser Met Gln Ser Gln Ile Ala Arg Ile Pro Glu Ala
    2540                2545                2550

Phe Lys
```

In another embodiment of the present invention, the agonist antibody binds specifically to an epitope present on the Notch 2 receptor with or without binding to any of the other Notch receptors. Suitable epitopes include the NRR domain, comprising amino acid residues 1425-1677 of the human Notch 2 receptor which has the amino acid sequence of SEQ ID NO: 2 (UniProtKB Accession No. Q04721) as shown below. Particular epitopes within the NRR domain that the Notch agonist antibody of the present invention can recognize and bind to include the LIN repeat domains which comprise amino acid residues 1425-1465, 1466-1502, and 1503-1544 of SEQ ID NO: 2. Alternatively, a suitable Notch 2 receptor agonist antibody recognizes and binds to an epitope within the EGF domain of Notch 2 corresponding to amino acid residues 26-1412 of SEQ ID NO:2.

```
Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
            20                  25                  30

Glu Pro Cys Val Asn Glu Gly Met Cys Val Thr Tyr His Asn Gly Thr
        35                  40                  45

Gly Tyr Cys Lys Cys Pro Glu Gly Phe Leu Gly Glu Tyr Cys Gln His
    50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95
```

-continued

```
Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
        355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
        515                 520                 525
```

-continued

```
Cys Gln Ile Asp Ile Asp Asp Cys Ser Ser Thr Pro Cys Leu Asn Gly
    530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
        595                 600                 605

Asp Glu Cys Tyr Ser Ser Pro Cys Leu Asn Asp Gly Arg Cys Ile Asp
    610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
                645                 650                 655

Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
        675                 680                 685

Asn Pro Cys Arg Lys Gly Ala Thr Cys Ile Asn Gly Val Asn Gly Phe
    690                 695                 700

Arg Cys Ile Cys Pro Glu Gly Pro His His Pro Ser Cys Tyr Ser Gln
705                 710                 715                 720

Val Asn Glu Cys Leu Ser Asn Pro Cys Ile His Gly Asn Cys Thr Gly
                725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
        755                 760                 765

Gly Gly Thr Cys Asp Asn Leu Val Asn Gly Tyr Arg Cys Thr Cys Lys
    770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
                805                 810                 815

Tyr Thr Cys His Cys Val Leu Pro Tyr Thr Gly Lys Asn Cys Gln Thr
            820                 825                 830

Val Leu Ala Pro Cys Ser Pro Asn Pro Cys Glu Asn Ala Ala Val Cys
        835                 840                 845

Lys Glu Ser Pro Asn Phe Glu Ser Tyr Thr Cys Leu Cys Ala Pro Gly
    850                 855                 860

Trp Gln Gly Gln Arg Cys Thr Ile Asp Ile Asp Glu Cys Ile Ser Lys
865                 870                 875                 880

Pro Cys Met Asn His Gly Leu Cys His Asn Thr Gln Gly Ser Tyr Met
                885                 890                 895

Cys Glu Cys Pro Pro Gly Phe Ser Gly Met Asp Cys Glu Glu Asp Ile
            900                 905                 910

Asp Asp Cys Leu Ala Asn Pro Cys Gln Asn Gly Gly Ser Cys Met Asp
        915                 920                 925

Gly Val Asn Thr Phe Ser Cys Leu Cys Leu Pro Gly Phe Thr Gly Asp
    930                 935                 940

Lys Cys Gln Thr Asp Met Asn Glu Cys Leu Ser Glu Pro Cys Lys Asn
945                 950                 955                 960
```

-continued

Gly Gly Thr Cys Ser Asp Tyr Val Asn Ser Tyr Thr Cys Lys Cys Gln
        965                 970                 975

Ala Gly Phe Asp Gly Val His Cys Glu Asn Asn Ile Asn Glu Cys Thr
        980                 985                 990

Glu Ser Ser Cys Phe Asn Gly Gly Thr Cys Val Asp Gly Ile Asn Ser
        995                1000                1005

Phe Ser Cys Leu Cys Pro Val Gly Phe Thr Gly Ser Phe Cys Leu
   1010                1015                1020

His Glu Ile Asn Glu Cys Ser Ser His Pro Cys Leu Asn Glu Gly
   1025                1030                1035

Thr Cys Val Asp Gly Leu Gly Thr Tyr Arg Cys Ser Cys Pro Leu
   1040                1045                1050

Gly Tyr Thr Gly Lys Asn Cys Gln Thr Leu Val Asn Leu Cys Ser
   1055                1060                1065

Arg Ser Pro Cys Lys Asn Lys Gly Thr Cys Val Gln Lys Lys Ala
   1070                1075                1080

Glu Ser Gln Cys Leu Cys Pro Ser Gly Trp Ala Gly Ala Tyr Cys
   1085                1090                1095

Asp Val Pro Asn Val Ser Cys Asp Ile Ala Ala Ser Arg Arg Gly
   1100                1105                1110

Val Leu Val Glu His Leu Cys Gln His Ser Gly Val Cys Ile Asn
   1115                1120                1125

Ala Gly Asn Thr His Tyr Cys Gln Cys Pro Leu Gly Tyr Thr Gly
   1130                1135                1140

Ser Tyr Cys Glu Glu Gln Leu Asp Glu Cys Ala Ser Asn Pro Cys
   1145                1150                1155

Gln His Gly Ala Thr Cys Ser Asp Phe Ile Gly Gly Tyr Arg Cys
   1160                1165                1170

Glu Cys Val Pro Gly Tyr Gln Gly Val Asn Cys Glu Tyr Glu Val
   1175                1180                1185

Asp Glu Cys Gln Asn Gln Pro Cys Gln Asn Gly Gly Thr Cys Ile
   1190                1195                1200

Asp Leu Val Asn His Phe Lys Cys Ser Cys Pro Pro Gly Thr Arg
   1205                1210                1215

Gly Leu Leu Cys Glu Glu Asn Ile Asp Asp Cys Ala Arg Gly Pro
   1220                1225                1230

His Cys Leu Asn Gly Gly Gln Cys Met Asp Arg Ile Gly Gly Tyr
   1235                1240                1245

Ser Cys Arg Cys Leu Pro Gly Phe Ala Gly Glu Arg Cys Glu Gly
   1250                1255                1260

Asp Ile Asn Glu Cys Leu Ser Asn Pro Cys Ser Ser Glu Gly Ser
   1265                1270                1275

Leu Asp Cys Ile Gln Leu Thr Asn Asp Tyr Leu Cys Val Cys Arg
   1280                1285                1290

Ser Ala Phe Thr Gly Arg His Cys Glu Thr Phe Val Asp Val Cys
   1295                1300                1305

Pro Gln Met Pro Cys Leu Asn Gly Gly Thr Cys Ala Val Ala Ser
   1310                1315                1320

Asn Met Pro Asp Gly Phe Ile Cys Arg Cys Pro Pro Gly Phe Ser
   1325                1330                1335

Gly Ala Arg Cys Gln Ser Ser Cys Gly Gln Val Lys Cys Arg Lys
   1340                1345                1350

Gly Glu Gln Cys Val His Thr Ala Ser Gly Pro Arg Cys Phe Cys
   1355                1360                1365

-continued

Pro Ser Pro Arg Asp Cys Glu Ser Gly Cys Ala Ser Ser Pro Cys
1370                1375                1380

Gln His Gly Gly Ser Cys His Pro Gln Arg Gln Pro Pro Tyr Tyr
    1385                1390                1395

Ser Cys Gln Cys Ala Pro Pro Phe Ser Gly Ser Arg Cys Glu Leu
1400                1405                1410

Tyr Thr Ala Pro Pro Ser Thr Pro Pro Ala Thr Cys Leu Ser Gln
    1415                1420                1425

Tyr Cys Ala Asp Lys Ala Arg Asp Gly Val Cys Asp Glu Ala Cys
1430                1435                1440

Asn Ser His Ala Cys Gln Trp Asp Gly Gly Asp Cys Ser Leu Thr
    1445                1450                1455

Met Glu Asn Pro Trp Ala Asn Cys Ser Ser Pro Leu Pro Cys Trp
1460                1465                1470

Asp Tyr Ile Asn Asn Gln Cys Asp Glu Leu Cys Asn Thr Val Glu
    1475                1480                1485

Cys Leu Phe Asp Asn Phe Glu Cys Gln Gly Asn Ser Lys Thr Cys
1490                1495                1500

Lys Tyr Asp Lys Tyr Cys Ala Asp His Phe Lys Asp Asn His Cys
    1505                1510                1515

Asp Gln Gly Cys Asn Ser Glu Glu Cys Gly Trp Asp Gly Leu Asp
1520                1525                1530

Cys Ala Ala Asp Gln Pro Glu Asn Leu Ala Glu Gly Thr Leu Val
    1535                1540                1545

Ile Val Val Leu Met Pro Pro Glu Gln Leu Leu Gln Asp Ala Arg
1550                1555                1560

Ser Phe Leu Arg Ala Leu Gly Thr Leu Leu His Thr Asn Leu Arg
    1565                1570                1575

Ile Lys Arg Asp Ser Gln Gly Glu Leu Met Val Tyr Pro Tyr Tyr
1580                1585                1590

Gly Glu Lys Ser Ala Ala Met Lys Lys Gln Arg Met Thr Arg Arg
    1595                1600                1605

Ser Leu Pro Gly Glu Gln Glu Gln Glu Val Ala Gly Ser Lys Val
1610                1615                1620

Phe Leu Glu Ile Asp Asn Arg Gln Cys Val Gln Asp Ser Asp His
    1625                1630                1635

Cys Phe Lys Asn Thr Asp Ala Ala Ala Ala Leu Leu Ala Ser His
1640                1645                1650

Ala Ile Gln Gly Thr Leu Ser Tyr Pro Leu Val Ser Val Val Ser
    1655                1660                1665

Glu Ser Leu Thr Pro Glu Arg Thr Gln Leu Leu Tyr Leu Leu Ala
1670                1675                1680

Val Ala Val Val Ile Ile Leu Phe Ile Ile Leu Leu Gly Val Ile
    1685                1690                1695

Met Ala Lys Arg Lys Arg Lys His Gly Ser Leu Trp Leu Pro Glu
1700                1705                1710

Gly Phe Thr Leu Arg Arg Asp Ala Ser Asn His Lys Arg Arg Glu
    1715                1720                1725

Pro Val Gly Gln Asp Ala Val Gly Leu Lys Asn Leu Ser Val Gln
1730                1735                1740

Val Ser Glu Ala Asn Leu Ile Gly Thr Gly Thr Ser Glu His Trp
    1745                1750                1755

Val Asp Asp Glu Gly Pro Gln Pro Lys Lys Val Lys Ala Glu Asp
1760                1765                1770

-continued

```
Glu Ala Leu Leu Ser Glu Glu Asp Asp Pro Ile Asp Arg Arg Pro
1775                1780                1785

Trp Thr Gln Gln His Leu Glu Ala Ala Asp Ile Arg Arg Thr Pro
1790                1795                1800

Ser Leu Ala Leu Thr Pro Pro Gln Ala Glu Gln Glu Val Asp Val
1805                1810                1815

Leu Asp Val Asn Val Arg Gly Pro Asp Gly Cys Thr Pro Leu Met
1820                1825                1830

Leu Ala Ser Leu Arg Gly Gly Ser Ser Asp Leu Ser Asp Glu Asp
1835                1840                1845

Glu Asp Ala Glu Asp Ser Ser Ala Asn Ile Ile Thr Asp Leu Val
1850                1855                1860

Tyr Gln Gly Ala Ser Leu Gln Ala Gln Thr Asp Arg Thr Gly Glu
1865                1870                1875

Met Ala Leu His Leu Ala Ala Arg Tyr Ser Arg Ala Asp Ala Ala
1880                1885                1890

Lys Arg Leu Leu Asp Ala Gly Ala Asp Ala Asn Ala Gln Asp Asn
1895                1900                1905

Met Gly Arg Cys Pro Leu His Ala Ala Val Ala Ala Asp Ala Gln
1910                1915                1920

Gly Val Phe Gln Ile Leu Ile Arg Asn Arg Val Thr Asp Leu Asp
1925                1930                1935

Ala Arg Met Asn Asp Gly Thr Thr Pro Leu Ile Leu Ala Ala Arg
1940                1945                1950

Leu Ala Val Glu Gly Met Val Ala Glu Leu Ile Asn Cys Gln Ala
1955                1960                1965

Asp Val Asn Ala Val Asp Asp His Gly Lys Ser Ala Leu His Trp
1970                1975                1980

Ala Ala Ala Val Asn Asn Val Glu Ala Thr Leu Leu Leu Leu Lys
1985                1990                1995

Asn Gly Ala Asn Arg Asp Met Gln Asp Asn Lys Glu Glu Thr Pro
2000                2005                2010

Leu Phe Leu Ala Ala Arg Glu Gly Ser Tyr Glu Ala Ala Lys Ile
2015                2020                2025

Leu Leu Asp His Phe Ala Asn Arg Asp Ile Thr Asp His Met Asp
2030                2035                2040

Arg Leu Pro Arg Asp Val Ala Arg Asp Arg Met His His Asp Ile
2045                2050                2055

Val Arg Leu Leu Asp Glu Tyr Asn Val Thr Pro Ser Pro Pro Gly
2060                2065                2070

Thr Val Leu Thr Ser Ala Leu Ser Pro Val Ile Cys Gly Pro Asn
2075                2080                2085

Arg Ser Phe Leu Ser Leu Lys His Thr Pro Met Gly Lys Lys Ser
2090                2095                2100

Arg Arg Pro Ser Ala Lys Ser Thr Met Pro Thr Ser Leu Pro Asn
2105                2110                2115

Leu Ala Lys Glu Ala Lys Asp Ala Lys Gly Ser Arg Arg Lys Lys
2120                2125                2130

Ser Leu Ser Glu Lys Val Gln Leu Ser Glu Ser Ser Val Thr Leu
2135                2140                2145

Ser Pro Val Asp Ser Leu Glu Ser Pro His Thr Tyr Val Ser Asp
2150                2155                2160

Thr Thr Ser Ser Pro Met Ile Thr Ser Pro Gly Ile Leu Gln Ala
2165                2170                2175
```

-continued

```
Ser Pro Asn Pro Met Leu Ala Thr Ala Ala Pro Pro Ala Pro Val
    2180                2185                2190

His Ala Gln His Ala Leu Ser Phe Ser Asn Leu His Glu Met Gln
    2195                2200                2205

Pro Leu Ala His Gly Ala Ser Thr Val Leu Pro Ser Val Ser Gln
    2210                2215                2220

Leu Leu Ser His His His Ile Val Ser Pro Gly Ser Gly Ser Ala
    2225                2230                2235

Gly Ser Leu Ser Arg Leu His Pro Val Pro Val Pro Ala Asp Trp
    2240                2245                2250

Met Asn Arg Met Glu Val Asn Glu Thr Gln Tyr Asn Glu Met Phe
    2255                2260                2265

Gly Met Val Leu Ala Pro Ala Glu Gly Thr His Pro Gly Ile Ala
    2270                2275                2280

Pro Gln Ser Arg Pro Pro Glu Gly Lys His Ile Thr Thr Pro Arg
    2285                2290                2295

Glu Pro Leu Pro Pro Ile Val Thr Phe Gln Leu Ile Pro Lys Gly
    2300                2305                2310

Ser Ile Ala Gln Pro Ala Gly Ala Pro Gln Pro Gln Ser Thr Cys
    2315                2320                2325

Pro Pro Ala Val Ala Gly Pro Leu Pro Thr Met Tyr Gln Ile Pro
    2330                2335                2340

Glu Met Ala Arg Leu Pro Ser Val Ala Phe Pro Thr Ala Met Met
    2345                2350                2355

Pro Gln Gln Asp Gly Gln Val Ala Gln Thr Ile Leu Pro Ala Tyr
    2360                2365                2370

His Pro Phe Pro Ala Ser Val Gly Lys Tyr Pro Thr Pro Pro Ser
    2375                2380                2385

Gln His Ser Tyr Ala Ser Ser Asn Ala Ala Glu Arg Thr Pro Ser
    2390                2395                2400

His Ser Gly His Leu Gln Gly Glu His Pro Tyr Leu Thr Pro Ser
    2405                2410                2415

Pro Glu Ser Pro Asp Gln Trp Ser Ser Ser Ser Pro His Ser Ala
    2420                2425                2430

Ser Asp Trp Ser Asp Val Thr Thr Ser Pro Thr Pro Gly Gly Ala
    2435                2440                2445

Gly Gly Gly Gln Arg Gly Pro Gly Thr His Met Ser Glu Pro Pro
    2450                2455                2460

His Asn Asn Met Gln Val Tyr Ala
    2465                2470
```

In one embodiment of the present invention, the agonist antibody binds specifically to Notch 1 and/or Notch 2 receptors without exhibiting any substantial binding activity to any other Notch receptors. Suitable Notch agonist antibodies and methods of making the same are described herein and in Haraguchi et al., "Notch Activation Induces the Generation of Functional NK Cells from Human Cord Blood CD34-Positive Cells Devoid of IL-15," *J. Immunol.* 182 (10): 6168-78 (2009) (disclosing the Notch 2 agonist antibody, MHN2-25), Sugimoto et al., "Notch 2 Signaling is Required for Potent Antitumor Immunity In Vivo," *J. Immunol.* 184(9):4673-78 (2010) (disclosing the Notch 2 agonist antibody, HMN2-29), Kijima et al., "Dendritic Cell-Mediated NK Cell Activation is Controlled by Jagged2-Notch Interaction," *Proc. Nat'l Acad. Sci. U.S.A.* 105(19):7010-7015 (2008) (disclosing the Notch 2 agonist antibody, HMN2-29), Li et al., "Modulation of Notch Signaling by Antibodies Specific for the Extracellular Negative Regulatory Region of NOTCH3," *J. Biol. Chem.* 283(12):8046-54 (2008), Conboy et al., "Notch-Mediated Restoration of Regenerative Potential to Aged Muscle," *Science* 302:1575-1577 (2003). and U.S. Pat. No. 6,689,744 to Gao et al., which are hereby incorporated by reference in their entirety. Haraguchi et al., "Notch Activation Induces the Generation of Functional NK Cells from Human Cord Blood CD34-Positive Cells Devoid of IL-15," *J. Immunol.* 182(10): 6168-78 (2009), which is hereby incorporated by reference in its entirety, describes a human Notch 2 receptor agonist antibody that is suitable for use in the present invention. Antibody fragments corresponding to the binding regions of this human Notch 2 receptor agonist antibody are also suitable for use in the methods of the present invention.

As used herein, the term "antibody" is meant to include intact immunoglobulins derived from natural sources or from recombinant sources, as well as immunoreactive portions (i.e. antigen binding portions) of intact immunoglobulins. The antibodies of the present invention may exist in a variety of forms including, for example, polyclonal antibodies, monoclonal antibodies, intracellular antibodies, antibody fragments (e.g. Fv, Fab and F(ab)$_2$), single chain antibodies (scFv), single-domain antibodies, chimeric antibodies and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli*," *Proc Natl Acad Sci USA* 85:5879-5883 (1988); Bird et al, "Single-Chain Antigen-Binding Proteins," *Science* 242:423-426 (1988), which are hereby incorporated by reference in their entirety).

Naturally occurring antibodies typically have two identical heavy chains and two identical light chains, with each light chain covalently linked to a heavy chain by an interchain disulfide bond and multiple disulfide bonds further link the two heavy chains to one another. Individual chains can fold into domains having similar sizes (110-125 amino acids) and structures, but different functions. The light chain can comprise one variable domain (VL) and/or one constant domain (CL). The heavy chain can also comprise one variable domain (VH) and/or, depending on the class or isotype of antibody, three or four constant domains (CHL CH2, CH3 and CH4). In humans, the isotypes are IgA, IgD, IgE, IgG, and IgM, with IgA and IgG further subdivided into subclasses or subtypes (IgA1-2 and IgG1-4).

Generally, the variable domains show considerable amino acid sequence variability from one antibody to the next, particularly at the location of the antigen-binding site. Three regions, called hyper-variable or complementarity-determining regions (CDRs), are found in each of VL and VH, which are supported by less variable regions called framework variable regions. The inventive antibodies include IgG monoclonal antibodies as well as antibody fragments or engineered forms. These are, for example, Fv fragments, or proteins wherein the CDRs and/or variable domains of the exemplified antibodies are engineered as single-chain antigen-binding proteins.

The portion of an antibody consisting of the VL and VH domains is designated as an Fv (Fragment variable) and constitutes the antigen-binding site. A single chain Fv (scFv or SCA) is an antibody fragment containing a VL domain and a VH domain on one polypeptide chain, wherein the N terminus of one domain and the C terminus of the other domain are joined by a flexible linker. The peptide linkers used to produce the single chain antibodies are typically flexible peptides, selected to assure that the proper three-dimensional folding of the VL and VH domains occurs. The linker is generally 3 to 50 amino acid residues, and in some cases is shorter, e.g., about 3 to 30 amino acid residues, or 3 to 25 amino acid residues, or even 3 to 15 amino acid residues. An example of such linker peptides includes repeats of four glycine residues followed by a serine residue.

Single chain antibodies lack some or all of the constant domains of the whole antibodies from which they are derived. Therefore, they can overcome some of the problems associated with the use of whole antibodies (i.e., free of certain undesired interactions between heavy-chain constant regions and other biological molecules). Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies.

Single-domain antibodies (sdAb; nanobody) are antibody fragments consisting of a single monomeric variable antibody domain (~12-15 kDa). The sdAb are derived from the variable domain of a heavy chain (V$_H$) or the variable domain of a light chain (V$_L$). sdAbs can be naturally produced, i.e., by immunization of dromedaries, camels, llamas, alpacas or sharks (Ghahroudi et al., "Selection and Identification of Single Domain Antibody Fragments from Camel Heavy-Chain Antibodies," *FEBS Letters* 414(3): 521-526 (1997), which is hereby incorporated by reference in its entirety). Alternatively, the antibody can be produced in microorganisms or derived from conventional whole antibodies (Harmsen et al., "Properties, Production, and Applications of Camelid Single-Domain Antibody Fragments," *Appl. Microbiol. Biotechnology* 77:13-22 (2007), Holt et al., "Domain Antibodies: Proteins for Therapy," *Trends Biotech.* 21(11): 484-490 (2003), which is hereby incorporated by reference in its entirety).

Fab (Fragment, antigen binding) refers to the fragments of the antibody consisting of the VL, CL, VH, and CH1 domains. Those generated following papain digestion simply are referred to as Fab and do not retain the heavy chain hinge region. Following pepsin digestion, various Fabs retaining the heavy chain hinge are generated. Those fragments with the interchain disulfide bonds intact are referred to as F(ab')2, while a single Fab' results when the disulfide bonds are not retained. F(ab')$_2$ fragments have higher avidity for antigen that the monovalent Fab fragments.

Fc (Fragment crystallization) is the designation for the portion or fragment of an antibody that comprises paired heavy chain constant domains. In an IgG antibody, for example, the Fc comprises CH2 and CH3 domains. The Fc of an IgA or an IgM antibody further comprises a CH4 domain. The Fc is associated with Fc receptor binding, activation of complement mediated cytotoxicity and antibody-dependent cellular-cytotoxicity (ADCC). For antibodies such as IgA and IgM, which are complexes of multiple IgG-like proteins, complex formation requires Fc constant domains.

Methods for monoclonal antibody production may be carried out using techniques well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of a mammal which has been previously immunized with the antigen of interest (i.e., Notch receptor) either in vivo or in vitro.

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," *Eur J Immunol* 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability.

The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

In another embodiment of the present invention, monoclonal Notch agonist antibodies or antibody fragments can be isolated from antibody phage libraries generated using the techniques described in McCafferty et al., "Phage Antibodies: Filamentous Phage Displaying Antibody Variable Domains," Nature 348:552-554 (1990), which is hereby incorporated by reference in its entirety. Clackson et al., "Making Antibody Fragments using Phage Display Libraries," Nature 352:624-628 (1991); and Marks et al., "By-Passing Immunization. Human Antibodies from V-Gene Libraries Displayed on Phage," J. Mol. Biol. 222:581-597 (1991), which are hereby incorporated by reference in their entirety, describe the isolation of murine and human antibodies, respectively, using phage libraries. Subsequent publications describe the production of high affinity (nM range) human antibodies by chain shuffling (Marks et al., BioTechnology 10:779-783 (1992), which is hereby incorporated by reference in its entirety), as well as combinatorial infection and in vivo recombination as a strategy for constructing very large phage libraries (Waterhouse et al., Nuc. Acids. Res. 21:2265-2266 (1993), which is hereby incorporated by reference in its entirety). Thus, these techniques are viable alternatives to traditional monoclonal antibody hybridoma techniques for isolation of monoclonal antibodies.

Alternatively, monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, generate monoclonal antibodies.

The polynucleotide(s) encoding a monoclonal antibody can further be modified using recombinant DNA technology to generate alternative antibodies. For example, the constant domains of the light and heavy chains of a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

"Humanized" forms of non-human (e.g., rodent) antibodies are chimeric antibodies that contain minimal sequences derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992), which are hereby incorporated by reference in their entirety.

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers by substituting hypervariable region sequences for the corresponding sequences of a human antibody (Jones et al., Nature 321:522-525 (1986); Reichmann et al., Nature 332:323-327 (1988); Verhoeyen et al., Science 239:1534-1536 (1988), which are hereby incorporated by reference in their entirety). Accordingly, such "humanized" antibodies are chimeric antibodies wherein substantially less than an intact human variable domain has been substituted by the corresponding sequence from a non-human species (see U.S. Pat. No. 4,816,567, which is hereby incorporated by reference in its entirety). In practice, humanized antibodies are typically human antibodies in which some hypervariable region residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol. 151:2296 (1993); Chothia et al., J. Mol. Biol. 196:901 (1987), which are hereby incorporated by reference in their entirety). Another method uses a particular framework region derived from the consensus sequence of all human antibodies of a particular subgroup of light or heavy chains. The same framework may be used for several different humanized antibodies (Carter et al., Proc. Natl. Acad. Sci. USA 89:4285 (1992); Presta et al, J. Immunol. 151:2623 (1993), which are hereby incorporated by reference in their entirety).

It is further important that antibodies be humanized with retention of high binding affinity for the antigen and other favorable biological properties. To achieve this goal, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, and an analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-Notch receptor antibodies are contemplated. For example, the humanized antibody may be an antibody fragment, such as a Fab. Alternatively, the humanized antibody may be an intact antibody, such as an intact IgG1 antibody.

As an alternative to humanization, human antibodies can be generated. For example, one can produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA* 90:2551 (1993); Jakobovits et al., *Nature* 362:255-258 (1993); U.S. Pat. No. 5,545,806 to Lonberg et al, U.S. Pat. No. 5,569,825 to Lonberg et al, and U.S. Pat. No. 5,545,807 to Surani et al, which are hereby incorporated by reference in their entirety.

Alternatively, phage display technology (McCafferty et al., *Nature* 348:552-553 (1990), which is hereby incorporated by reference in its entirety) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, see e.g., Johnson and Chiswell, *Current Opinion in Structural Biology* 3:564-571 (1993), which is hereby incorporated by reference in its entirety. Several sources of V-gene segments can be used for phage display (see e.g., Clackson et al., *Nature* 352:624-628 (1991), which is hereby incorporated by reference in its entirety). A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), Griffith et al., *EMBO J.* 12:725-734 (1993), see e.g., U.S. Pat. No. 5,565,332 to Hoogenboom and U.S. Pat. No. 5,573,905 to Lerner et al., which are hereby incorporated by reference in their entirety.

Procedures for raising polyclonal antibodies are also well known. Typically, such antibodies can be raised by administering the peptide or polypeptide containing the epitope of interest subcutaneously to rabbits which have been bled to obtain pre-immune serum. The antigens can be injected in combination with an adjuvant. The rabbits are bled approximately every two weeks after the first injection and periodically boosted with the same antigen three times every six weeks. Polyclonal antibodies are recovered from the serum by affinity chromatography using the corresponding antigen to capture the antibody. This and other procedures for raising polyclonal antibodies are disclosed in Ed Harlow and David Lane, USING ANTIBODIES: A LABORATORY MANUAL (Cold Spring Harbor Laboratory Press, 1988), which is hereby incorporated by reference in its entirety.

In addition to whole antibodies, the present invention encompasses binding portions of such antibodies. Such binding portions include the monovalent Fab fragments, Fv fragments (e.g., single-chain antibody, scFv), single variable $V_H$ and $V_L$ domains, and the bivalent F(ab')$_2$ fragments, Bis-scFv, diabodies, triabodies, minibodies, etc. These antibody fragments can be made by conventional procedures, such as proteolytic fragmentation procedures, as described in James Goding, MONOCLONAL ANTIBODIES: PRINCIPLES AND PRACTICE 98-118 (Academic Press, 1983) and Ed Harlow and David Lane, ANTIBODIES: A LABORATORY MANUAL (Cold Spring Harbor Laboratory, 1988), which are hereby incorporated by reference in their entirety, or other methods known in the art.

Antibody fragments can also be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992), which is hereby incorporated by reference in its entirety). According to another approach, F(ab')$_2$ fragments can be isolated directly from recombinant host cell culture. Fab and F(ab')$_2$ fragments with increased in vivo half-life comprising a salvage receptor binding epitope residues are described in U.S. Pat. No. 5,869,046 to Presta, which is hereby incorporated by reference in its entirety. Other techniques for the production of antibody fragments will be apparent to the skilled practitioner. In other embodiments, the antibody of choice is a single chain Fv fragment (scFv) (see U.S. Pat. No. 5,571,894 to Wels and U.S. Pat. No. 5,587,458 to King et al, which are hereby incorporated by reference in their entirety). Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv.

Bispecific antibodies are antibodies that have binding specificities for at least two different epitopes. Exemplary bispecific antibodies may bind to two different epitopes of the Notch receptor protein. Alternatively, such antibodies may combine a Notch receptor binding site with a binding site for another protein, for example, an AML cell specific surface protein to target antibody binding to AML cells. Techniques for making bispecific antibodies are common in the art (Brennan et al., "Preparation of Bispecific Antibodies by Chemical Recombination of Monoclonal Immunoglobulin G1 Fragments," *Science* 229:81-3 (1985); Suresh et al, "Bispecific Monoclonal Antibodies From Hybrid Hybridomas," *Methods in Enzymol.* 121:210-28 (1986); Traunecker et al., "Bispecific Single Chain Molecules (Janusins) Target Cytotoxic Lymphocytes on HIV Infected Cells," *EMBO J.* 10:3655-3659 (1991); Shalaby et al., "Development of Humanized Bispecific Antibodies Reactive with Cytotoxic Lymphocytes and Tumor Cells Overexpressing the HER2 Protooncogene," *J. Exp. Med.* 175:217-225 (1992); Kostelny et al, "Formation of a Bispecific Antibody by the Use of Leucine Zippers," *J. Immunol.* 148: 1547-1553 (1992); Gruber et al., "Efficient Tumor Cell Lysis Mediated by a Bispecific Single Chain Antibody Expressed in *Escherichia coli,*" *J. Immunol.* 152:5368-74 (1994); and U.S. Pat. No. 5,731,168 to Carter et al., which are hereby incorporated by reference in their entirety). Generally, bispecific antibodies are secreted by triomas (i.e., lymphoma cells fuse to a hybridoma) and hybrid hybridomas. The supernatants of triomas and hybrid hybridomas can be assayed for bispecific antibody production using a suitable assay (e.g., ELISA), and bispecific antibodies can be purified using conventional methods. These antibodies can then be humanized according to methods known in the art. Humanized bispecific antibodies or a bivalent antigen-binding fragment of the bispecific antibody having binding specificity for Notch receptor protein and an antigen expressed on a target AML or other cancer cell, provides a cell-specific targeting approach.

Techniques for screening Notch agonist antibodies with the desired biological activity are known in the art. The growth inhibitory effects of an anti-Notch receptor agonist antibody of the invention may be assessed by methods known in the art, e.g., using cells which express Notch receptor either endogenously or following transfection with the Notch receptor gene. For example, AML cells and cell lines may be treated with an anti-Notch receptor monoclonal antibody of the invention at various concentrations for a few days (e.g., 2-7 days) and stained with crystal violet or MTT or analyzed by some other calorimetric assay. Another method of measuring proliferation would be by comparing $^3$H-thymidine uptake by the cells treated in the presence or absence of an anti-Notch receptor antibody of the invention. After antibody treatment, the cells are harvested and the amount of radioactivity incorporated into the DNA is quantitated in a scintillation counter. Appropriate positive controls include treatment of a selected cell line with a growth inhibitory antibody known to inhibit growth of that cell line. Preferably, the Notch receptor agonist will inhibit cell proliferation, induce cell differentiation, or induce cell death of a Notch receptor-expressing tumor cell in vitro or in vivo by about 25-100% compared to the untreated tumor cell, more preferably, by about 30-100%, and even more preferably by about 50-100% or 70-100%, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-Notch receptor antibody at about 1 µg/kg to about 100 mg/kg body weight results in reduction in tumor size or tumor cell proliferation within about 5 days to 3 months from the first administration of the antibody, preferably within about 5 to 30 days.

Antibody modifications that enhance stability or facilitate delivery of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol.

In another embodiment of the present invention, the Notch agonist is a Notch receptor activating peptide ligand. There are five endogenous transmembrane Notch receptor ligands. Three of these ligands are from the Delta-like family, i.e., the Delta-like 1 (DLL1), DLL3, DLL4 ligands, while the other two are from the Jagged family, i.e., Jagged-1 (JAG1) and JAG2. Common structural features of all Notch ligands are the epithelial growth factor-like (EGF) repeats and the distal amino-terminal domain called DSL (Delta, Serrate, and Lag-2). The DSL domain is a region of homology common to all of the Notch ligands and involved in receptor binding (Fitzgerald and Greenwald, *Development* 121:4275-4282, 1995, which is incorporated by reference in its entirety).

Suitable Notch receptor activating peptide ligands include truncated forms of the native or natural protein ligand that lack the C-terminal transmembrane domain. In particular, suitable Notch receptor ligands comprise at least the N-terminal DSL domain and can further comprises one or more additional downstream amino acid residues (see U.S. Pat. No. 7,279,554 to Chan et al., which is hereby incorporated by reference in its entirety). The amino acid sequences of the five Notch ligands and the residues comprising the DSL domain are identified below.

The amino acid sequence of human DLL1 is shown below as SEQ ID NO: 3 (UniProt Ref. No. O00548/NCBI Ref. No. NP_005609). The DSL domain of DLL1 consists of amino acid residues 159-221 of SEQ ID NO: 3. Accordingly, a suitable Notch receptor activating peptide ligand comprises an amino acid sequence corresponding to amino acid residues 159-221 of SEQ ID NO: 3. Another suitable Notch receptor activating peptide ligand comprises an amino acid sequence corresponding to amino acid residues 177-221 of SEQ ID NO: 3.

```
Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
            35                  40                  45

Ala Gly Pro Pro Cys Ala Cys Arg Thr Phe Phe Arg Val Cys Leu
        50              55                  60

Lys His Tyr Gln Ala Ser Val Ser Pro Glu Pro Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
                100                 105                 110
```

```
Gly Phe Thr Trp Pro Gly Thr Phe Ser Leu Ile Ile Glu Ala Leu His
            115                 120                 125
Thr Asp Ser Pro Asp Leu Ala Thr Glu Asn Pro Glu Arg Leu Ile
130                 135                 140
Ser Arg Leu Ala Thr Gln Arg His Leu Thr Val Gly Glu Glu Trp Ser
145                 150                 155                 160
Gln Asp Leu His Ser Ser Gly Arg Thr Asp Leu Lys Tyr Ser Tyr Arg
                165                 170                 175
Phe Val Cys Asp Glu His Tyr Tyr Gly Glu Gly Cys Ser Val Phe Cys
            180                 185                 190
Arg Pro Arg Asp Asp Ala Phe Gly His Phe Thr Cys Gly Glu Arg Gly
        195                 200                 205
Glu Lys Val Cys Asn Pro Gly Trp Lys Gly Pro Tyr Cys Thr Glu Pro
    210                 215                 220
Ile Cys Leu Pro Gly Cys Asp Glu Gln His Gly Phe Cys Asp Lys Pro
225                 230                 235                 240
Gly Glu Cys Lys Cys Arg Val Gly Trp Gln Gly Arg Tyr Cys Asp Glu
                245                 250                 255
Cys Ile Arg Tyr Pro Gly Cys Leu His Gly Thr Cys Gln Gln Pro Trp
            260                 265                 270
Gln Cys Asn Cys Gln Glu Gly Trp Gly Gly Leu Phe Cys Asn Gln Asp
        275                 280                 285
Leu Asn Tyr Cys Thr His His Lys Pro Cys Lys Asn Gly Ala Thr Cys
    290                 295                 300
Thr Asn Thr Gly Gln Gly Ser Tyr Thr Cys Ser Cys Arg Pro Gly Tyr
305                 310                 315                 320
Thr Gly Ala Thr Cys Glu Leu Gly Ile Asp Glu Cys Asp Pro Ser Pro
                325                 330                 335
Cys Lys Asn Gly Gly Ser Cys Thr Asp Leu Glu Asn Ser Tyr Ser Cys
            340                 345                 350
Thr Cys Pro Pro Gly Phe Tyr Gly Lys Ile Cys Glu Leu Ser Ala Met
        355                 360                 365
Thr Cys Ala Asp Gly Pro Cys Phe Asn Gly Gly Arg Cys Ser Asp Ser
    370                 375                 380
Pro Asp Gly Gly Tyr Ser Cys Arg Cys Pro Val Gly Tyr Ser Gly Phe
385                 390                 395                 400
Asn Cys Glu Lys Lys Ile Asp Tyr Cys Ser Ser Pro Cys Ser Asn
                405                 410                 415
Gly Ala Lys Cys Val Asp Leu Gly Asp Ala Tyr Leu Cys Arg Cys Gln
            420                 425                 430
Ala Gly Phe Ser Gly Arg His Cys Asp Asp Asn Val Asp Asp Cys Ala
        435                 440                 445
Ser Ser Pro Cys Ala Asn Gly Gly Thr Cys Arg Asp Gly Val Asn Asp
    450                 455                 460
Phe Ser Cys Thr Cys Pro Pro Gly Tyr Thr Gly Arg Asn Cys Ser Ala
465                 470                 475                 480
Pro Val Ser Arg Cys Glu His Ala Pro Cys His Asn Gly Ala Thr Cys
                485                 490                 495
His Glu Arg Gly His Arg Tyr Val Cys Glu Cys Ala Arg Gly Tyr Gly
            500                 505                 510
Gly Pro Asn Cys Gln Phe Leu Leu Pro Glu Leu Pro Pro Gly Pro Ala
        515                 520                 525
Val Val Asp Leu Thr Glu Lys Leu Glu Gly Gln Gly Gly Pro Phe Pro
    530                 535                 540
```

```
Trp Val Ala Val Cys Ala Gly Val Ile Leu Val Leu Met Leu Leu Leu
545                 550                 555                 560

Gly Cys Ala Ala Val Val Cys Val Arg Leu Arg Leu Gln Lys His
            565                 570                 575

Arg Pro Pro Ala Asp Pro Cys Arg Gly Glu Thr Glu Thr Met Asn Asn
                580                 585                 590

Leu Ala Asn Cys Gln Arg Glu Lys Asp Ile Ser Val Ser Ile Ile Gly
            595                 600                 605

Ala Thr Gln Ile Lys Asn Thr Asn Lys Lys Ala Asp Phe His Gly Asp
            610                 615                 620

His Ser Ala Asp Lys Asn Gly Phe Lys Ala Arg Tyr Pro Ala Val Asp
625                 630                 635                 640

Tyr Asn Leu Val Gln Asp Leu Lys Gly Asp Asp Thr Ala Val Arg Asp
                645                 650                 655

Ala His Ser Lys Arg Asp Thr Lys Cys Gln Pro Gln Gly Ser Ser Gly
            660                 665                 670

Glu Glu Lys Gly Thr Pro Thr Thr Leu Arg Gly Gly Glu Ala Ser Glu
            675                 680                 685

Arg Lys Arg Pro Asp Ser Gly Cys Ser Thr Ser Lys Asp Thr Lys Tyr
690                 695                 700

Gln Ser Val Tyr Val Ile Ser Glu Glu Lys Asp Glu Cys Val Ile Ala
705                 710                 715                 720

Thr Glu Val
```

The amino acid sequence of human DLL3 is shown below as SEQ ID NO: 4 (UniProt Ref. No. Q9NYJ7/NCBI Ref. No. NP_058637). The DSL domain of DLL3 consists of amino acid residues 176-215 of SEQ ID NO: 4. Accordingly, a suitable Notch receptor activating peptide ligand comprises an amino acid sequence corresponding to amino acid residues 176-215 of SEQ ID NO: 4.

```
Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
            20                  25                  30

Gln Ile His Ser Phe Gly Pro Gly Pro Gly Pro Gly Ala Pro Arg Ser
            35                  40                  45

Pro Cys Ser Ala Arg Leu Pro Cys Arg Leu Phe Phe Arg Val Cys Leu
        50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
            115                 120                 125

Glu Glu Leu Gly Asp Gln Ile Gly Gly Pro Ala Trp Ser Leu Leu Ala
            130                 135                 140

Arg Val Ala Gly Arg Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
            195                 200                 205
```

-continued

```
Pro Leu Glu Asp Glu Cys Glu Ala Pro Leu Val Cys Arg Ala Gly Cys
    210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
                245                 250                 255

Cys Leu Ser Pro Arg Gly Pro Ser Ser Ala Thr Thr Gly Cys Leu Val
            260                 265                 270

Pro Gly Pro Gly Pro Cys Asp Gly Asn Pro Cys Ala Asn Gly Gly Ser
        275                 280                 285

Cys Ser Glu Thr Pro Arg Ser Phe Glu Cys Thr Cys Pro Arg Gly Phe
    290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Ala Asp Pro Asp Ser Ala
                325                 330                 335

Tyr Ile Cys His Cys Pro Pro Gly Phe Gln Gly Ser Asn Cys Glu Lys
            340                 345                 350

Arg Val Asp Arg Cys Ser Leu Gln Pro Cys Arg Asn Gly Gly Leu Cys
        355                 360                 365

Leu Asp Leu Gly His Ala Leu Arg Cys Arg Cys Arg Ala Gly Phe Ala
    370                 375                 380

Gly Pro Arg Cys Glu His Asp Leu Asp Cys Ala Gly Arg Ala Cys
385                 390                 395                 400

Ala Asn Gly Gly Thr Cys Val Glu Gly Gly Ala His Arg Cys Ser
                405                 410                 415

Cys Ala Leu Gly Phe Gly Arg Asp Cys Arg Glu Arg Ala Asp Pro
            420                 425                 430

Cys Ala Ala Arg Pro Cys Ala His Gly Gly Arg Cys Tyr Ala His Phe
        435                 440                 445

Ser Gly Leu Val Cys Ala Cys Ala Pro Gly Tyr Met Gly Ala Arg Cys
    450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Leu Pro Pro Ala
                485                 490                 495

Leu Gly Leu Leu Val Ala Ala Gly Val Ala Gly Ala Ala Leu Leu Leu
            500                 505                 510

Val His Val Arg Arg Arg Gly His Ser Gln Asp Ala Gly Ser Arg Leu
        515                 520                 525

Leu Ala Gly Thr Pro Glu Pro Ser Val His Ala Leu Pro Asp Ala Leu
    530                 535                 540

Asn Asn Leu Arg Thr Gln Glu Gly Ser Gly Asp Gly Pro Ser Ser Ser
545                 550                 555                 560

Val Asp Trp Asn Arg Pro Glu Asp Val Asp Pro Gln Gly Ile Tyr Val
                565                 570                 575

Ile Ser Ala Pro Ser Ile Tyr Ala Arg Glu Val Ala Thr Pro Leu Phe
            580                 585                 590

Pro Pro Leu His Thr Gly Arg Ala Gly Gln Arg Gln His Leu Leu Phe
        595                 600                 605

Pro Tyr Pro Ser Ser Ile Leu Ser Val Lys
    610                 615
```

The amino acid sequence of human DLL4 is shown below as SEQ ID NO: 5 (UniProt Ref. No. Q9NR61/NCBI Ref. No. NP_061947). The DSL domain of DLL4 consists of amino acid residues 155-217 of SEQ ID NO:5. Accordingly, a suitable Notch receptor activating peptide ligand comprises an amino acid sequence corresponding to amino acid residues 155-217 of SEQ ID NO: 5. Another suitable Notch receptor activating peptide ligand comprises an amino acid sequence corresponding to amino acid residues 173-217 of SEQ ID NO: 5.

```
Met Ala Ala Ala Ser Arg Ser Ala Ser Gly Trp Ala Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
                100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
                180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
                260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
                340                 345                 350

Gly Tyr Tyr Gly Leu His Cys Glu His Ser Thr Leu Ser Cys Ala Asp
        355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400
```

```
Lys Lys Val Asp Arg Cys Thr Ser Asn Pro Cys Ala Asn Gly Gly Gln
            405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
            435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
            515                 520                 525

Trp Val Ala Val Ser Leu Gly Val Gly Leu Ala Val Leu Leu Val Leu
            530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
            595                 600                 605

Gln Asn His Thr Leu Asp Tyr Asn Leu Ala Pro Gly Pro Leu Gly Arg
            610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
            675                 680                 685
```

The amino acid sequence of human JAG1 is shown below as SEQ ID NO: 6 (UniProt Ref. No. P78504/NCBI Ref. No. NP_000205). The DSL domain of JAG1 consists of amino acid residues 167-229 of SEQ ID NO: 6. Accordingly, a suitable Notch receptor activating peptide ligand comprises an amino acid sequence corresponding to amino acid residues 167-229 of SEQ ID NO: 6. Another suitable Notch receptor activating peptide ligand comprises an amino acid sequence corresponding to amino acid residues 185-229 of SEQ ID NO: 6.

```
Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
            35                  40                  45

Leu Gln Asn Gly Asn Cys Cys Gly Gly Ala Arg Asn Pro Gly Asp Arg
        50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95
```

-continued

```
Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525
```

-continued

```
Cys Glu Pro Asn Pro Cys Gln Asn Gly Ala Gln Cys Tyr Asn Arg Ala
            530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Asn Gly Glu Ser Phe Thr Cys
        755                 760                 765

Val Cys Lys Glu Gly Trp Glu Gly Pro Ile Cys Ala Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
        835                 840                 845

Gly His Ser Gly Ala Lys Cys Gln Glu Val Ser Gly Arg Pro Cys Ile
    850                 855                 860

Thr Met Gly Ser Val Ile Pro Asp Gly Ala Lys Trp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
        915                 920                 925

Pro Cys Thr Gly Val Gly Glu Cys Arg Ser Ser Ser Leu Gln Pro Val
    930                 935                 940

Lys Thr Lys Cys Thr Ser Asp Ser Tyr Tyr Gln Asp Asn Cys Ala Asn
945                 950                 955                 960
```

-continued

```
Ile Thr Phe Thr Phe Asn Lys Glu Met Met Ser Pro Gly Leu Thr Thr
            965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser Pro Ser Ala
            995                1000                1005

Asn Asn Glu Ile His Val Ala Ile Ser Ala Glu Asp Ile Arg Asp
        1010                1015                1020

Asp Gly Asn Pro Ile Lys Glu Ile Thr Asp Lys Ile Ile Asp Leu
        1025                1030                1035

Val Ser Lys Arg Asp Gly Asn Ser Ser Leu Ile Ala Ala Val Ala
        1040                1045                1050

Glu Val Arg Val Gln Arg Arg Pro Leu Lys Asn Arg Thr Asp Phe
        1055                1060                1065

Leu Val Pro Leu Leu Ser Ser Val Leu Thr Val Ala Trp Ile Cys
        1070                1075                1080

Cys Leu Val Thr Ala Phe Tyr Trp Cys Leu Arg Lys Arg Arg Lys
        1085                1090                1095

Pro Gly Ser His Thr His Ser Ala Ser Glu Asp Asn Thr Thr Asn
        1100                1105                1110

Asn Val Arg Glu Gln Leu Asn Gln Ile Lys Asn Pro Ile Glu Lys
        1115                1120                1125

His Gly Ala Asn Thr Val Pro Ile Lys Asp Tyr Glu Asn Lys Asn
        1130                1135                1140

Ser Lys Met Ser Lys Ile Arg Thr His Asn Ser Glu Val Glu Glu
        1145                1150                1155

Asp Asp Met Asp Lys His Gln Gln Lys Ala Arg Phe Ala Lys Gln
        1160                1165                1170

Pro Ala Tyr Thr Leu Val Asp Arg Glu Glu Lys Pro Pro Asn Gly
        1175                1180                1185

Thr Pro Thr Lys His Pro Asn Trp Thr Asn Lys Gln Asp Asn Arg
        1190                1195                1200

Asp Leu Glu Ser Ala Gln Ser Leu Asn Arg Met Glu Tyr Ile Val
        1205                1210                1215
```

The amino acid sequence of human JAG2 is shown below as SEQ ID NO: 7 (UniProt Ref. No. Q9Y219/NCBI Ref. No. NP_002217). The DSL domain of JAG2 consists of amino acid residues 178-240 of SEQ ID NO: 7. Accordingly, a suitable Notch receptor activating peptide ligand comprises an amino acid sequence corresponding to amino acid residues 178-240 of SEQ ID NO: 7. Another suitable Notch receptor activating peptide ligand comprises an amino acid sequence corresponding to amino acid residues 196-240 of SEQ ID NO: 7.

```
Met Arg Ala Gln Gly Arg Gly Arg Leu Pro Arg Leu Leu Leu Leu
1               5                   10                  15

Leu Ala Leu Trp Val Gln Ala Ala Arg Pro Met Gly Tyr Phe Glu Leu
                20                  25                  30

Gln Leu Ser Ala Leu Arg Asn Val Asn Gly Glu Leu Leu Ser Gly Ala
                35                  40                  45

Cys Cys Asp Gly Asp Gly Arg Thr Thr Arg Ala Gly Gly Cys Gly His
                50                  55                  60

Asp Glu Cys Asp Thr Tyr Val Arg Val Cys Leu Lys Glu Tyr Gln Ala
65                      70                  75                  80

Lys Val Thr Pro Thr Gly Pro Cys Ser Tyr Gly His Gly Ala Thr Pro
                        85                  90                  95

Val Leu Gly Gly Asn Ser Phe Tyr Leu Pro Pro Ala Gly Ala Ala Gly
                        100                 105                 110
```

```
Asp Arg Ala Arg Ala Arg Ala Gly Gly Asp Gln Asp Pro Gly
    115                 120                 125

Leu Val Val Ile Pro Phe Gln Phe Ala Trp Pro Arg Ser Phe Thr Leu
130                 135                 140

Ile Val Glu Ala Trp Asp Trp Asp Asn Asp Thr Thr Pro Asn Glu Glu
145                 150                 155                 160

Leu Leu Ile Glu Arg Val Ser His Ala Gly Met Ile Asn Pro Glu Asp
                165                 170                 175

Arg Trp Lys Ser Leu His Phe Ser Gly His Val Ala His Leu Glu Leu
                180                 185                 190

Gln Ile Arg Val Arg Cys Asp Glu Asn Tyr Tyr Ser Ala Thr Cys Asn
            195                 200                 205

Lys Phe Cys Arg Pro Arg Asn Asp Phe Phe Gly His Tyr Thr Cys Asp
210                 215                 220

Gln Tyr Gly Asn Lys Ala Cys Met Asp Gly Trp Met Gly Lys Glu Cys
225                 230                 235                 240

Lys Glu Ala Val Cys Lys Gln Gly Cys Asn Leu Leu His Gly Gly Cys
                245                 250                 255

Thr Val Pro Gly Glu Cys Arg Cys Ser Tyr Gly Trp Gln Gly Arg Phe
            260                 265                 270

Cys Asp Glu Cys Val Pro Tyr Pro Gly Cys Val His Gly Ser Cys Val
        275                 280                 285

Glu Pro Trp Gln Cys Asn Cys Glu Thr Asn Trp Gly Gly Leu Leu Cys
    290                 295                 300

Asp Lys Asp Leu Asn Tyr Cys Gly Ser His His Pro Cys Thr Asn Gly
305                 310                 315                 320

Gly Thr Cys Ile Asn Ala Glu Pro Asp Gln Tyr Arg Cys Thr Cys Pro
                325                 330                 335

Asp Gly Tyr Ser Gly Arg Asn Cys Glu Lys Ala Glu His Ala Cys Thr
            340                 345                 350

Ser Asn Pro Cys Ala Asn Gly Gly Ser Cys His Glu Val Pro Ser Gly
        355                 360                 365

Phe Glu Cys His Cys Pro Ser Gly Trp Ser Gly Pro Thr Cys Ala Leu
    370                 375                 380

Asp Ile Asp Glu Cys Ala Ser Asn Pro Cys Ala Ala Gly Gly Thr Cys
385                 390                 395                 400

Val Asp Gln Val Asp Gly Phe Glu Cys Ile Cys Pro Glu Gln Trp Val
                405                 410                 415

Gly Ala Thr Cys Gln Leu Asp Ala Asn Glu Cys Glu Gly Lys Pro Cys
            420                 425                 430

Leu Asn Ala Phe Ser Cys Lys Asn Leu Ile Gly Gly Tyr Tyr Cys Asp
        435                 440                 445

Cys Ile Pro Gly Trp Lys Gly Ile Asn Cys His Ile Asn Val Asn Asp
    450                 455                 460

Cys Arg Gly Gln Cys Gln His Gly Gly Thr Cys Lys Asp Leu Val Asn
465                 470                 475                 480

Gly Tyr Gln Cys Val Cys Pro Arg Gly Phe Gly Gly Arg His Cys Glu
                485                 490                 495

Leu Glu Arg Asp Glu Cys Ala Ser Ser Pro Cys His Ser Gly Gly Leu
            500                 505                 510

Cys Glu Asp Leu Ala Asp Gly Phe His Cys His Cys Pro Gln Gly Phe
        515                 520                 525

Ser Gly Pro Leu Cys Glu Val Asp Val Asp Leu Cys Glu Pro Ser Pro
    530                 535                 540
```

-continued

```
Cys Arg Asn Gly Ala Arg Cys Tyr Asn Leu Glu Gly Asp Tyr Tyr Cys
545                 550                 555                 560

Ala Cys Pro Asp Asp Phe Gly Gly Lys Asn Cys Ser Val Pro Arg Glu
            565                 570                 575

Pro Cys Pro Gly Gly Ala Cys Arg Val Ile Asp Gly Cys Gly Ser Asp
        580                 585                 590

Ala Gly Pro Gly Met Pro Gly Thr Ala Ala Ser Gly Val Cys Gly Pro
        595                 600                 605

His Gly Arg Cys Val Ser Gln Pro Gly Gly Asn Phe Ser Cys Ile Cys
        610                 615                 620

Asp Ser Gly Phe Thr Gly Thr Tyr Cys His Glu Asn Ile Asp Asp Cys
625                 630                 635                 640

Leu Gly Gln Pro Cys Arg Asn Gly Gly Thr Cys Ile Asp Glu Val Asp
            645                 650                 655

Ala Phe Arg Cys Phe Cys Pro Ser Gly Trp Glu Gly Glu Leu Cys Asp
            660                 665                 670

Thr Asn Pro Asn Asp Cys Leu Pro Asp Pro Cys His Ser Arg Gly Arg
            675                 680                 685

Cys Tyr Asp Leu Val Asn Asp Phe Tyr Cys Ala Cys Asp Asp Gly Trp
690                 695                 700

Lys Gly Lys Thr Cys His Ser Arg Glu Phe Gln Cys Asp Ala Tyr Thr
705                 710                 715                 720

Cys Ser Asn Gly Gly Thr Cys Tyr Asp Ser Gly Asp Thr Phe Arg Cys
            725                 730                 735

Ala Cys Pro Pro Gly Trp Lys Gly Ser Thr Cys Ala Val Ala Lys Asn
            740                 745                 750

Ser Ser Cys Leu Pro Asn Pro Cys Val Asn Gly Gly Thr Cys Val Gly
            755                 760                 765

Ser Gly Ala Ser Phe Ser Cys Ile Cys Arg Asp Gly Trp Glu Gly Arg
        770                 775                 780

Thr Cys Thr His Asn Thr Asn Asp Cys Asn Pro Leu Pro Cys Tyr Asn
785                 790                 795                 800

Gly Gly Ile Cys Val Asp Gly Val Asn Trp Phe Arg Cys Glu Cys Ala
            805                 810                 815

Pro Gly Phe Ala Gly Pro Asp Cys Arg Ile Asn Ile Asp Glu Cys Gln
        820                 825                 830

Ser Ser Pro Cys Ala Tyr Gly Ala Thr Cys Val Asp Glu Ile Asn Gly
        835                 840                 845

Tyr Arg Cys Ser Cys Pro Pro Gly Arg Ala Gly Pro Arg Cys Gln Glu
    850                 855                 860

Val Ile Gly Phe Gly Arg Ser Cys Trp Ser Arg Gly Thr Pro Phe Pro
865                 870                 875                 880

His Gly Ser Ser Trp Val Glu Asp Cys Asn Ser Cys Arg Cys Leu Asp
            885                 890                 895

Gly Arg Arg Asp Cys Ser Lys Val Trp Cys Gly Trp Lys Pro Cys Leu
            900                 905                 910

Leu Ala Gly Gln Pro Glu Ala Leu Ser Ala Gln Cys Pro Leu Gly Gln
        915                 920                 925

Arg Cys Leu Glu Lys Ala Pro Gly Gln Cys Leu Arg Pro Pro Cys Glu
    930                 935                 940

Ala Trp Gly Glu Cys Gly Ala Glu Glu Pro Pro Ser Thr Pro Cys Leu
945                 950                 955                 960

Pro Arg Ser Gly His Leu Asp Asn Asn Cys Ala Arg Leu Thr Leu His
            965                 970                 975
```

```
Phe Asn Arg Asp His Val Pro Gln Gly Thr Val Gly Ala Ile Cys
            980                 985                 990
Ser Gly Ile Arg Ser Leu Pro Ala Thr Arg Ala Val Ala Arg Asp Arg
            995                1000                1005
Leu Leu Val Leu Leu Cys Asp Arg Ala Ser Ser Gly Ala Ser Ala
           1010                1015                1020
Val Glu Val Ala Val Ser Phe Ser Pro Ala Arg Asp Leu Pro Asp
           1025                1030                1035
Ser Ser Leu Ile Gln Gly Ala Ala His Ala Ile Val Ala Ala Ile
           1040                1045                1050
Thr Gln Arg Gly Asn Ser Ser Leu Leu Leu Ala Val Thr Glu Val
           1055                1060                1065
Lys Val Glu Thr Val Val Thr Gly Gly Ser Ser Thr Gly Leu Leu
           1070                1075                1080
Val Pro Val Leu Cys Gly Ala Phe Ser Val Leu Trp Leu Ala Cys
           1085                1090                1095
Val Val Leu Cys Val Trp Trp Thr Arg Lys Arg Arg Lys Glu Arg
           1100                1105                1110
Glu Arg Ser Arg Leu Pro Arg Glu Glu Ser Ala Asn Asn Gln Trp
           1115                1120                1125
Ala Pro Leu Asn Pro Ile Arg Asn Pro Ile Glu Arg Pro Gly Gly
           1130                1135                1140
His Lys Asp Val Leu Tyr Gln Cys Lys Asn Phe Thr Pro Pro Pro
           1145                1150                1155
Arg Arg Ala Asp Glu Ala Leu Pro Gly Pro Ala Gly His Ala Ala
           1160                1165                1170
Val Arg Glu Asp Glu Glu Asp Glu Asp Leu Gly Arg Gly Glu Glu
           1175                1180                1185
Asp Ser Leu Glu Ala Glu Lys Phe Leu Ser His Lys Phe Thr Lys
           1190                1195                1200
Asp Pro Gly Arg Ser Pro Gly Arg Pro Ala His Trp Ala Ser Gly
           1205                1210                1215
Pro Lys Val Asp Asn Arg Ala Val Arg Ser Ile Asn Glu Ala Arg
           1220                1225                1230
Tyr Ala Gly Lys Glu
           1235
```

Homologous Notch receptor activating peptide ligands can be derived from mammals and non-mammals other than those described above and are preferably characterized by an amino acid sequence identity of at least about 60 percent, more preferably at least about 70 percent or 80 percent, most preferably at least about 85 percent or 90 percent or 95 percent as compared to human Notch receptor ligands of SEQ ID NOs: 3-7, and in particular as compared to the DSL domains of the Notch receptor ligands of SEQ ID NOs: 3-7. The Notch receptor activating peptide ligands of the present invention may contain one or more amino acid variations from the native sequences of SEQ ID NOs: 3-7 provided above. These amino acid changes are selected to, for example, confer upon the ligand the (i) ability to constitutively activate the Notch receptor, (ii) greater binding, (iii) longer half-life, and/or (iv) greater stability in vivo.

Notch ligand variants can be naturally or non-naturally occurring. Naturally occurring variants are found in humans or other species and comprise amino acid sequences which are substantially identical to the amino acid sequences shown in SEQ ID NOs: 3-7. Non-naturally occurring variants retain substantially the same biological activities as naturally occurring protein variants. Preferably, naturally or non-naturally occurring variants have amino acid sequences which are at least 85%, 90%, or 95% identical to the amino acid sequences shown in SEQ ID Nos: 3-7. More preferably, the molecules are at least 98% or 99% identical. Guidance in determining which amino acid residues can be substituted, inserted, or deleted without abolishing biological or immunological activity can be found using computer programs well known in the art, such as DNASTAR software. Preferably, amino acid changes are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Suitable Notch activating receptor ligands can also be modified using one or more additional or alternative strategies for prolonging the in vivo half-life of the peptide ligand. One such strategy involves the generation of D-peptide Notch receptor ligands, which consist of unnatural amino acids that are not cleaved by endogenous proteases. Alternatively, the Notch receptor ligand or fragment thereof is fused to a peptide partner that confers a longer half-life to the Notch ligand upon in vivo administration. Suitable fusion partners include, without limitation, immunoglobulins (e.g., the Fc portion of an IgG as described herein, see also, Amsen et al., "The Different Faces of Notch in T-helper-cell Differentiation," *Nature Rev. Immun.* 9(2):116-124 (2009), Elyaman et al., "Jagged1 and Delta1 Differentially Regulate the Outcome of Experimental Autoimmune Encephalomyelitis," *J. Immunol.* 179(9):5990-5998 (2007), and Shimizu et al., "Physical Interaction of Delta1, Jagged1, and Jagged2 with Notch1 and Notch3 Receptors," *Biophys. Res. Commun.* 276: 385-389 (2000), which are hereby incorporated by reference in their entirety), polyethylene glycol (PEG), human serum albumin (HAS) (linked directly or by addition of the albumin binding domain of streptococcal protein G), fetuin, or a fragment of any of these. Methods of conjugating proteins or peptides to polymers to enhance stability for therapeutic administration are described in U.S. Pat. No. 5,681,811 to Ekwuribe, which is hereby incorporated by reference in its entirety. Nucleic acid conjugates are described in U.S. Pat. No. 6,528,631 to Cook et al., U.S. Pat. No. 6,335,434 to Guzaev et al., U.S. Pat. No. 6,235,886 to Manoharan et al., U.S. Pat. No. 6,153,737 to Manoharan et al., U.S. Pat. No. 5,214,136 to Lin et al., and U.S. Pat. No. 5,138,045 to Cook et al., which are hereby incorporated by reference in their entirety.

The efficacy of Notch receptor agonist ligand induced signaling in vivo may be low in solution. A suitable approach for increasing efficacy is through higher valency interactions. Various possible multimerization platforms amenable to therapeutic applications exist and are known in the art. Multimerization can increase peptide stability, result in a higher binding strength due to multiple valencies in the molecule, improve pharmacokinetic properties, and also offer the possibility to combine several functional domains into one molecule.

One approach for multimerization involves linkage of Notch activating ligands to an IgG-like molecule. For example, Allaway et al., "Expression and Characterization of CD4-IgG2, a novel heterotetramer that Neutralizes Primary HIV Type I Isolates," *AIDS Res. Hum. Retroviruses* 11:53 (1995), which is hereby incorporated by reference in its entirety, describes the tetramerization of peptide domains by substitution of the variable domains of the light and heavy chains of an IgG molecule. Another straight-forward approach involves the use of the CovX-body technology (Pfizer, New York, N.Y.) to fuse bioactive Notch peptides to IgG molecules as described by Doppalapudi et al., "Chemical Generation of Bispecific Antibodies," *Proc. Nat'l Acad. Sci. U.S.A.*, 107(52): 22611-22616 (2010); Roberts et al., "Kappa Agonist CovX-Bodies," *Bioorg. Med. Chem. Lett.* 22(12):4173-78 (2012); and WO/2012/007896 to Bhat et al., which are hereby incorporated by reference in their entirety.

Another approach for multimerization is based on the human complement 4b binding protein (C4bp). The human plasma protein C4bp has a spider-like structure consisting of seven α-chains and one β-chain. The α chain contains a domain of 60 amino acids at its C-terminus that is responsible for multimerization induced by the formation of intermolecular cysteine bridges between the individual domains. By inserting the nucleotide sequence encoding the Notch activating ligand between a signal peptide and the multimerising domain of the α-chain of C4bp, therapeutic multimeric proteins can be produced (Dervillez et al., "Stable Expression of Soluble Therapeutic Peptides in Eukaryotic Cells by Multimerisation: Application to the HIV-1 Fusion Inhibitory Peptide C46," *ChemMed Chem* 1(3):339-339 (2006), which is hereby incorporated by reference in its entirety).

The Notch receptor ligand agonists of the present invention may be prepared using standard methods of synthesis known in the art, including solid phase peptide synthesis (Fmoc or Boc strategies) or solution phase peptide synthesis. Alternatively, Notch receptor ligands of the present invention may be prepared using recombinant expression systems.

For recombinant protein or peptide synthesis, subclones of a gene or gene fragment encoding a Notch receptor ligand or truncated form of the receptor ligand are used to produce a recombinant ligand using conventional molecular genetic manipulation for subcloning gene fragments, such as described by Joseph Sambrook et al., MOLECULAR CLONING: A LABORATORY MANUAL (Cold Springs Harbor 1989) and Ausubel et al., CURRENT PROTOCOLS IN MOLECULAR BIOLOGY (John Wiley & Sons 1999), each of which is hereby incorporated by reference in its entirety. The subclones then are expressed in vitro or in vivo in bacterial cells to yield a smaller protein or polypeptide that can be tested for a particular activity, e.g., inducing Notch receptor mediated signaling.

In another approach, based on knowledge of the primary structure of the protein, fragments of a Notch ligand gene may be synthesized using PCR with specific sets of primers chosen to represent particular portions of the protein (Erlich et al., "Recent Advances in the Polymerase Chain Reaction," *Science* 252:1643-51 (1991), which is hereby incorporated by reference in its entirety). These can then be cloned into an appropriate vector for expression of a truncated Notch ligand protein or polypeptide from bacterial cells.

Therapeutic formulations of the Notch receptor agonist antibodies and ligands used in accordance with the present invention are prepared for storage by mixing an antibody or ligand having the desired degree of purity with optional pharmaceutically acceptable carriers, excipients or stabilizers (*Remington's Pharmaceutical Sciences* 16th edition, Osol, A Ed. (1980), which is hereby incorporated by reference in its entirety), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride, benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEENT™, PLURONICS™ or polyethylene glycol (PEG).

The formulation herein may also contain more than one active compound as necessary for the particular indication being treated, preferably those with complementary activities that do not adversely affect each other. For example, in addition to the Notch receptor agonist antibody, it may be desirable to include in the one formulation, an additional antibody, e.g. a second Notch receptor agonist antibody which binds a different epitope on Notch receptor, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, a hypomethylating agent, a FLT3 inhibitor, a farnesyltransferase inhibitor, or any combination thereof. Such, molecules are suitably present in combination in amounts that are effective for the purpose intended.

The Notch receptor agonist therapeutic formulations of the present invention may be entrapped in microcapsules prepared, for example, by coacervation techniques or by interfacial polymerization (for example, hydroxymethylcellulose or gelatin-microcapsules and poly-(methylmethacylate) microcapsules, respectively) to facilitate delivery. Alternatively, the therapeutic formulations of the present invention may be present in colloidal drug delivery systems, for example, liposomes, albumin microspheres, microemulsions, nano-particles and nanocapsules, or in macroemulsions. Such techniques are disclosed in Remington's *Pharmaceutical Sciences,* 16th edition, Oslo, A., Ed., (1980), which is hereby incorporated by reference in its entirety.

The Notch receptor agonists can also be formulated in sustained-release preparations for in vivo administration. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919, which is hereby incorporated by reference in its entirety), copolymers of L-glutamic acid and ethyl-L-glutamate, non-degradable ethylene-vinyl acetate, degradable lactic acid-glycolic acid copolymers such as the LUPRON DEPO™ (injectable microspheres composed of lactic acid-glycolic acid copolymer and leuprolide acetate), and poly-D-(-)-3-hydroxybutyric acid.

Another aspect of the present invention is directed to a method of treating acute myeloid leukemia in a subject. This method involves selecting a subject having acute myeloid leukemia and administering to the selected subject, a Notch receptor agonist under conditions effective to treat the acute myeloid leukemia in the subject.

While Notch signaling pathway activation is known to contribute to the pathogenesis of a spectrum of human malignancies, including T cell leukemia, as shown herein, the Notch pathway acts as a tumor suppressor in acute myeloid leukemia. The Notch pathway also acts as a tumor suppressor in myeloproliferative neoplasms such as chronic myelomonocytic leukemia and B-cell acute lymphoblastic leukemia, and in several solid tumors, such as head and neck squamous cell carcinoma and hepatocellular carcinoma. Accordingly, a Notch receptor agonist, in particular Notch receptor antibody agonists, can be used to treat any one of these aforementioned conditions.

As described supra, suitable Notch receptor agonists include Notch agonist antibodies, Notch activating receptor ligands, and small molecule receptor agonists. In one embodiment of the present invention, the Notch receptor agonist is a Notch 2 receptor agonist, a Notch 1 receptor agonist or a combination thereof.

As used herein, "subject" refers to any animal having or at risk of having acute myeloid leukemia or any other condition described infra, which is amenable to treatment in accordance with the methods of the present invention. Preferably, the subject is a mammal. Exemplary mammalian subjects include, without limitation, humans, non-human primates, dogs, cats, rodents (e.g., mouse, rat, guinea pig), horses, cattle and cows, sheep, and pigs.

In accordance with this aspect of the present invention, the Notch receptor agonist may be administered in combination with another acute myeloid leukemia therapy, such as chemotherapy, stem cell transplantation therapy, a hypomethylating agent therapy, a FLT3 inhibitor therapy, a farnesyltransferase inhibitor therapy, a topoisomerase II inhibitor therapy, P-glycoprotein modulator therapy, and combinations thereof.

Chemotherapeutic agents typically used in the treatment of AML include, without limitation, cytosine arabinoside, anthracycline, anthracenedione, daunorubicin, adriamycin, idarubicin, mitoxantrone, and combinations thereof. New chemotherapeutics used in the treatment of AML include ara-C conjugated to the lipid moiety elaidic acid, and CPX-351, which is a 5:1 ratio of cytarabine to daunorubicin within a liposomal carrier. Accordingly, a Notch receptor agonist can be administered in combination with any one or more of these or other chemotherapeutic agents to treat AML or other cancerous condition that would benefit from Notch signaling. The Notch agonist can be administered prior to, subsequent with, or after administration of the chemotherapeutic agent.

Hypomethylating agents typically used for the treatment of AML include, without limitation, 5-aza-cytidine, 2' deoxyazacitidine, or a combination thereof. Accordingly, a Notch receptor agonist can be administered in combination with any one or more of these or other hypomethylating agents to treat AML. The Notch agonist can be administered prior to, subsequent with, or after administration of the hypomethylating agent.

FLT3 inhibitors used for the treatment of AML include, without limitation, Semexanib (SU5416), Sunitinib (SU11248), Midostaurin (PKC412), Lestautinib (CEP-701), Tandutinib (MLN518), CHIR-258, Sorafenib (BAY-43-9006) and KW-2449. Accordingly, a Notch receptor agonist can be administered in combination with any one or more of these or other FLT3 inhibitors to treat AML. The Notch agonist can be administered prior to, subsequent with, or after administration of the FLT3 inhibitory agent Farnesyltransferase inhibitors used for the treatment of AML include, without limitation tipifarnib (R115777, Zarnestra), lonafarnib (SCH66336, Sarasar™) and BMS-214662. Accordingly, a Notch receptor agonist can be administered in combination with any one or more of these or other Farnesyltransferase inhibitors to treat AML. The Notch agonist can be administered prior to, subsequent with, or after administration of the Farnesyltransferase inhibitor.

Topoisomerase II inhibitors used for the treatment of AML include, without limitation, the epipodophyllotoxins etoposide and teniposide, and the anthracyclines doxorubicin and 4-epi-doxorubicin. Accordingly, a Notch receptor agonist can be administered in combination with any one or more of these or other Topoisomerase II inhibitors to treat AML. The Notch agonist can be administered prior to, subsequent with, or after administration of the topoisomerase II inhibitor.

P-glycoprotein modulators used for the treatment of AML include, without limitation zosuquidar trihydrochloride (Z.3HCL), vanadate, and verapamil. Accordingly, a Notch receptor agonist can be administered in combination with any one or more of these or other P-glycoprotein modulators to treat AML. The Notch agonist can be administered prior to, subsequent with, or after administration of the P-glycoprotein modulator.

Another aspect of the present invention is directed to a method of inhibiting the development of acute myeloid leukemia relapse disease in a subject. This method involves selecting a subject having had acute myeloid leukemia and administering, to the selected subject, a Notch receptor agonist under conditions effective to inhibit the development of acute myeloid leukemia relapse disease in the subject.

While current AML therapeutics aim to achieve complete remission of the disease, the concept that a small number of undetectable leukemic cells are "left over" after treatment and will eventually proliferate and cause disease relapse is intuitive and well supported by laboratory data (Roboz, G., "Novel Approaches to the Treatment of Acute Myeloid Leukemia," Hematology 1:43-49 (2011), which is hereby incorporated by reference in its entirety). Because the leukemia initiating cell population is capable of recapitulating disease, these cells are believed to play a dominant role in the development of disease relapse and, therefore, are a primary target for preventing and treating relapse disease in AML. As demonstrated herein, Notch signaling induces cell differentiation and cell death in AML leukemic initiating cells, rendering Notch agonists a particularly suitable therapeutic approach for inhibiting and treating relapse disease In one embodiment of this aspect of the present invention, the selected subject is one that is in complete remission of AML. Complete remission is defined by the following criteria: (i) normal values for absolute neutrophil count and platelet count, and independence from red cell transfusion; (ii) a bone marrow biopsy that reveals no clusters or collections of blast cells and extramedullary leukemia is absent; (iii) a bone marrow aspiration reveals normal maturation of all cellular components (i.e., erythrocytic, granulocytic, and megakaryocytic); (iv) less than 5% blast cells are present in the bone marrow, and none have a leukemic phenotype; (v) absence of previously detected clonal cytogenetic abnormality confirms the morphologic diagnosis of complete remission. In another embodiment of this aspect of the present invention, the subject is one that has complete remission with insufficient hematological recovery. Notch agonism therapy is administered to a subject in complete remission as defined by the criteria above and repeated periodically as needed to prevent relapse disease.

In another embodiment of this aspect of the present invention, the subject selected for Notch receptor agonist treatment is a subject that has a measurable amount of minimal residual disease (MRD). Postremission MRD can be detected and assessed using PCR and sensitive flow cytometry techniques. Preferably, Notch agonism therapy is administered prior to or at the very earliest detection of MRD and repeated periodically as needed to prevent and/or treat relapse disease.

In the context of treating relapse disease, the Notch receptor agonist can be administered in combination with one more other acute myeloid leukemia therapies, e.g., chemotherapy, stem cell transplantation therapy, a hypomethylating agent therapy, a FLT3 inhibitor therapy, a farnesyltransferase inhibitor therapy, a topoisomerase II inhibitor therapy, P-glycoprotein modulator therapy, and combinations thereof as described above.

In accordance with this and all aspects of the present invention, the dosage and mode of administration of the Notch receptor agonist will be chosen by the physician according to known criteria. The appropriate dosage of Notch agonist antibody will depend on the type of disease to be treated (i.e., AML or other cancerous condition), as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Preferably, the antibody is administered by intravenous infusion or by subcutaneous injections. Depending on the type and severity of the disease, about 1 µg/kg to about 50 mg/kg body weight (e.g. about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the Notch receptor agonist antibody. However, other dosage regimens that may be useful are also contemplated. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

The Notch receptor agonists of the present invention, i.e., Notch antibodies and/or ligands are administered to the subject, in accordance with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred. As noted above, other therapeutic regimens may be combined with the administration of the Notch receptor agonist. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

EXAMPLES

The following examples are provided to illustrate embodiments of the present invention but they are by no means intended to limit its scope Material and Methods for Examples 1-7

Animals

All animals were kept in NYU Specific Pathogen Free facility. Genotyping of Ncstn$^{f/f}$, Tet2$^{f/f}$ and EF1a$^{wt/lslN1-IC}$ was performed as previously described (Klinakis et al., "A Novel Tumour-Suppressor Function for the Notch Pathway in Myeloid Leukaemia," *Nature* 473:230-233 (2011); Moran-Crusio et al., "Tet2 Loss Leads to Increased Hematopoietic Stem Cell Self-Renewal and Myeloid Transformation," *Cancer Cell* 20:11-24 (2011), which are hereby incorporated by reference in their entirety). ROSA26-ICN (1-4) mice were generated by insertion of a loxP flanked splice acceptor NEO-ATG cassette with two polyA sites followed by ICN2 into the ROSA26 locus, allowing the ROSA26 promoter to drive expression of the NEO-ATG cassette. Cre recombinase mediated excision of NEO-ATG results in use of the splice acceptor in the ICN2 cassette and irreversible expression of the transgene. Ncstn$^{f/f}$ and Tet2$^{f/f}$ mice were crossed to the Vav1-cre deleter strain (Stadtfeld and Graf, "Assessing the Role of Hematopoietic Plasticity for Endothelial and Hepatocyte Development by Non-Invasive Lineage Tracing," *Development* 132:203-213 (2005), which is hereby incorporated by reference in its entirety). EF1a$^{wt/lslN1-IC}$ mice were crossed to the tamoxifen inducible ROSA26-CreERT2 (gift from D. Littman, NYU School of Medicine). Tamoxifen (Sigma Aldrich) was solubilized in corn oil (Sigma Aldrich) at a concentration of 20 mg/mL and injected intraperitoneally at 0.2 mg/g body weight. All animal experiments were done in accordance to the guidelines of the NYU School of Medicine IACUC.

Antibodies and FACS Analysis.

Antibody staining and FACS analysis was performed as previously described (Klinakis et al., "A Novel Tumour-Suppressor Function for the Notch Pathway in Myeloid Leukaemia," *Nature* 473:230-233 (2011), which is hereby incorporated by reference in its entirety). To analyze and isolate AML LICs and GMPs, total bone marrow cells were recovered from flushing the tibias and femurs of mice with PBS supplemented with 3% FBS and 1% Penicillin/Streptomycin. Bone marrow mononuclear cells were then stained with a lineage cocktail comprised of antibodies targeting CD4, CD8, B220, NK1.1, Gr-1, CD11b, Ter119, and IL-7Rα. Cells were also stained with antibodies against cKit, Sca-1, FcγRII/III, and CD34. Cell populations were analyzed using a FACSFortessa (Becton Dickinson) and sorted with a FACSAria instrument (Becton Dickinson). All antibodies were purchased from BD-Pharmingen or e-Bioscience. The following antibodies were also used: c-kit (2B8), Sca-1 (D7), Mac-1/CD11b (M1/70), Gr-1 (RB6-8C5), NK1.1 (PK136), Ter-119, IL7Rα(A7R34), CD34 (RAM34), FcγRII/III (2.4G2), CD4 (RM4-5), CD4 (H129.19), CD8 (53-6.7), CD45.1 (A20), CD45.2 (104), CD11c (HL3), NOTCH1 (APC conjugated, 22E5 e-Bioscience), NOTCH2 (PE conjugated, 16F11 e-Bioscience). For ChIP, antibodies were purchased from Millipore (H3K27me3) and Active Motif (H3K4me3, Ezh2). Magnetic protein G beads were purchased from Invitrogen.

RT-PCR.

Total RNA was isolated using the RNeasy Plus Mini Kit (Qiagen) and cDNA was synthesized using the SuperScript First-Strand Kit (Invitrogen). Quantitative PCR was performed using SYBR green iMaster and a LightCycler 480 (Roche) using the primers referenced in Table 1 below.

| Gene | Species | Sequence | SEQ ID NO: | Application |
|---|---|---|---|---|
| NOTCH1 | Human | Forward: CTGAAGAACGGGGCTAACAA | 8 | Expression |
|  |  | Reverse: CAGGTTGTACTCGTCCAGCA | 9 |  |
| NOTCH1 | Mouse | Forward: GGCTCCGCTGCAGACACAGG | 10 | Expression |
|  |  | Reverse: GCTCGCCGCAAGAGGCTTGA | 11 |  |
| NOTCH2 | Human | Forward: ACCAGTGTGATGAGCTGTGC | 12 | Expression |
|  |  | Reverse: AGGGTACCTTCTGCCAGGTT | 13 |  |
| NOTCH2 | Mouse | Forward: GTGCCTCCAACCCCTGTCGC | 14 | Expression |
|  |  | Reverse: ACCAACCCAGCCTGCATCGC | 15 |  |
| NOTCH3 | Human | Forward: GTAGAGGGCATGGTGGAAGA | 16 | Expression |
|  |  | Reverse: AAGTGGTCCAACAGCAGCTT | 17 |  |
| NOTCH3 | Mouse | Forward: CGGAGGGAGCCTGTGGGACA | 18 | Expression |
|  |  | Reverse: GGAGTCAGCGCTGTGGCTGG | 19 |  |
| NOTCH4 | Human | Forward: GGCTTCTACTCCGCTTCCTT | 20 | Expression |
|  |  | Reverse: GATGAGCTGGAGGACGAGAA | 21 |  |
| NOTCH4 | Mouse | Forward: AAGCGACACGTACGAGTCTGG | 22 | Expression |
|  |  | Reverse: ATAGTTGCCAGCTACTTGTGG | 23 |  |
| HES1 | Human | Forward: GCAGATGACGGCTGCGCTGA | 24 | Expression |
|  |  | Reverse: AAGCGGGTCACCTCGTTCATGC | 25 |  |
| HES1 | Mouse | Forward: TCCAAGCTAGAGAAGGCAGAC | 26 | Expression |
|  |  | Reverse: TGATCTGGGTCATGCAGTTG | 27 |  |
| HES1 | Human | Forward: AAGTTTCACACGAGCCGTTC | 28 | ChIP |
|  |  | Reverse: GCTGTTATCAGCACCAGCTC | 29 |  |
| NRARP | Human | Forward: CGCTGTTGCTGGTGTTCTAA | 30 | Expression |
|  |  | Reverse: CATTGACCACGCAGTGTTTT | 31 |  |
| NRARP | Human | Forward: ACCAACTGCGAGTTCAACG | 32 | ChIP |
|  |  | Reverse: AGCTTCACGAGCTCCAGGT | 33 |  |
| BCL2 | Human | Forward: ATAACGGAGGCTGGGTAGGT | 34 | Expression |
|  |  | Reverse: CAGCCAGGAGAAATCAAACA | 35 |  |

-continued

| Gene | Species | Sequence | SEQ ID NO: | Application |
|---|---|---|---|---|
| BCL2 | Mouse | Forward: TGGGATGCCTTTGTGGAACT<br>Rev: ACAGCCAGGAGAAATCAAACAG | 36<br>37 | Expression |
| ADAMDEC1 | Human | Forward: CAACACCAGTGTGTGGGAAC<br>Reverse: TCTTGTCCTGGCAAGGTAGC | 38<br>39 | Expression |
| ADAMDEC1 | Mouse | Forward: GACTGCAGTGAAGCATCCAA<br>Reverse: CGTATTTTGGGGCATTCTTC | 40<br>41 | Expression |
| ITGAX | Human | Forward: AGGACAGCCTTGGGGGAGAC<br>Reverse: CTGTCCTACCGCTACGTGGCA | 42<br>43 | Expression |
| ITGAX | Mouse | Forward: CCAGGTTGCCCAGTGAGAA<br>Reverse: CTCAGATGGGCGGGTTCA | 44<br>45 | Expression |
| MMP9 | Human | Forward: ATGCTGCTGTTCAGCGGGCG<br>Reverse: CGGGAACTCACGCGCCAGTA | 46<br>47 | Expression |
| MMP9 | Mouse | Forward: CATTCGCGTGGATAAGGAGT<br>Reverse: TCACACGCCAGAAGAATTTG | 48<br>49 | Expression |
| CD74 | Human | Forward: TGGGAGCATCGGCTACTGCTG<br>Reverse: TGCTCTCACATGGGGACTGGG | 50<br>51 | Expression |
| CD74 | Mouse | Forward: CCAACGCGACCTCATCTCTAA<br>Reverse: AGGGCGGTTGCCCAGTA | 52<br>53 | Expression |
| CDKN1A | Human | Forward: TGCGCCAGCTGAGGTGTGAG<br>Reverse: TCGCTGTCCACTGGGCCGAA | 54<br>55 | Expression |
| GAPDH | Human | Forward: CTTTTGCGTCGCCAGCCGAG<br>Reverse: CCAGGCGCCCAATACGACCA | 56<br>57 | Expression |
| GAPDH | Mouse | Forward: TGGTGAAGGTCGGTGTGAAC<br>Rev: CCATGTAGTTGAGGTCAATGAAGG | 58<br>59 | Expression |

Cells Cross-Linking and Preparation of Mononucleosomes-Containing Chromatin.

The cells were fixed with 1% formaldehyde for 10' at RT and incubated in buffer A (10 mM Hepes pH 7.5, 10 mM KCl, 1.5 mM MgCl$_2$, 0.2 mM glycerol), followed by addition of NP-40 in final concentration 0.5% and stirring. The nuclei were isolated by centrifugation and washed once with "digest" buffer (10 mM NaCl, 10 mM Tris-HCl pH 7.5, 3 mM MgCl$_2$, 1 mM CaCl$_2$, 0.1 mM PMSF) followed by incubation with Micrococcal nuclease (from USB) in "digest" buffer at 37° C. in order to generate mononucleosomal particles. The reaction was stopped with the addition of EDTA (20 mM) and the nuclei were lysed using the "Nuclei lysis" buffer (50 mM Tris-HCL pH 80), 10 mM EDTA (pH 8.0) and 1% SDS) followed by sonication (2.5° in total) using the bioruptor from Diagenode and addition of 9 volumes of "IP dilution" buffer (0.01% SDS, 1.1% Triton X-100, 1.2 mM EDTA (pH 8.0), 16.7 mM Tris-HCl pH8.0 and 167 mM NaCl) and addition of the magnetic dynal beads (pre-clearing of chromatin).

Chromatin Immunoprecipitation.

Standard ChIP-Seq procedures (Barski et al., "High-Resolution Profiling of Histone Methylations in the Human Genome," Cell 129:823-837 (2007); Wang, et al., "Combinatorial Patterns of Histone Acetylations and Methylations in the Human Genome," Nat. Genet. 40:897-903 (2008), which are hereby incorporated by reference in their entirety) were adapted to the cell numbers (~1-5×10$^6$ cells). The antibody was incubated with the beads for 4 hours in "IP dilution" buffer. The complex was added to the chromatin followed by overnight incubation. The complexes bound on the beads were washed with buffers (wash A: 20 mM Tris-HCl pH 8, 150 mM NaCl, 2 mM EDTA, 1% w/v Triton, 0.1% w/v SDS, wash B: 20 mM Tris-HCl pH 8, 500 mM NaCl, 2 mM EDTA, 1% w/v Triton, 0.1% w/v SDS) having increasing concentration of NaCl, once with wash buffer C (10 mM Tris-HCl pH 8, 250 mM LiCl, 1 mM EDTA, 1% w/v Nonidet P-40, 1% w/v deoxycholic acid) and twice with TE. The precipitated DNA was cleaned with treatment with PK, at 65° C. overnight and phenol/chloroform extraction.

ChIP-Seq.

ChIP-seq analysis of LSK and AML LIC was previously described (Bernt et al., "MLL-Rearranged Leukemia is Dependent on Aberrant H3K79 Methylation by DOT1L," Cancer Cell 20:66-78 (2011), which is hereby incorporated by reference in its entirety) and data are available at the Gene Expression Omnibus under accession number GSE29130.

Bone Marrow Transplantation Assays.

2×10$^6$ total spleen cells from Ncstn−/− or Ncstn−/−Tet2−/− mice (Ly5.2$^+$) and 5×10$^5$ total bone marrow cells from congenic BL6SJL mice (Ly5.1$^+$) were transplanted by retro-orbital i.v. injections into lethally irradiated (2 times 550 cGy separated by 4 hours) BL6SJL (Ly5.1$^+$) recipient mice. Peripheral blood of recipient mice was collected at 5, 10 and 15 weeks after transplant.

Retroviral Infection of Linegae$^{neg}$cKit$^+$ Bone Marrow Cells and Transplantation.

Bone marrow cells were enriched for cKit-positive cells using the EasySep kit (StemCell Technology) and cultured in OPTI-MEM supplemented with 10% fetal bovine serum, 100 µ/ml penicillin, 100 µg/ml streptomycin, 50 ng/ml of SCF, 10 ng/ml of IL6 and 10 ng/ml IL3. For retroviral production, Plat-E cells were transfected with MIG-MLL-AF9 by calcium phosphate method. Virus supernatant was collected 48 hr post transfection and used directly for spin infection of cKit positive-enriched bone marrow cells at 2500 rpm for 90 minutes. Forty-eight hours after infection, lineage-negative GFP-positive cells were sorted for transplantation, and 50,000 sorted cell were mixed with $5 \times 10^5$ total bone marrow cells from congenic BL6SJL mice (Ly5.1$^+$) and transplanted by retro-orbital i.v. injections into lethally irradiated (2 times 550 cGy separated by 4 hours) BL6SJL (Ly5.1$^+$) recipient mice.

Comparison of N1-IC and N2-IC Expression in Hematopoietic System.

ROSA26-ICN mice were crossed to UbcCreER mice and freshly isolated bone marrow cells were prepared as described. Total bone marrow cells ($2 \times 10^6$) were resuspended in 100 ml PBS and kept on ice until retro-orbital injection into lethally irradiated ($2 \times 550$ Gy) wild type CD45.2 recipients. Four weeks after reconstitution, ICN expression was induced via 3 consecutive intraperitoneal injections of tamoxifen daily at a dose of 0.2 mg/g mouse. At 2, 4 and 6 weeks after the last injection, peripheral blood was analyzed and animals were followed for survival.

In Vitro Differentiation Assays.

Sorted AML LIC (500) were plated in triplicates into cytokine-supplemented methylcellulose medium (MethoCult 3434, Stem Cell Technologies) in the presence of 250 nM 4-OHT or vehicle DMSO. Colony number was scored after 8 days of culture. Cells were recovered 8 days later, stained and analyzed by FACS as described.

Cell Cultures and Dll4-Fc Stimulation.

Murine AML LIC were cultured in OPTI-MEM supplemented with 10% FBS, 100 µ/ml penicillin, 100 µg/ml streptomycin, 50 ng/ml of SCF, 10 ng/ml of IL6 and 10 ng/ml IL3 for 24 or 48 hours. Human cell lines THP1, U937, Loucy and KOPTK were cultured in RPMI with 10% FBS, 100 µ/ml penicillin, 100 µg/ml streptomycin. Human primary AML samples were cultured in SFEM (Stem Cell Technologies) supplemented with 100 ng/ml SCF, 50 ng/ml TPO, 50 ng/ml FLT3L, 20 ng/ml IL6 and 20 ng/ml IL3 for 24 hours. Murine and human cytokines were purchased from Peprotech. For Dll4-Fc and Fc stimulation, tissue culture plates were coated overnight with a solution of PBS and 60 nM Dll4-Fc or Fc at 4° C. then washed with PBS prior to use for culture.

Cell Death Assays.

Cells were stained with Annexin V and 7-AAD according to the manufacturer instructions (BD Biosciences) to assess levels of apoptosis. TUNEL assay (Millipore) was done on 4 µm sections of paraffin embedded tissues, deparaffinized with xylene and stained following manufacturer's instructions.

Cell Cycle Analysis.

For Ki67/DAPI staining, the cells were first treated with Fix and Perm reagents according to manufacturer's instruction (Invitrogen), incubated with 20 µl of Ki67-PE conjugated antibody (BD) in 100 µl of solution B for 20 min, then washed and resuspended in PBS with 5 µg/ml RNaseA and 2 µg/ml DAPI. Stained cells were analyzed using a BD FACS Fortessa.

Histological Analyses.

Mice were killed and autopsied, and then dissected tissue samples or tumors were fixed for 24 h in 10% buffered formalin, dehydrated and embedded in paraffin. Paraffin blocks were sectioned at 4 µm and stained with haematoxylin and eosin. Images were acquired using a Zeiss Axio Observer A1 microscope (Zeiss).

Wright-Giemsa Staining.

To examine morphological changes associated with myeloid differentiation, cells were cytospinned 5 min at 500 rpm onto microscope slides. Cells were fixed and permeabilized in 100% methanol for 30 seconds, stained for 3 minutes in Wright-Giemsa stain (Fisher), stained for 10 minutes in 15% Wright-Giemsa stain, 1% Azure Blend (Fisher), 84% ddH2O, then stained for 2 minutes in 12% Wright-Giemsa stain and 88% phosphate buffer pH 6.8, then washed with ddH$_2$O. Images were acquired using a Zeiss Axio Observer A1 microscope (Zeiss).

Peripheral Blood Analysis.

Blood was collected by retro-orbital bleeding using heparinized micro-hematocrit capillary tubes (Fisher). Automated peripheral blood counts were obtained using a HemaVet 950 (Drew Scientific) following standard manufacturer's instruction. Differential blood counts were realized on blood smears stained using Wright-Giemsa staining and visualized using a Zeiss Axio Observer A1 microscope (Zeiss).

Microarray Analysis.

LSK, mT-ALL and AML LIC cells from individual mice were used. Freshly isolated cells were sorted by surface marker expression, and total RNA was extracted using the RNeasy kit (QIAGEN, CA). In order to generate sufficient sample quantities for oligonucleotide gene chip hybridization experiments, the Ovation® RNA Amplification System V2 (Nugen) for cRNA amplification and labeling was used. The amplified cRNA was labeled and hybridized to the Mouse 430.2 microarrays (Affymetrix). For human THP1 cells micro-arrays, cRNA was labeled and hybridized to the Human HG133plus2 microarrays (Affymetrix). The Affymetrix gene expression profiling data was normalized using the previously published Robust Multi-array Average (RMA) algorithm using the GeneSpring GX software (Agilent, Palo Alto, Calif.). The gene expression intensity presentation was generated with Multi-Experiment Viewer software (v4.7.4). All newly generated microarray data have been deposited to GEO database and are available upon accession number GSE42261.

Human Samples Microarray Analysis.

AML and HSPC samples used in this study have been described previously (Gentles et al., "Association of a Leukemic Stem Cell Gene Expression Signature With Clinical Outcomes in Acute Myeloid Leukemia," *JAMA: The Journal of the American Medical Association* 304:2706-2715 (2010); Metzeler et al., "An 86-Probe-Set Gene-Expression Signature Predicts Survival in Cytogenetically Normal Acute Myeloid Leukemia," *Blood* 112:4193-4201 (2008); Verhaak et al., "Prediction of Molecular Subtypes in Acute Myeloid Leukemia Based on Gene Expression Profiling," *Haematologica* 94:131-134 (2009), which are hereby incorporated by reference in their entirety) and are available at the Gene Expression Omnibus under references GSE6891, GSE24006 and GSE12417. Analysis was performed using R 2.14.0 and BioConductor. Raw data were generated using RMA package. For comparison of different array sets, Raw expression data were normalized to the average of control GAPDH probe sets.

AML Blast Staining, Purification and Expression Analysis of AML Samples.

Mononuclear cells from AML patients were prepared using Ficoll-Paque Plus (GE Healthcare). Mononuclear fractions were stained with fluorochrome-conjugated antibodies (Table 2 below). Cells were stained on ice and dead cells were excluded by propidium iodide staining. Cells were sorted to >90% purity by FACS analysis. Total RNA was extracted from FACS-sorted AML patient blast populations using Ambion RNA Isolation Kit (Applied Biosystems) and treated with DNaseI (Qiagen). RNA samples were subjected to reverse transcription, linear amplification, production and fragmentation of biotinylated cRNA (Affymetrix). 15 µg of cRNA from each sample was hybridized to Affymetrix HG U133 Plus 2.0 microarrays.

TABLE 2

| Antibody Target | Antibody | Antibody Source |
|---|---|---|
| CD45RA, human | MEM56 | BD Biosciences |
| CD38, human | HIT2 | BD Biosciences |
| CD90, human | 5E10 | BD Biosciences |
| CD34, human | 581 | BD Biosciences |
| CD123, human | 7G3 | BD Biosciences |
| CD3, human | S4.1 | BD Biosciences |
| CD19, human | SJ25-C1 | BD Biosciences |

GeneSet Enrichment Analysis.

Geneset Enrichment Analysis was performed using GSEA software (Subramanian et al., "Gene Set Enrichment Analysis: A Knowledge-Based Approach for Interpreting Genome-Wide Expression Profiles," *Proc. Nat'l. Acad. Sci. U.S.A.* 102:15545-15550 (2005), which is hereby incorporated by reference in its entirety), using Gene set as permutation type, 1000 permutations and log 2 ratio of classes as metric for ranking genes.

The Dendritic cells and Macrophage differentiation genesets were generated using a systematic approach based on the comparison of gene expression arrays from WT GMP and splenic macrophages and dendritic cells (DC). Genes that were significantly upregulated in GMP compared to macrophages or DC (over 2 fold induction p-value<0.05) were used to define differentiation signature genes. Other Genesets used in the analysis were taken from genesets already present in the MSig Database of the Broad Institute or previously published.

Statistical Analysis.

The means of each data set were analyzed using the Student's t test, with a two-tailed distribution and assuming equal sample variance. Statistical analysis of Kaplan-Meier survival curve is done using "Gehan-Breslow-Wilcoxon Test".

Example 1

Notch Signaling Pathway is Silenced in Primary AML Patient Cells

To address the possible involvement of Notch signaling pathway in AML the status of the Notch pathway expression in primary AML patient samples was investigated, focusing on acute myelomonocytic leukemias (M4, M4E and M5 FAB subtypes). Whole transcriptome data from 187 M4-5 AML (Verhaak et al., "Prediction of Molecular Subtypes in Acute Myeloid Leukemia Based on Gene Expression Profiling," *Haematologica* 94:131-134 (2009), which is hereby incorporated by reference in its entirety) was compared with micro arrays from normal Lineage negative CD34+/CD38− human bone marrow stem and progenitor cells (HSPC) (Gentles et al., "Association of a Leukemic Stem Cell Gene Expression Signature With Clinical Outcomes in Acute Myeloid Leukemia," *JAMA: The Journal of the American Medical Association* 304:2706-2715 (2010), which is hereby incorporated by reference in its entirety). As expected, normal HSPC showed expression of Notch target genes including well characterized HES1, NRARP, DTX1 and HEY1 (FIG. 1A), all direct targets of Notch signaling in hematopoietic cells and other tissues (Ntziachristos et al., "Genetic Inactivation of the Polycomb Repressive Complex 2 in T Cell Acute Lymphoblastic Leukemia," *Nat. Med.* 18:298-301 (2012); Palomero et al., "NOTCH1 Directly Regulates c-MYC and Activates a Feed-Forward-Loop Transcriptional Network Promoting Leukemic Cell Growth," *Proc. Nat'l. Acad. Sci. U.S.A.* 103:18261-18266 (2006); Wang et al., "Genome-Wide Analysis Reveals Conserved and Divergent Features of Notch1/RBPJ Binding in Human and Murine T-Lymphoblastic Leukemia Cells," *Proc. Nat'l. Acad. Sci. U.S.A.* 108:14908-14913 (2011), which are hereby incorporated by reference in their entirety). By contrast, Notch activation signature was not observed in most AML samples. Notch receptors also showed a distinct pattern of expression between AML and HSPC. Whereas NOTCH1 and NOTCH2 were highly expressed in HSPC, NOTCH1 mRNA was expressed significantly lower in AML samples (FIG. 1B). Strikingly, NOTCH2 mRNA retained high expression in AML samples. Interestingly, "activated" forms of Notch receptors were not detected using western blotting of primary human AML samples supporting the gene-expression studies and the notion of pathway suppression in this type of leukemia. To address the status of Notch activation in putative leukemia-initiating populations, CD34+/CD38− and CD34+/CD38+ stem/multipotential progenitor populations from AML patients were purified (Table 3) and whole genome microarray analysis was performed. Expression data from these populations was compared with normal CD34+ bone marrow stem cells. Similar to previous studies, Notch target gene expression was significantly down-regulated (FIG. 1C). These data indicate that Notch signaling is also silenced in human AML initiating cells.

TABLE 3

Characteristic of patients used for AML stem cell expression arrays.

| | Age | Gender | Histology | % blasts | Sample type | Cytogenetics |
|---|---|---|---|---|---|---|
| 1 | 44 | F | AML, FAB M1 | 78 | BM | |
| 2 | 21 | M | AML, M4 | 63 | BM | Normal 46, XY male phenotype, negative for MLL and CBFB by FISH |
| 3 | 52 | M | ACUTE MYELOID LEUKEMIA | 88 | Bm | |
| 4 | 63 | M | ACUTE MYELOID LEUKEMIA (from CMML) | 53 | BM | 11q23 |

TABLE 3-continued

Characteristic of patients used for AML stem cell expression arrays.

| | Age | Gender | Histology | % blasts | Sample type | Cytogenetics |
|---|---|---|---|---|---|---|
| 5 | 56 | M | AML arising from MDS | 31 | BM | 46, XY, add(3)(p12), del(5)(q13), −11, −17, +r(?), +mar1[8]/46, sl, +11, −13, +14, −r(?), −mar1, +mar[7]/46, sl, −add(3)(p12), −mar1, +2mar[2]/46, XY[2] |
| 6 | 60 | M | AML w/maturation | | BM | |
| 7 | 44 | M | AML, M1 | 80 | BM | Not performed |
| 8 | 56 | M | AML, treatment related | 89 | PB | |
| 9 | 45 | M | Acute myelomonocytic leuk (fr MDS) | 92 | BM | no −5, −7 |
| 10 | 13 | F | residual AML | 9 | BM | 46, XX[29]; nuc ish(ETO, AML1)x2[200]; nuc ish(MLLx2)[200]; nuc ish(CBFBx2)[200] |
| 11 | 60 | M | AML (from PV) | 20-30 | BM | 47, XY, t(7;16)(p13;p13.3)c, +21[4]/47, XY, t(7;16)(p13;p13.3)c, +11[3]/46, XY, t(7;16)(p13;p13.3)c[13] Twenty metaphase cells were analyzed, all of which demonstrated a previously identified constitutional translocation [t(7;16)]. Four cells were trisomic for chromosome #21, and three cells were trisomic for chromosome #11. |
| 12 | 54 | M | ACUTE MYELOCYTIC LEUKEMIA (fr MDS) | 40 | BM | |

To gain further insights into the mechanisms responsible for Notch pathway silencing in AML samples chromatin immune-precipitation (ChIP) was performed followed by quantitative PCR for the H3K27me3 repressive histone mark at known Notch target loci in AML patient samples of different subtypes (Table 4). When compared to wild type human Lineage$^{neg}$CD34$^+$ cord blood stem/progenitor cells, all tested AML samples showed a marked increase of H3K27me3 abundance on the promoter of the canonical Notch target HES1, compared to CD34$^+$ cord blood cells (FIG. 1D right panel). This increase in H3K27me3 abundance was tightly correlated with down-regulation of HES1 gene expression in AML samples revealed by qPCR (FIG. 1D left panel). Increased H3K27me3 was also evident on other canonical Notch target genes including NRARP (FIG. 1E left panel) and once again correlated with downregulation of gene expression (FIG. 1E right panel). H3K27me3 status of HES1 promoter was investigated in the human AML cell line THP1 compared to Notch-dependent T-ALL cell line DND41. Consistent with observations in human AML samples, HES1 promoter showed high increase in H3K27me3 in THP1 cells compared to DND41 cells (FIG. 1F right panel) and this increase was correlated with a reduced expression of HES1 gene (FIG. 1F left panel). Accumulation of H3K27me3 at the promoter of Notch target genes is consistent with inactivation of this signaling pathway in AML. Taken together these data show that Notch signaling is silenced in human AML, excluding a "positive" role for Notch signaling in AML disease progression. Additionally, AML cells specifically express NOTCH2 gene suggesting that Notch signaling could be re-activated in those cells upon ligand binding to the NOTCH2 receptor.

TABLE 4

Characteristics of AML patients of this study

| Patient Number | FAB Subtype | Cytogenetic | Mutations |
|---|---|---|---|
| 1 | Non-M3 | 48, XY, add(4)(p16), +8, der(16)del(16)(p13.1p13.3), del(16)(q22q24) | NC |
| 2 | M4E | 46, XX, inv(16)(p13.1q22) | NC |
| 3 | M1 | Normal karyotype 46, XY | FLT3-ITD positive |
| 4 | M4E | 46, XX, inv(16)(p13.3q22) | NC |
| 5 | M4E | 46, XY, inv(16) | NPM-1 negative FLT-3 ITD negative |
| 6 | M5 | Normal karyotype 46, XX | NPM-1 positive FLT-3 ITD positive |
| 7 | M1 | 46, XX, t(4; 11) fusion transcripts (e10/e4 and e9/e5) | FLT3 ITD negative |

Example 2

Notch Signaling is Silenced in an MLL-AF9 Driven Murine AML Model

Figures 2A, 2B, 2C:
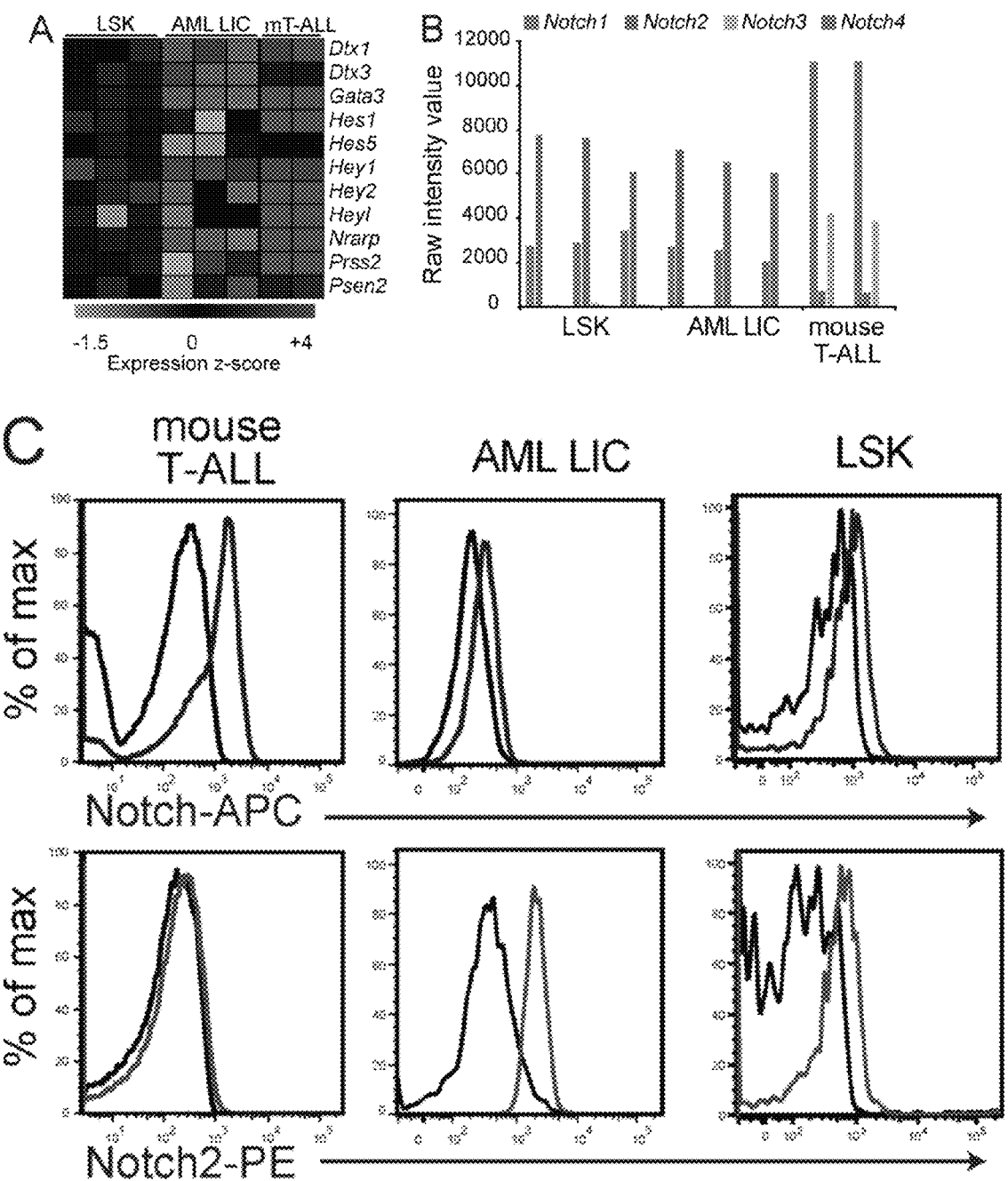
FIGS. 2A-2E show Notch signaling pathway silencing in a murine AML model induced by MLL-AF9.
Figures 2D, 2E:
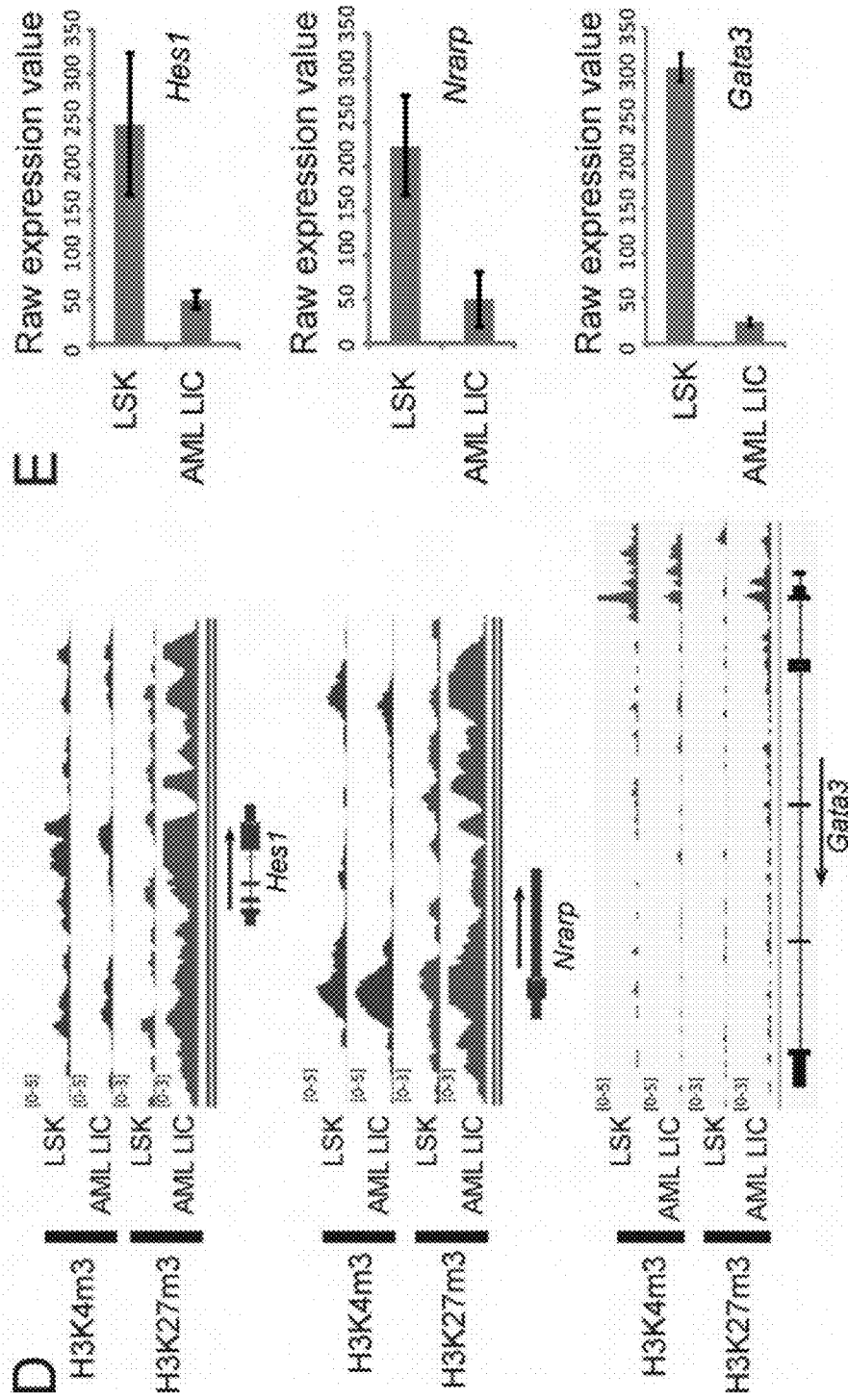

The MLL-AF9 driven AML animal model that shares several common features with MLL translocation-driven human AML (Krivtsov et al., "Transformation From Committed Progenitor to Leukaemia Stem Cell Initiated by MLL-AF9," Nature 442:818-822 (2006), which is hereby incorporated by reference in its entirety) was used study the in vivo role of Notch signaling in AML. Bone marrow hematopoietic stem and progenitor cells (HSPC: Lineage$^{neg}$c-Kit$^+$) were transduced with a retrovirus driving expression of the human MLL-AF9 fusion protein as well as YFP. YFP cells were then purified and transplanted into lethally irradiated mice together with a radio-protective dose of wild type bone marrow. After disease establishment, mice were sacrificed and leukemia initiating cells (LIC) were flow-purified and used for whole transcriptome analysis together with wild type Lin$^{neg}$Sca-1$^+$c-Kit$^+$ (LSK) cells and NOTCH1-IC-induced murine T-ALL primary leukemia cells (Ntziachristos et al., "Genetic Inactivation of the Polycomb Repressive Complex 2 in T Cell Acute Lymphoblastic Leukemia," *Nat. Med.* 18:298-301 (2012), which is hereby incorporated by reference in its entirety). In murine MLL-AF9-driven AML, LICs are found in a population phenotypically resembling GMP but sharing common gene expression with HSC (Krivtsov et al., "Transformation From Committed Progenitor to Leukaemia Stem Cell Initiated by MLL-AF9," *Nature* 442:818-822 (2006), which is hereby incorporated by reference in its entirety) and therefore represent a population of therapeutic importance. Microarray analysis revealed that the Notch gene signature previously used for the study of human AML samples was significantly under-represented in mouse AML LIC. The same genes were, as expected, highly expressed in murine T-ALL cells (FIG. 2A). The Notch signaling signature was also detected in the LSK population (FIG. 2A). Consistent with observations made in human AML primary samples, NOTCH1 expression was low in mouse AML LIC whereas NOTCH2 gene showed an inverse pattern of expression with high expression in LIC (FIG. 2B). Extracellular staining using NOTCH1 and NOTCH2 specific antibodies followed by FACS analysis confirmed these results at the protein level (FIG. 2C). Chromatin-immunoprecipitation (ChIP) and massive parallel sequencing (ChIP-Seq) data for the histone marks H3K4me3 and H3K27me3 (Bernt et al., "MLL-Rearranged Leukemia is Dependent on Aberrant H3K79 Methylation by DOT1L," *Cancer Cell* 20:66-78 (2011), which is hereby incorporated by reference in its entirety) was assessed to gain further insight into mechanisms responsible for Notch signaling silencing in AML LIC. Analysis of canonical Notch target genes (Hes1, Nrarp and Gata3) revealed a significant gain of the H3K27me3 repressive histone mark on each promoter and on gene bodies in the LIC population when compared to the LSK subset (FIG. 2D). This gain of repressive epigenetic mark was directly correlated to gene expression levels (FIG. 2E) consistent with a role for H3K27me3 in repression of Notch pathway gene expression. Interestingly, NOTCH2 locus did not show a significant increase in H3K27me3. Moreover, H3K4me3 was globally maintained at a high level in LSK and LIC (FIG. 2D), suggesting that Notch target genes might be poised for activation. Taken together these data demonstrate that Notch signaling pathway is silenced in MLL-AF9 driven murine model of AML, and that AML leukemic initiating cells specifically express NOTCH2 indicating that Notch signaling pathway can be re-activated.

Example 3

In Vivo Activation of Notch Signaling Suppresses MLL-AF9 Induced AML

Whether re-activation of Notch signaling could suppress AML in in vivo was tested using a conditional knock-in model of NOTCH1-IC (EF1α$^{wt/lsl-N1-IC}$) crossed to the tamoxifen-inducible ROSA-creERT2 strain. Upon tamoxifen induction the Notch1-IC transgene is expressed, leading to constitutive activation of the Notch pathway (Buonamici et al., "CCR7 Signalling as an Essential Regulator of CNS Infiltration in T-cell Leukaemia," *Nature* 459:1000-1004 (2009), which is hereby incorporated by reference in its entirety). HSPC from EF1α$^{wt/lsl-N1-IC}$ ROSA$^{wt/CreERT2}$ and ROSA$^{wt/CreERT2}$ littermates were transduced with MLL-AF9-IRES-YFP retrovirus, flow-purified and transplanted into lethally irradiated congenic recipient together with radio-protective bone marrow. Three weeks after transplantation, mice were bled to assess the state of disease progression and subsequently dosed with tamoxifen. Six days after tamoxifen administration a small number of mice was analyzed and the remaining mice were followed over time for disease progression and survival.

Figures 3A, 3B, 3C, 3D, 3E, 3F:
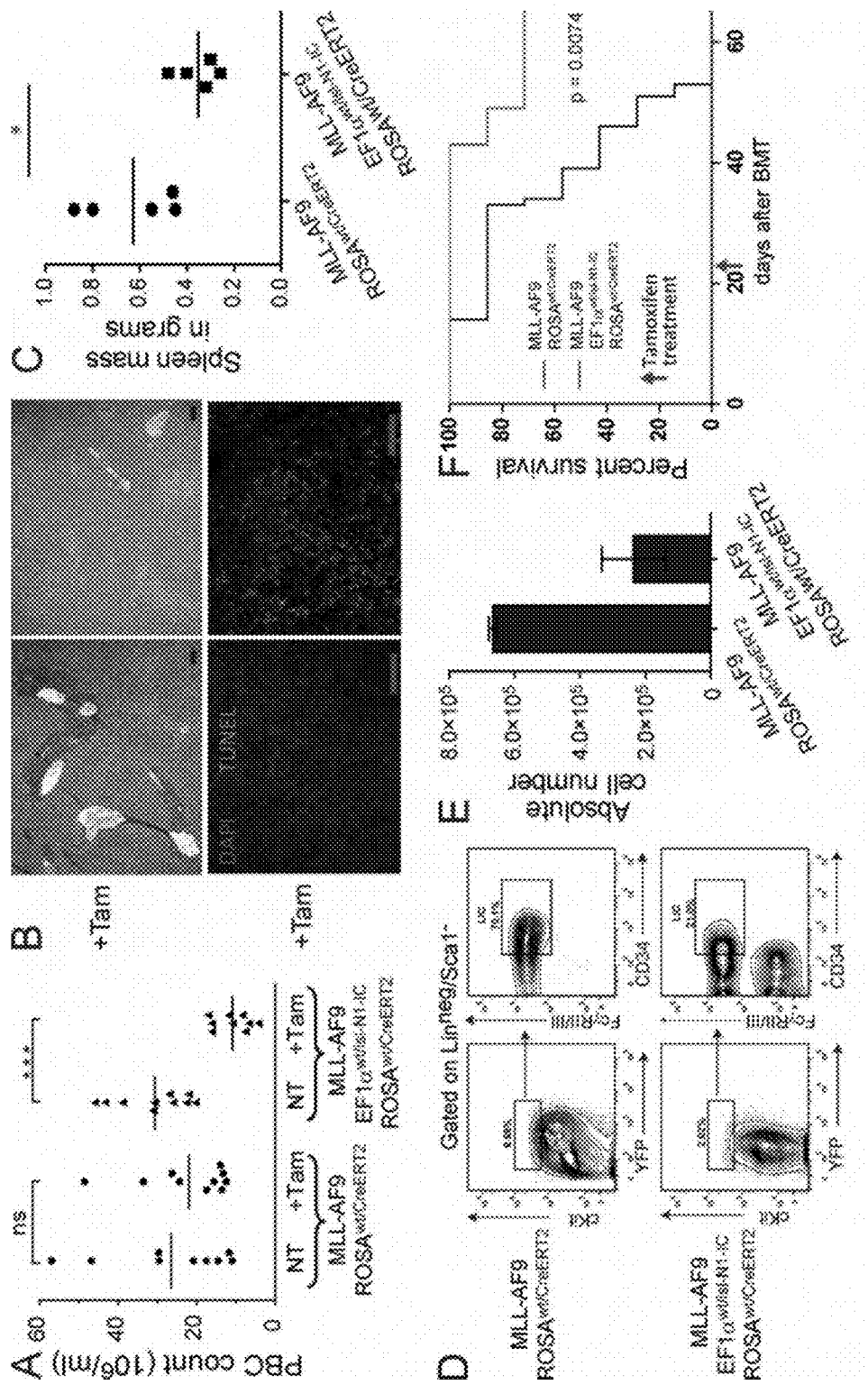
FIGS. 3A-3M demonstrate that activation of Notch signaling suppress AML progression in vivo.

Peripheral blood analysis showed a striking reduction in the proportion of YFP$^+$ cells and in overall white blood cell counts in NOTCH1-IC-expressing MLL-AF9 positive mice compared to the control cohort (FIG. 3A). Tissue analysis revealed a significant decrease in spleen size (FIG. 3C) and further histological analysis showed significantly reduced tissue infiltration in NOTCH1-IC expressing mice compared to control mice (FIG. 3B upper panel). Terminal deoxynucleotidyl transferase dUTP nick end labeling (TUNEL) assay on spleen sections showed a marked increase of apoptotic cells in NOTCH1-IC expressing cohort (FIG. 3B lower panel), suggesting that Notch activation induces apoptosis of AML cells in vivo. Most importantly, NOTCH-IC induction resulted in a significant decrease of relative proportion and absolute number of leukemic initiating cells (FIGS. 3D-E) and a significant increase in overall survival compared to control mice (FIG. 3F, p<0.01). These data demonstrate that in vivo Notch re-activation is able to efficiently suppress AML disease progression by inducing AML cells apoptosis.

Figures 3G, 3H, 3I, 3J, 3K, 3L, 3M:
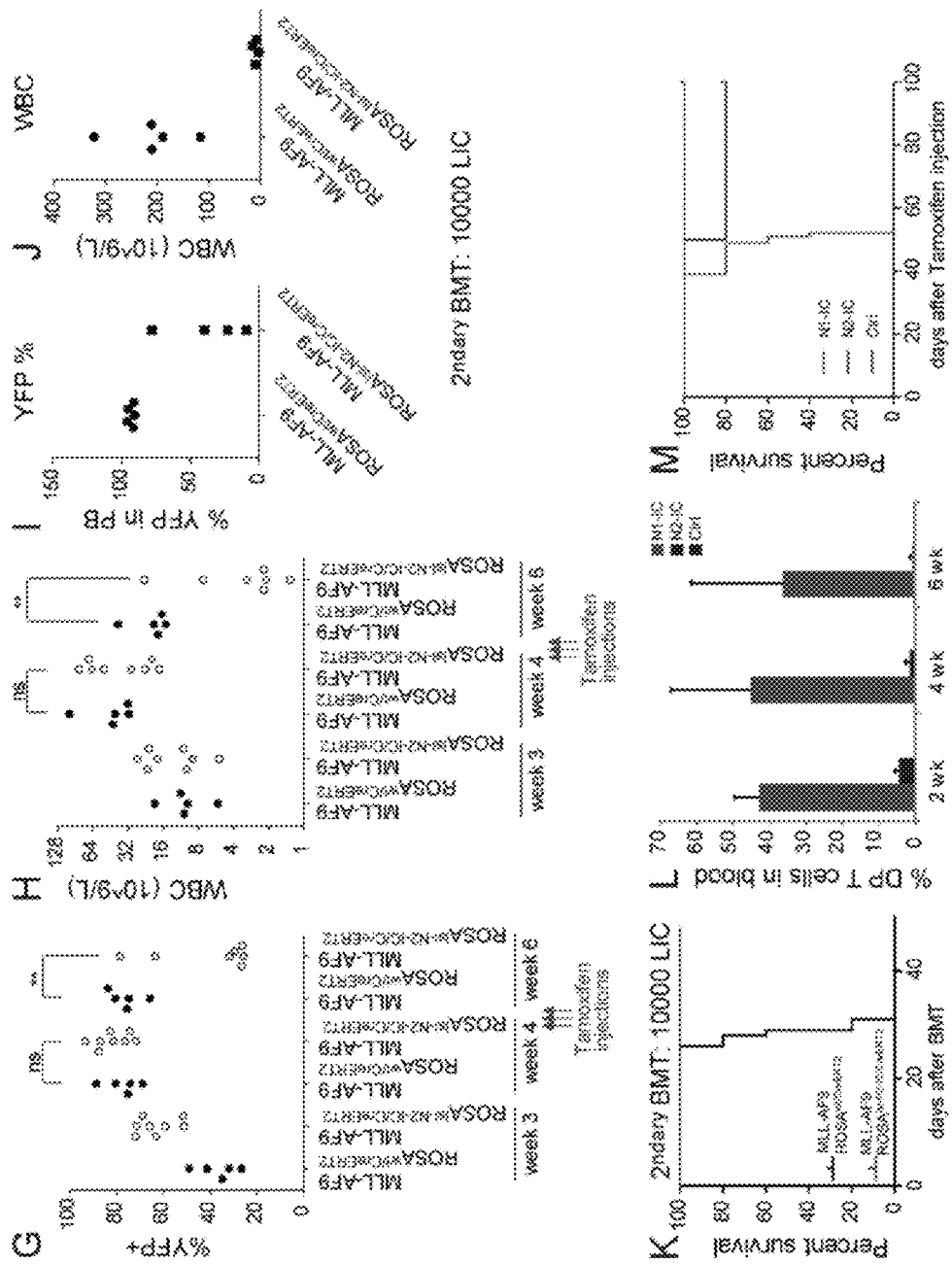

As AML cells mainly express NOTCH2 receptor on their surface, similar experiments were carried out using an inducible knock in allele of NOTCH2-IC (Rosa26$^{lsl-N2-IC/CreERT2}$). HSPC isolated from Rosa$^{lsl-N2-IC/CreERT2}$ and control Rosa$^{wt/CreERT2}$ mice were infected with MLL-AF9 and transplanted in lethally irradiated congenic recipients together with a radio-protective dose of WT bone marrow. After disease establishment recipient mice were injected 3 times with tamoxifen. After tamoxifen injection YFP$^+$ cells as well as white blood cell count were dramatically reduced in Rosa$^{N2-IC+/CreERT2}$ MLL-AF9 positive mice compared to control cohort (FIG. 3G-H). Remaining LIC after tamoxifen injection were sorted and transplanted in sub-lethally irradiated secondary recipient. Three weeks after transplantation mice from control cohort (Rosa$^{wt/CreERT2}$ MLL-AF9+) showed highly elevated blood counts with over 90% of the peripheral blood cells expressing MLL-AF9 (YFP$^+$) whereas mice transplanted with Rosa$^{N2-IC+/CreERT2}$ LIC showed low white blood cell count and low percentage of MLL-AF9 expressing cells (FIG. 3I-J). Finally, control mice transplanted with LIC purified from Rosa$^{wt/CreERT2}$ died within 30 days after transplantation whereas mice transplanted with Rosa$^{N2-IC+/CreERT2}$ survived (FIG. 3K).

To address potential side-effects of Notch2 activation on normal hematopoietic cells, total bone marrow cells from Rosa$^{lsl-N2-IC/wt}$ Ubc-CreER, Rosa$^{lsl-N1-IC/wt}$, Ubc-creER and control Rosa$^{wt/wt}$ Ubc-CreER mice were transplanted in lethally irradiated congenic recipients. After engraftment was verified, mice were injected with tamoxifen. As previously reported, mice with hematopoietic cells expressing N1-IC developed aggressive T-ALL characterized by abnormal presence of CD4/CD8 double positive T cells in the peripheral blood (FIG. 3L). Interestingly, mice with hematopoietic cells expressing N2-IC presented with a low abundant transient wave of CD4/CD8 double positive T cells in the peripheral blood but didn't develop any sign of acute T cell leukemia. Finally, all the mice expressing N1-IC died of aggressive T-ALL within 60 days after tamoxifen injection whereas almost all mice expressing N2-IC survived without any signs of T-ALL or other adverse effects (FIG. 3M). Taken together these data demonstrate that in vivo activation of the Notch pathway can suppress established AML in vivo and suggested that Notch (and specifically Notch2) agonists could be an attractive therapeutic option.

Example 4

Notch Activation Targets LIC Differentiation and Cell Survival

Figures 4A, 4B, 4C:
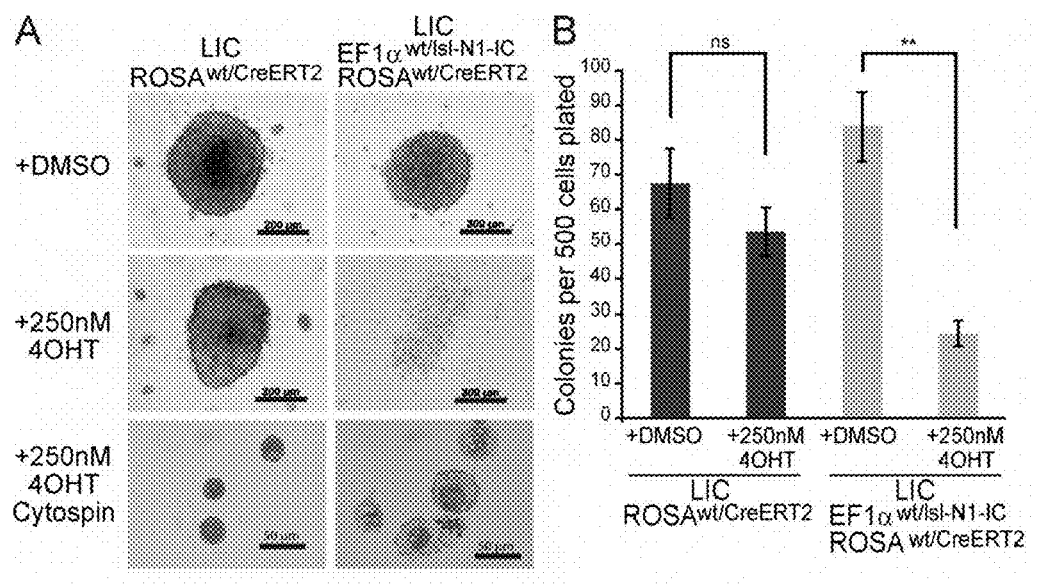
FIGS. 4A-4E show that Notch activation induces AML LIC differentiation and apoptosis.

To gain additional information into the mechanisms of Notch-mediated AML suppression, LIC from non-Tamoxifen treated $EF1\alpha^{wt/lsl-NOTCH1-IC}$ $ROSA^{wt/CreERT2}$ and $ROSA^{wt/CreERT2}$ mice were flow-purified and plated in methylcellulose cultures in presence of 4-HydroxyTamoxifen (4OHT) or DMSO. DMSO treated LIC showed similar blast colony forming capacity between $EF1\alpha^{wt/lsl-NOTCH1-IC}$ $ROSA^{wt/CreERT2}$ and $ROSA^{wt/CreERT2}$. However, $EF1\alpha^{wt/lsl-NOTCH1-IC}$ $ROSA^{wt/CreERT2}$ treated with 4OHT showed a marked decrease of colony number (FIG. 4B) and loss of blast colony morphology (FIG. 4A). Cytospin of representative colonies followed by Wright-Giemsa staining revealed that NOTCH1-IC expressing LIC differentiated to more mature cell fates, with morphology resembling macrophages or dendritic cells (FIG. 4A). AnnexinV staining revealed increased proportion of cell undergoing apoptosis (FIG. 4C).

Figure 4D:
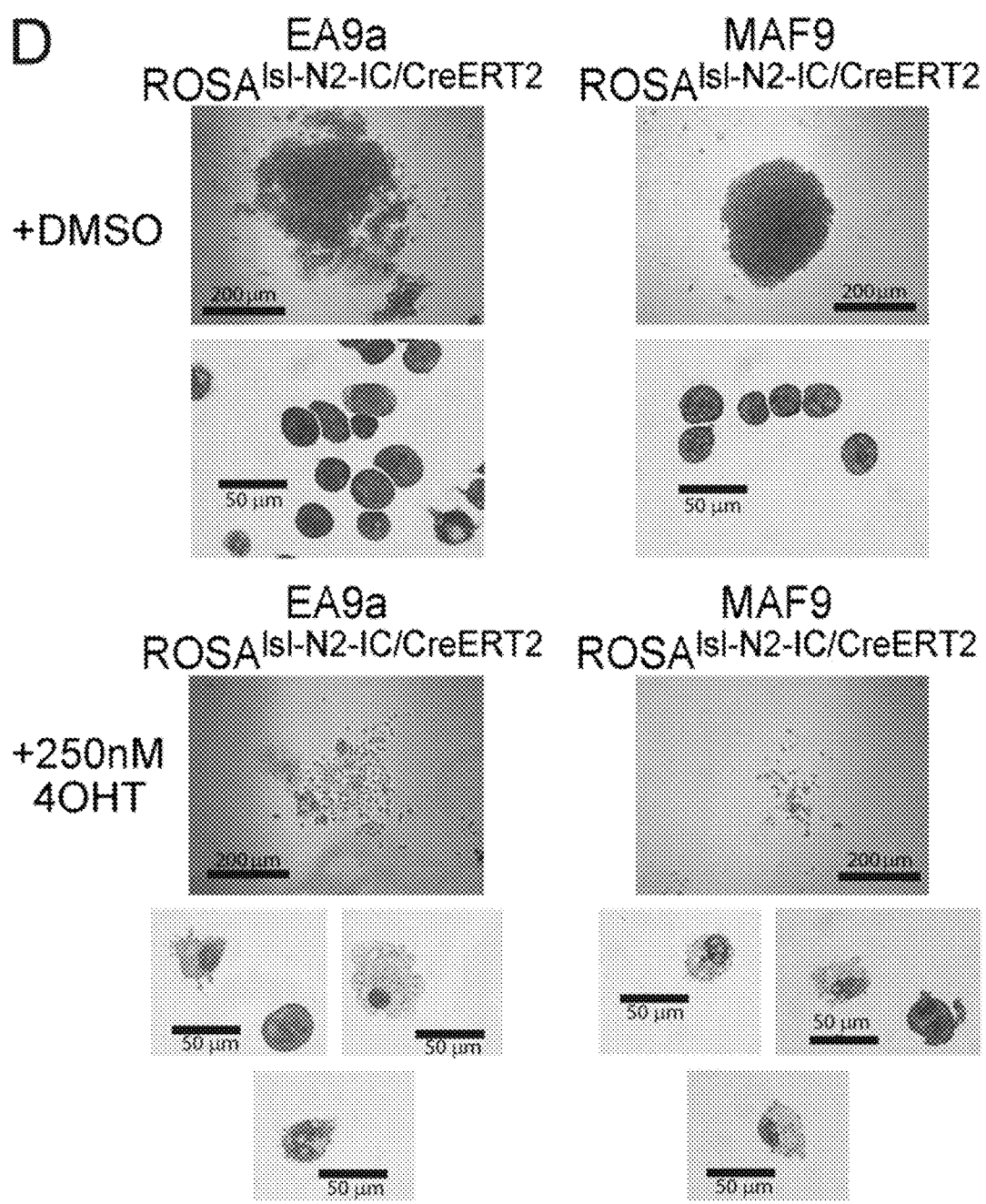
Figure 4E:
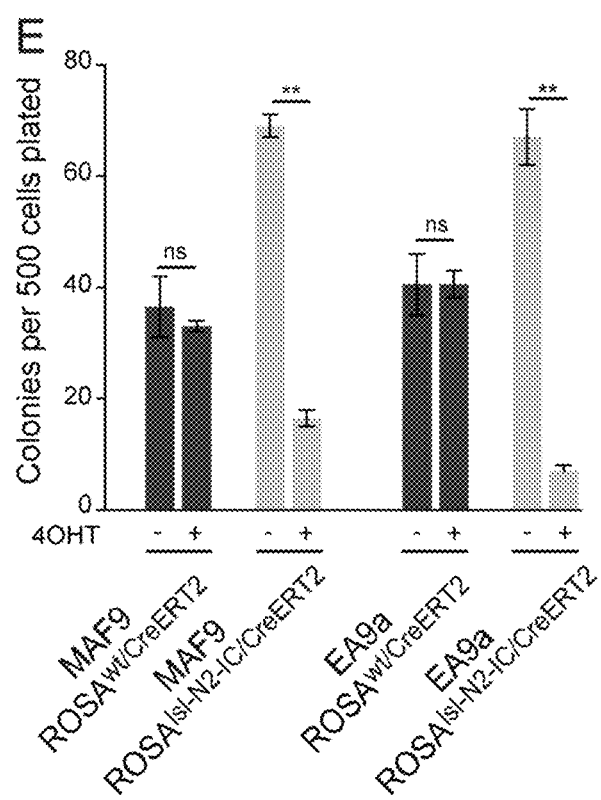

Similar experiments were realized using $ROSA^{lsl-N2-IC/CreERT2}$ bone marrow HSPC infected with MLL-AF9 or AML1-ETO (EA9a). Upon 4OHT treatment and N2-IC expression, MLL-AF9 or AML1-ETO transformed colonies lost their blast colony morphology and showed a marked significant decrease of colony number (FIG. 4D-E). Cytospin of representative colonies followed by Wright-Giemsa staining revealed that N2-IC expressing cells showed morphological changes as they likely differentiated to more mature cell fates (FIG. 4D).

Figure 5A:
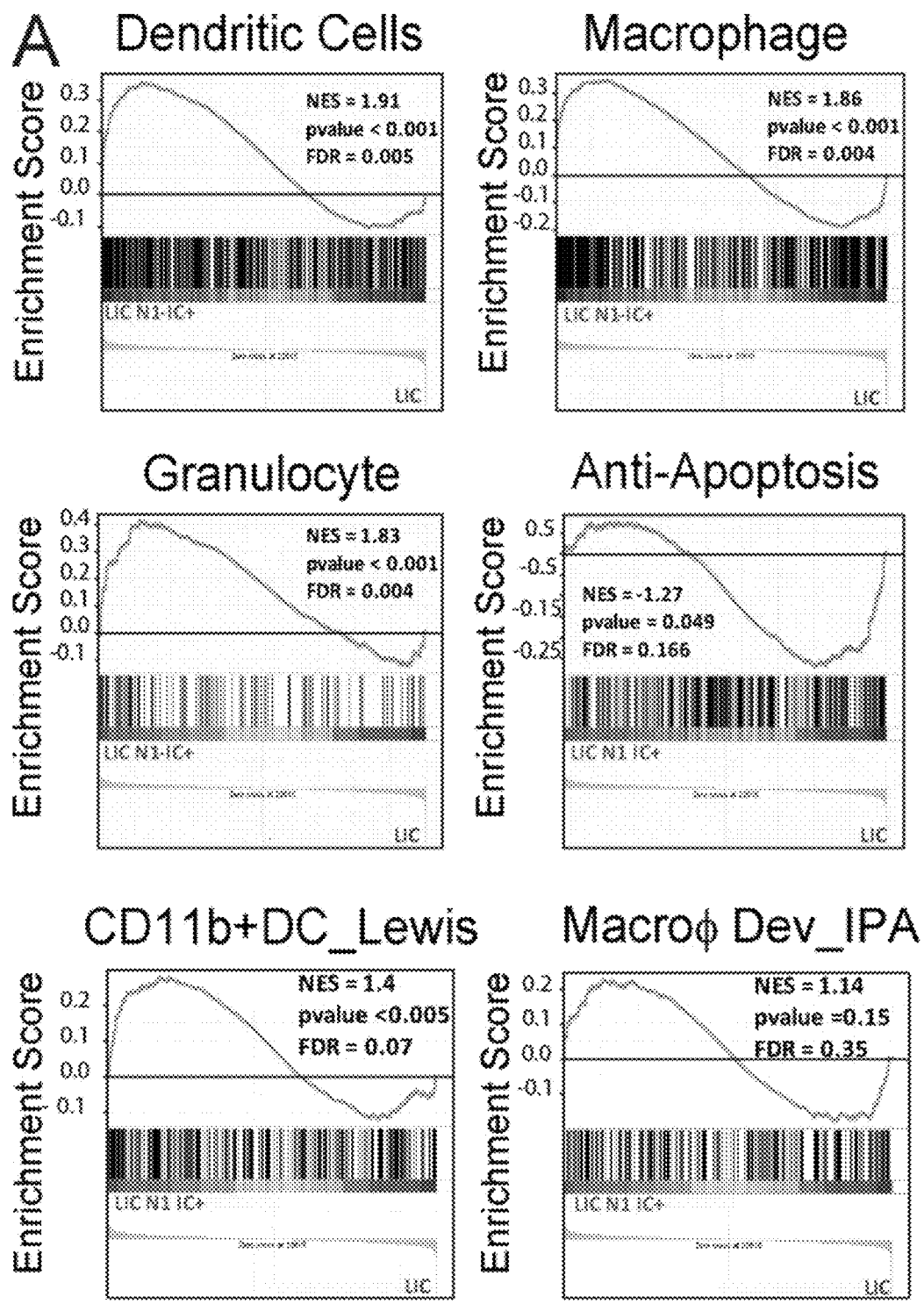

To further investigate Notch-induced AML LIC differentiation, LIC from $EF1\alpha^{wt/lsl-N1-IC}$ $ROSA^{wt/CreERT2}$ and $ROSA^{wt/CreERT2}$ mice were flow-purified 6 days post Tamoxifen administration and subjected to gene expression analysis. GeneSet Enrichment Analysis (GSEA) revealed that gene signatures characteristic of macrophage and dendritic cell differentiation were significantly enriched in LIC expressing NOTCH1-IC (FIG. 5A-B). In addition, unsupervised hierarchical clustering using significantly differentially expressed genes showed that LIC purified from NOTCH1-IC$^+$ mice cluster closer to spleen macrophages than to control LIC (FIG. 5C). Further GSEA analysis revealed that LIC expressing NOTCH1-IC downregulate genes associated with anti-apoptotic processes (FIG. 5A). Microarray results were validated by quantitative RT-PCR, which confirmed upregulation of genes associated with differentiation (Adamdec1, Cd74, Mmp9, Itgax) and Notch signaling (Hes1) and, interestingly, down-regulation of Bcl2, a key anti-apoptotic effector (FIG. 5D), recently proposed to play an important role for the propagation of AML (Vo et al., "Relative Mitochondrial Priming of Myeloblasts and Normal HSCs Determines Chemotherapeutic Success in AML," *Cell* 151:344-355 (2012), which is hereby incorporated by reference in its entirety). These studies demonstrated that Notch signaling activation is able to induce differentiation of the AML leukemia-initiating population towards the macrophage and/or dendritic cell lineages, eventually leading to cell death and disease regression in vivo.

Example 5

Recombinant Notch Ligands are Able to Target Mouse and Human AML Cells

Figures 6A, 6B:
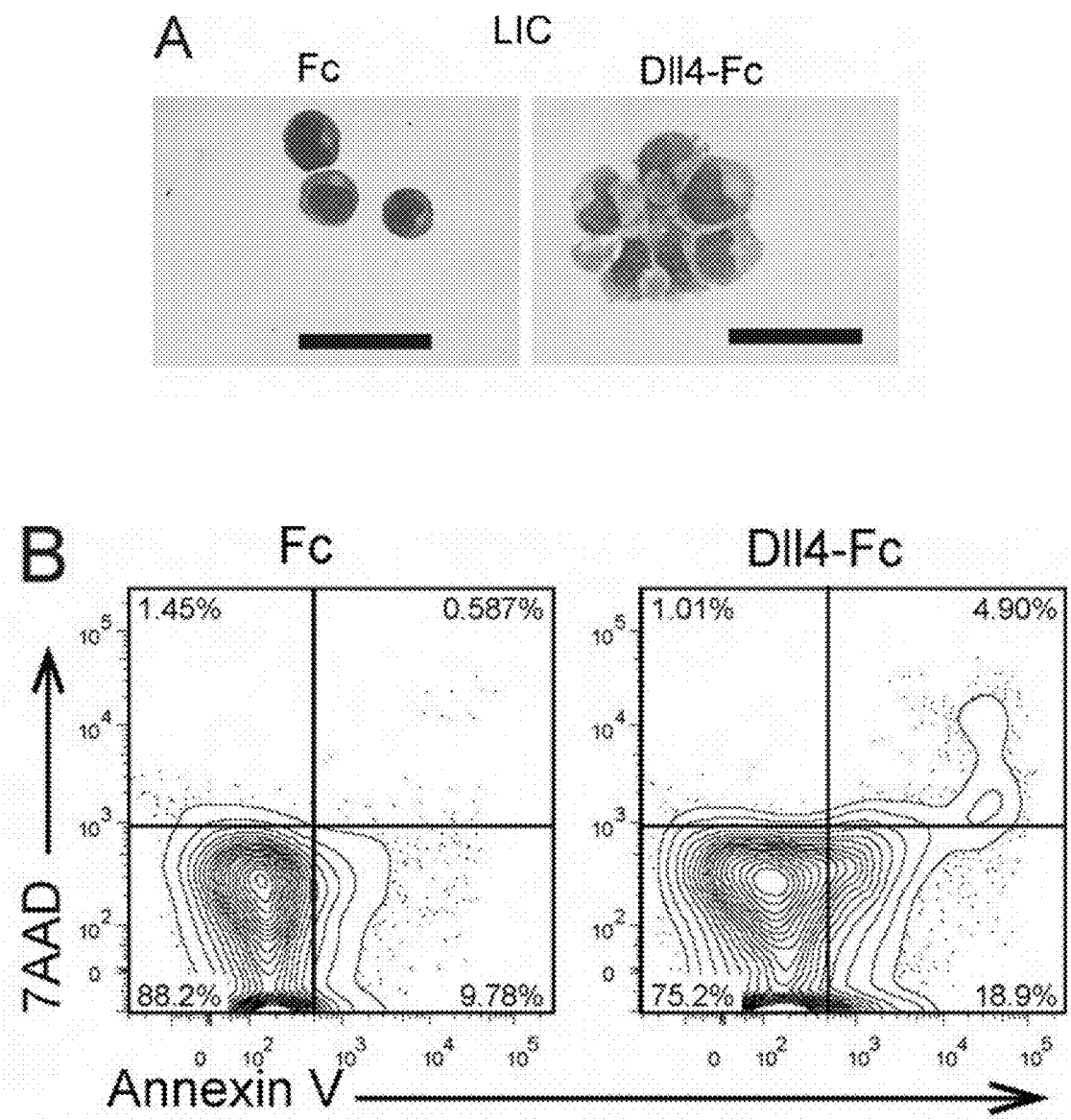
FIGS. 6A-6H demonstrate that recombinant Dll4-Fc ligand mediated Notch activation induces differentiation and apoptosis of AML LIC in vitro.
Figures 6C, 6D, 6E, 6F, 6G, 6H:
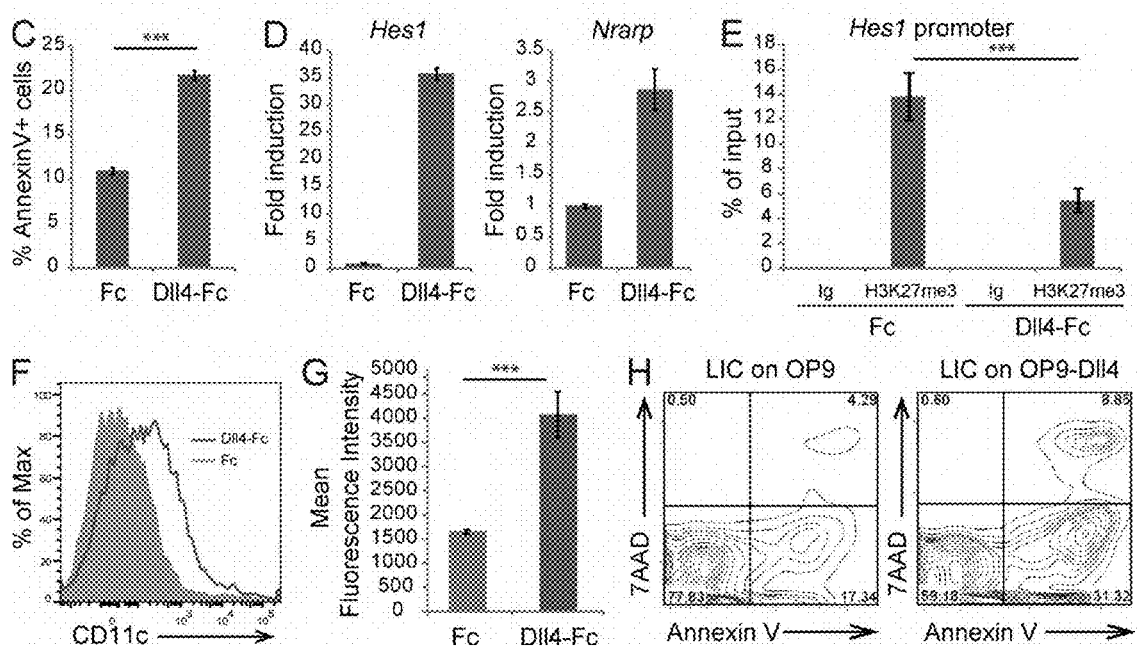

The observation that AML primary samples as well as AML mouse cells express NOTCH2 receptor on the surface suggested that exogenous activation of Notch signaling could be achieved using Notch receptor ligands/agonists. To test this hypothesis mouse AML LIC were cultured in presence of recombinant human Notch ligand Delta-like 4 extracellular domain fused to the IgG-Fc fragment (Dll4-Fc) or with control IgG-Fc. Twenty four hours after culture initiation, Dll4-Fc treated LIC showed significant changes in cell morphology characteristic of cell differentiation. Wright-Giemsa staining showed increased presence of differentiated macrophages and dendritic cells in Dll4-Fc treated cultures (FIG. 6A). Cell cycle analysis using Ki67/DAPI staining showed a marked decrease in the proportion of actively cycling cells and a significant increase in cells in G0 and G1 phases of cell cycle. AnnexinV/7AAD staining revealed a significant increase of Annexin-V positive cells when stimulated with Dll4-Fc, indicating cell death (FIG. 6B-C). Notch signaling pathway activation was further confirmed by qPCR showing strong induction of the canonical target genes Hes1 and Nrarp upon Dll4-Fc stimulation (FIG. 6D). These changes in expression were accompanied by loss of the repressive mark H3K27me3 at the promoter of the Hes1 gene (FIG. 6E). Finally, cell surface FACS analysis showed upregulation of the dendritic cell marker CD11c, further confirming induced differentiation in response to Notch ligand treatment (FIG. 6F-G). These results using recombinant ligand stimulation were further confirmed using co-cultures with OP9 stromal cells expressing Delta-like 4 (Dll4) murine Notch ligand. Co-culture of freshly purified LIC with OP9-Dll4 lead to significantly increased apoptosis within 48 h following culture initiation when compared to control co-cultures on OP9 cells (FIG. 6H).

Figures 7A, 7B, 7C, 7D, 7E, 7F, 7G, 7H:
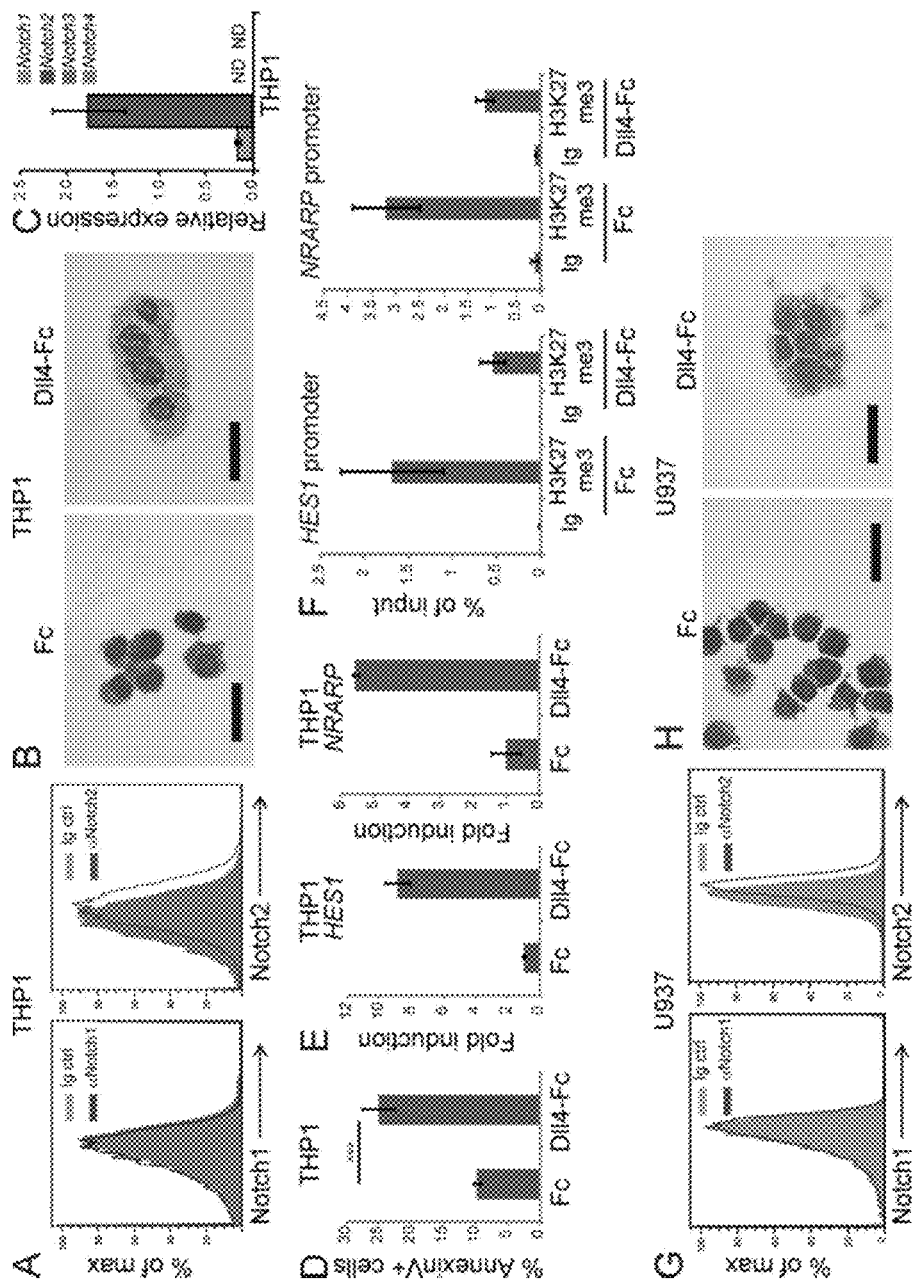
Figures 7O, 7P:
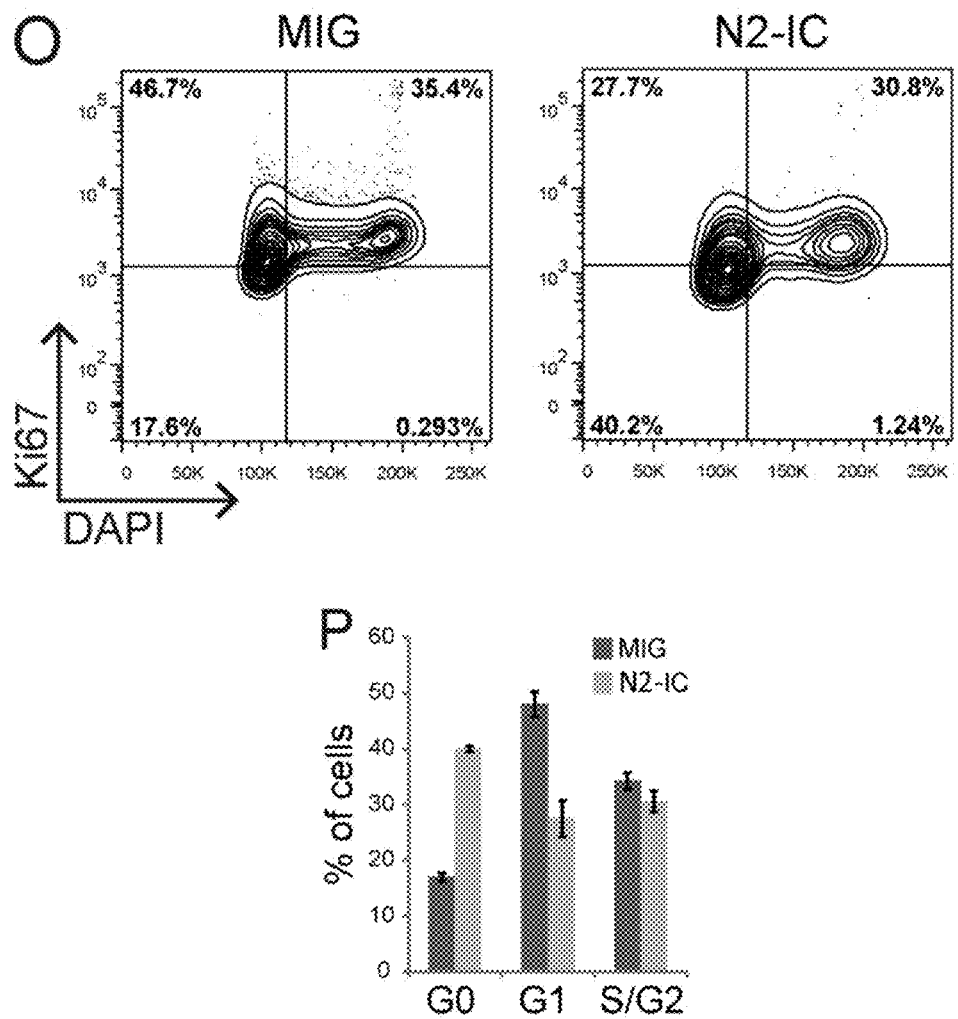

Whether Dll4-Fc-mediated stimulation could also impact human AML cells was examined next. Notch receptor expression in THP1 and U937 AML cell lines was investigated by quantitative RT-PCR and extracellular antibody staining. These cells expressed NOTCH2 mRNA and protein but no other Notch receptors or downstream targets (FIG. 7A, C and FIG. 7G). Human AML cell lines THP1 and U937 were then cultured in presence of Dll4-Fc or control IgG-Fc for 48 h. Dll4-Fc treatment induced apoptosis of cell lines (FIGS. 7D and I). Morphological observations showed similar trends for cell differentiation as previously observed in the treatment of mouse LIC (FIGS. 7B and H). To address if these effects were specific of Notch activation in myeloid cells and not global toxicity of Notch ligand, the Notch-independent T-ALL cell line Loucy was stimulated with Dll4-Fc or Fc control. Dll4-Fc stimulation was able to induce Hes1 expression (FIG. 7L) but failed to induce apoptosis in this cell line (FIG. 7K). These results show that Dll4-Fc mediated Notch activation induces AML cell lines differentiation and apoptosis. Finally, to further prove that these phenotypes are caused by the direct activation of the Notch pathway activated forms of Notch2 (NOTCH2-IC) were retroviraly expressed in THP1. In agreement to all other findings, Notch pathway activation led to significant THP1 cell cycle arrest and apoptosis induction (FIG. 7M-7P).

Figure 8A:
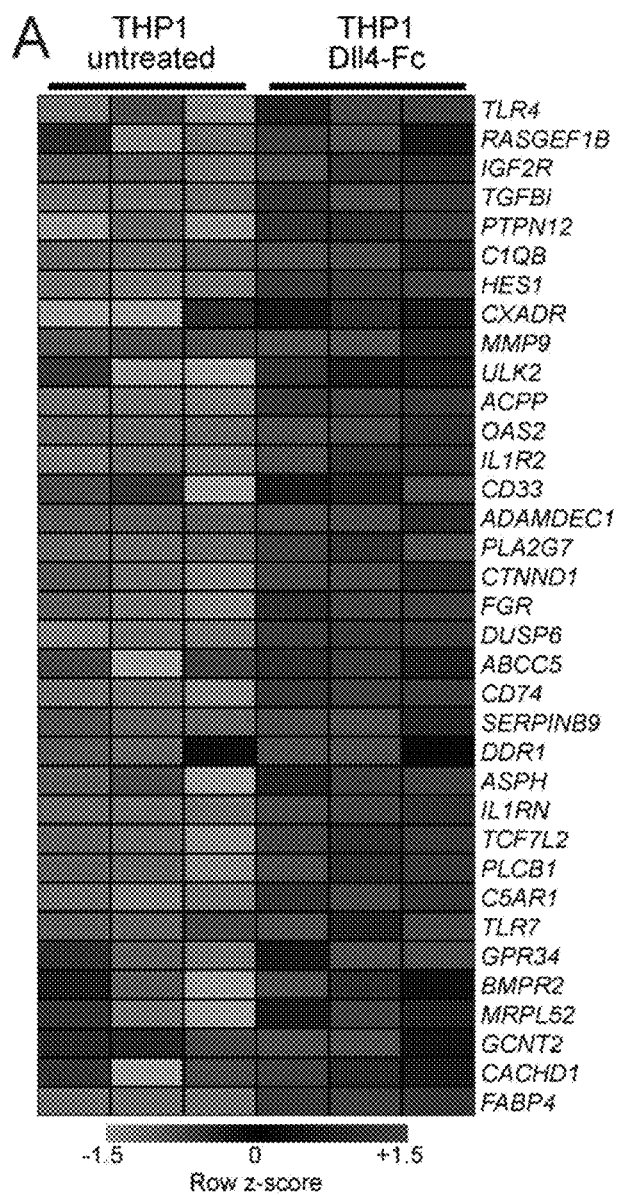
FIGS. 8A-8G demonstrate that recombinant Dll4-Fc ligand mediated Notch activation induces differentiation associated genes in THP1 cells, and differentiation and apoptosis of primary AML cells in vitro.
Figure 8B:
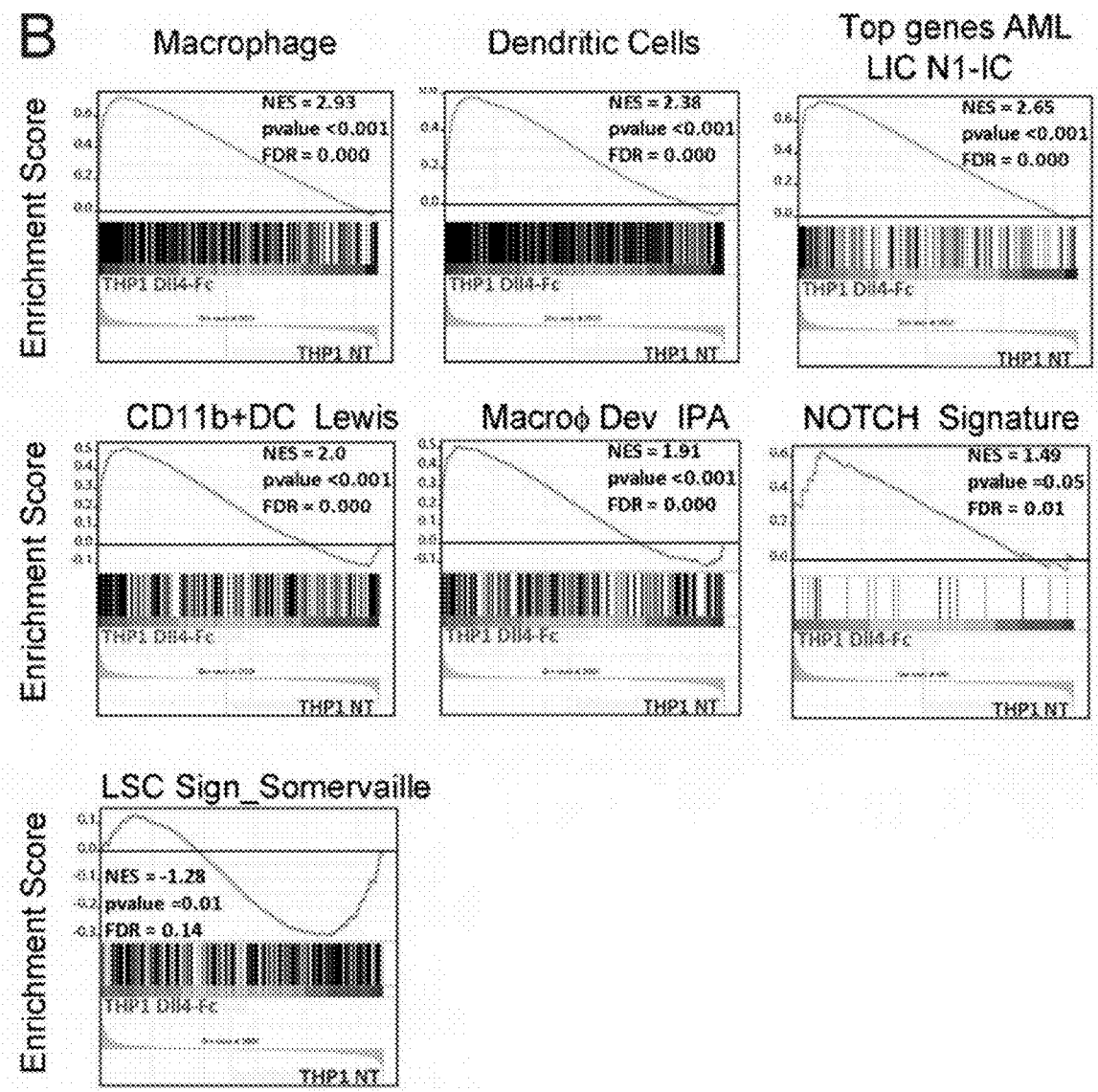
Figures 8C, 8D, 8E:
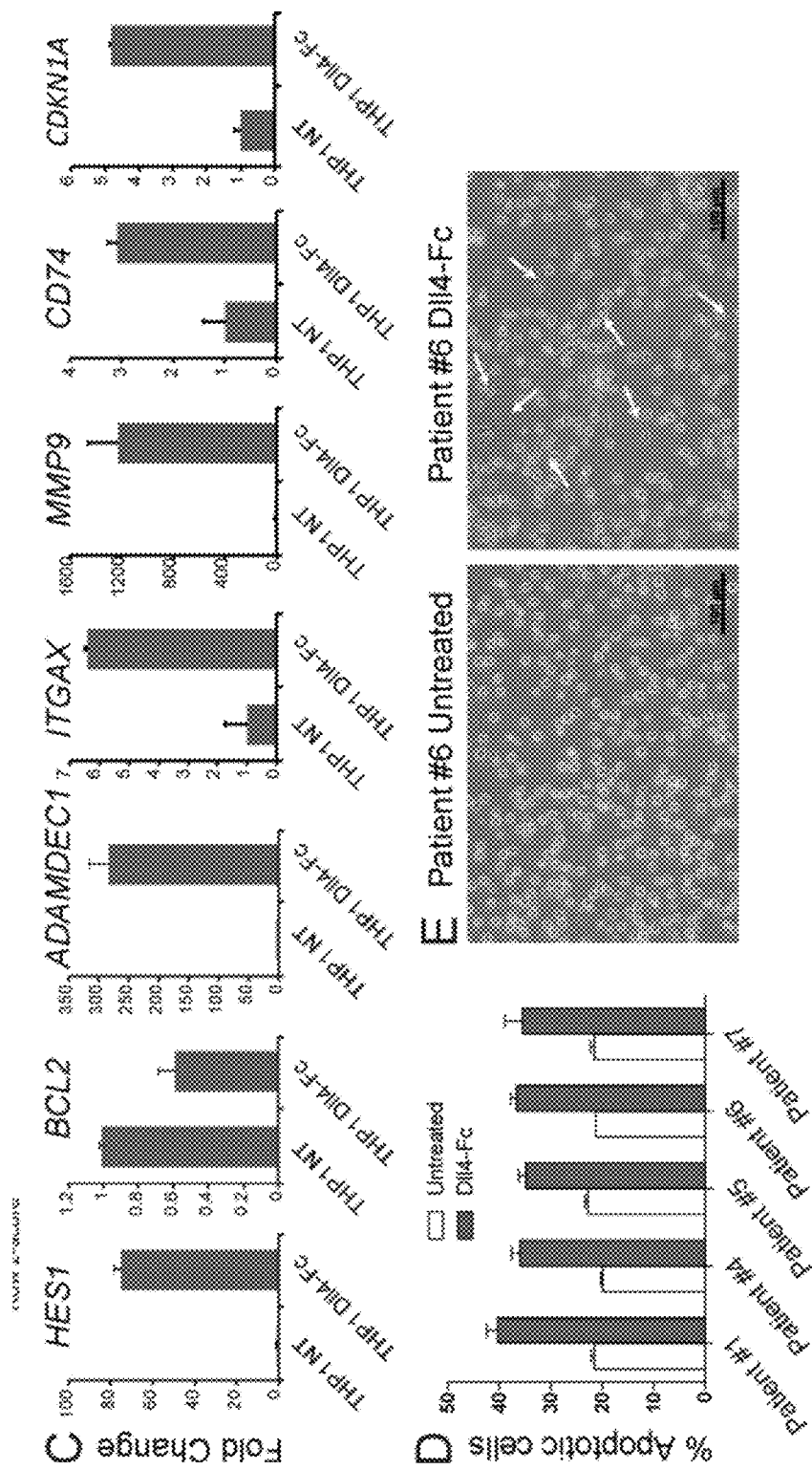

To gain further insight into mechanisms responsible of AML cell differentiation and apoptosis, whole transcriptome profiling of untreated or Dll4-Fc treated THP1 AML cells was performed. As observed previously for in vivo purified mouse AML LIC expressing NOTCH1-IC, GSEA analysis showed that THP1 treated with Dll4-Fc possess upregulated gene signatures associated with macrophage and dendritic cells differentiation (FIGS. 8A-8B) and downregulated gene signatures associated with leukemic stem cell maintenance. Interestingly, THP1 cells treated with Dll4-Fc and mouse LIC purified after in vivo Notch pathway activation, shared common gene expression signatures, suggesting a high degree of conservation between mouse and human AML cellular response to Notch agonists (FIG. 8B, Geneset "Top genes AML LIC N1-IC"). Microarray results were further validated using quantitative RT-PCR. In agreement with previous results using mouse LIC expressing NOTCH1-IC, THP1 AML cells treated with Dll4-Fc upregulated differentiation associated genes (ADAMDEC1, CD74, MMP9, ITGAX) and downregulated BCL2 (FIG. 8C). Interestingly, THP1 treated with Dll4-Fc also significantly upregulated the cell cycle inhibitor p21 (CDKN1A).

Example 6

Figures 8F, 8G:
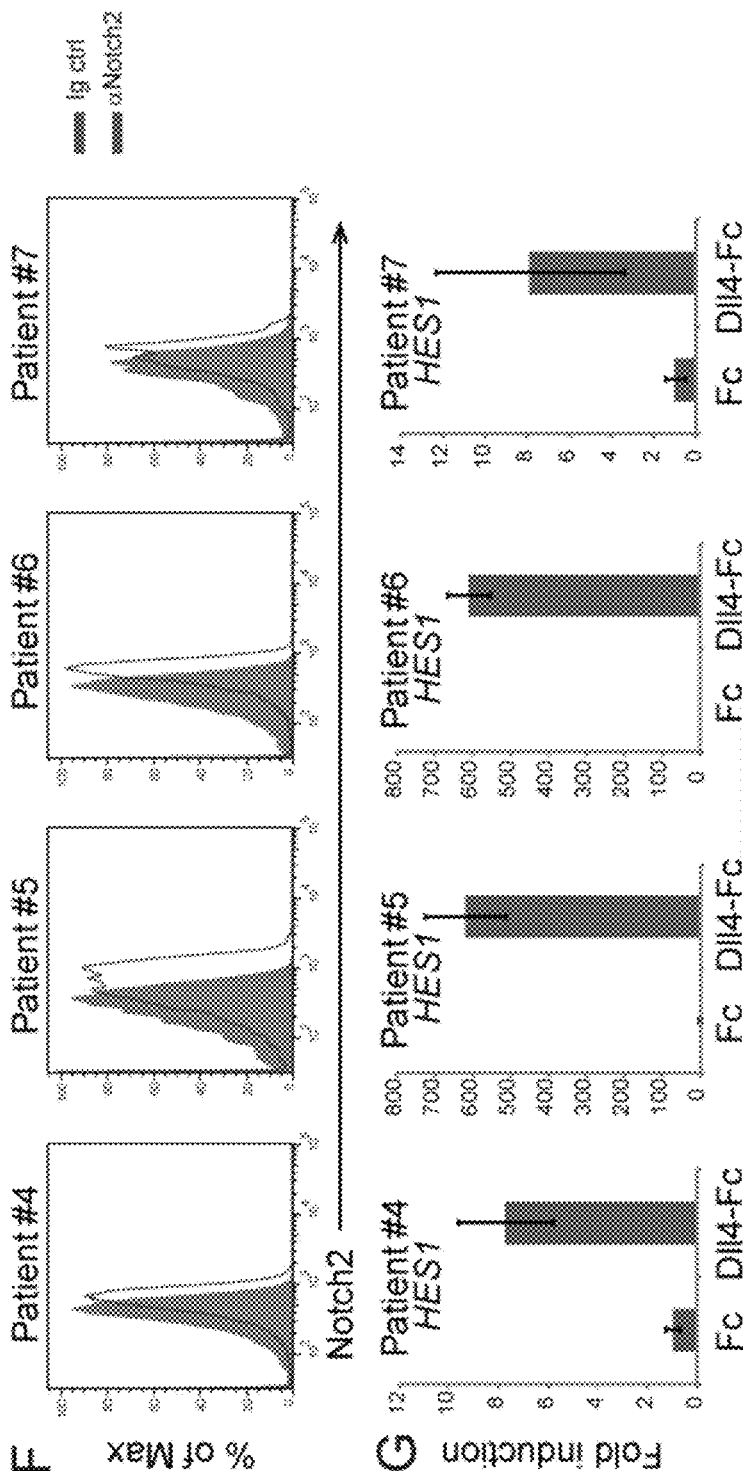

Notch Reactivation Induces Human Primary AML Sample Differentiation and Apoptosis These promising results using Notch ligand stimulation of murine and human AML cell lines prompted testing to determine whether primary cells from AML patients could be similarly affected. AML samples from different subtypes (Table 4) were cultured in the presence of Dll4-Fc or control vehicle in SFEM medium supplemented with cytokines for 24 hours. Apoptosis state was then monitored using Annexin V FACS staining. Samples treated with Dll4-Fc showed significant increase in levels of AnnexinV staining suggesting increased programmed cell death (FIG. 8D). Additionally some samples showed altered morphology as already observed for mouse LIC or THP1 stimulated with Dll4-Fc (FIG. 8E). NOTCH2 receptor surface expression was confirmed by antibody staining followed by flow cytometry analysis (FIG. 8F) and activation of Notch signaling pathway was confirmed by qPCR showing strong induction of the canonical target gene HES1 (FIG. 8G). These results show that Notch activation using recombinant ligand can induce differentiation and apoptosis in AML patient cells.

Example 7

Combined Notch and Tet2 Inactivation Leads to AML-Like Disease In Vivo

Figures 9A, 9B, 9C, 9D:
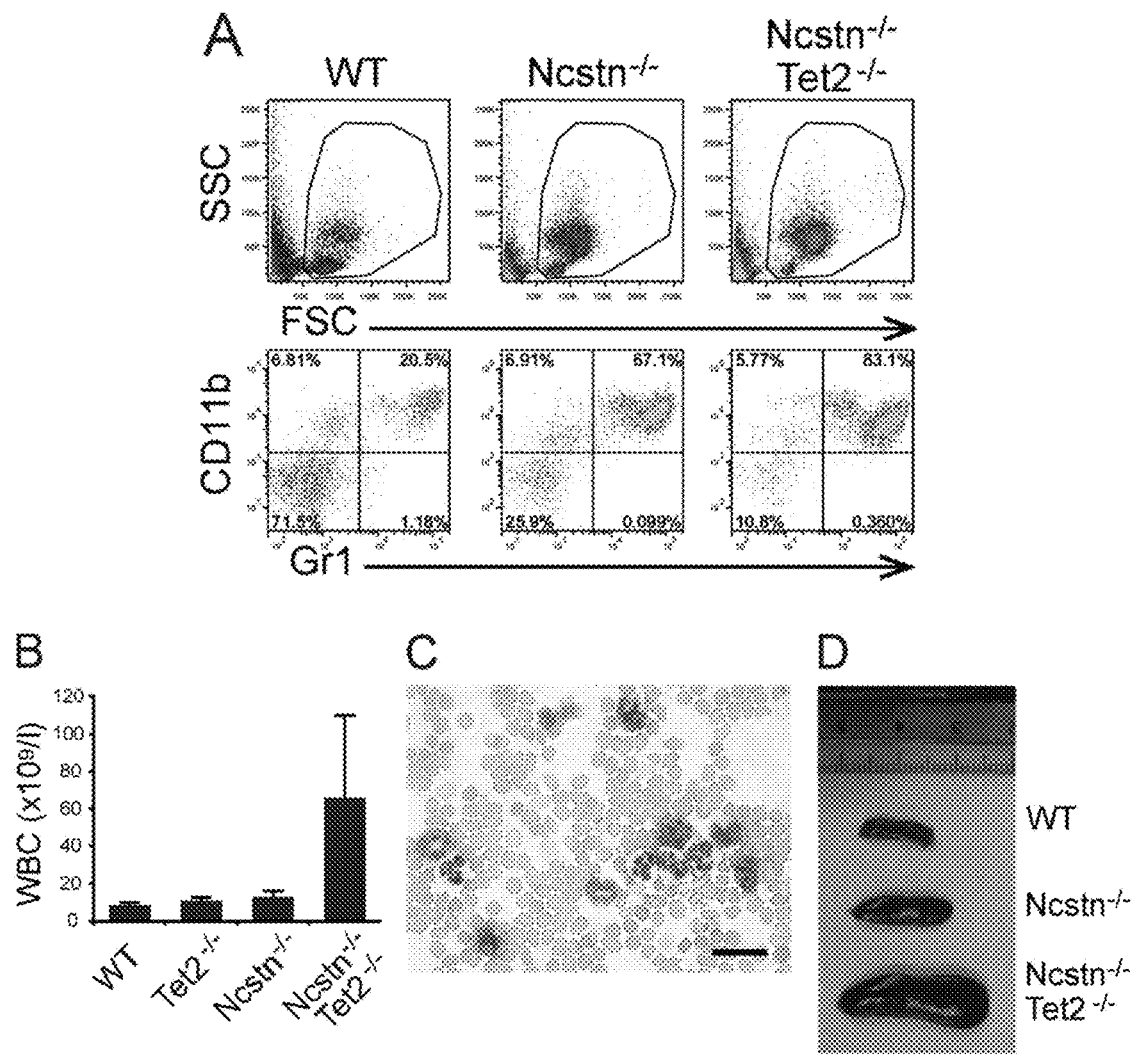
FIGS. 9A-9L show that Notch loss of function cooperates with Tet2 loss of function to induce AML in vivo.

All of the studies described herein demonstrate a novel tumor suppressor function for Notch signaling in AML. Recent studies have shown that Notch inactivation leads to a CMML-like myeloproliferative disease (MPN) but is not sufficient to induce AML (Klinakis et al., "A Novel Tumour-Suppressor Function for the Notch Pathway in Myeloid Leukaemia," Nature 473:230-233 (2011), which is hereby incorporated by reference in its entirety). It was hypothesized that loss of Notch signaling might collaborate with other oncogenic lesions to induce AML. It was previously observed that 80% of CMML patients carrying Notch pathway mutations also harbor inactivating mutations in the Ten-Eleven Translocation 2 (TET2) gene, frequently mutated in MPN and AML (Abdel-Wahab et al., "Genetic Characterization of TET1, TET2, and TET3 Alterations in Myeloid Malignancies," Blood 114:144-147 (2009); Delhommeau et al., "Mutation in TET2 in Myeloid Cancers," N. Engl. J. Med. 360:2289-2301 (2009); Langemeijer et al., "TET Proteins in Malignant Hematopoiesis," Cell Cycle 8:4044-4048 (2009), which are hereby incorporated by reference in their entirety). The potential functional collaboration of the two genetic events was then investigated. It has recently been shown that genetic inactivation of Tet2 in mice also leads to a CMML-like disease, but not overt AML, in the first 6-10 months after gene deletion (Ko et al., "Ten-Eleven-Translocation 2 (TET2) Negatively Regulates Homeostasis and Differentiation of Hematopoietic Stem Cells in Mice," Proc. Nat'l. Acad. Sci. U.S.A. 108:14566-14571 (2011); Li et al., "Deletion of Tet2 in Mice Leads to Dysregulated Hematopoietic Stem Cells and Subsequent Development of Myeloid Malignancies," Blood 118:4509-4518 (2011); Moran-Crusio et al., "Tet2 Loss Leads to Increased Hematopoietic Stem Cell Self-Renewal and Myeloid Transformation," Cancer Cell 20:11-24 (2011); Quivoron et al., "TET2 Inactivation Results in Pleiotropic Hematopoietic Abnormalities in Mouse and is a Recurrent Event During Human Lymphomagenesis," Cancer Cell 20:25-38 (2011), which are hereby incorporated by reference in their entirety). To address whether Notch and Tet2 loss of function could collaborate to induce AML in vivo compound knock-out animals (Ncstn$^{f/f}$ Tet2$^{f/f}$) were generated. Deletion of Ncstn and Tet2 was induced using the hematopoietic specific Vav1-cre deleter strain (Stadtfeld and Graf, "Assessing the Role of Hematopoietic Plasticity for Endothelial and Hepatocyte Development by Non-Invasive Lineage Tracing," Development 132:203-213 (2005), which is hereby incorporated by reference in its entirety). Peripheral blood analysis of Ncstn$^{-/-}$Tet2$^{-/-}$ mice at 7 weeks after birth showed a significant increase in whole white blood cell counts and absolute number of myelo-monocytic cells (CD11b$^+$/Gr1$^+$) (FIG. 9A,B), whereas Tet2$^{-/-}$ and Ncstn$^{-/-}$ control animals showed no signs of induced disease at this early time point (FIG. 9B). Differential counts using Wright-Giemsa stained peripheral blood smears revealed a high proportion (>20%) of blast-like cells (FIG. 9C), whereas only differentiated monocytes and granulocytes could be observed in Ncstn$^{-/-}$ or Tet2$^{-/-}$ single knock-out animals (Klinakis et al., "A Novel Tumour-Suppressor Function for the Notch Pathway in Myeloid Leukaemia," Nature 473: 230-233 (2011); Moran-Crusio et al., "Tet2 Loss Leads to Increased Hematopoietic Stem Cell Self-Renewal and Myeloid Transformation," Cancer Cell 20:11-24 (2011), which are hereby incorporated by reference in their entirety).

Figures 9E, 9F:
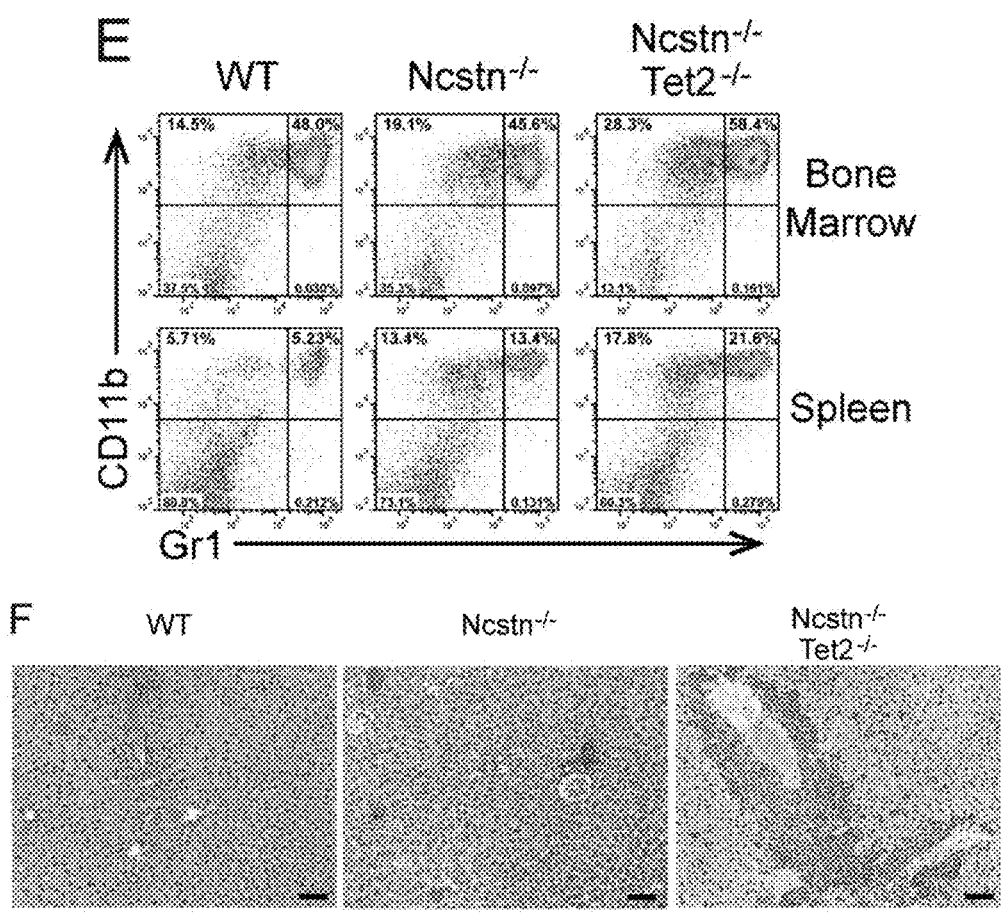
Figures 9G, 9H, 9I:
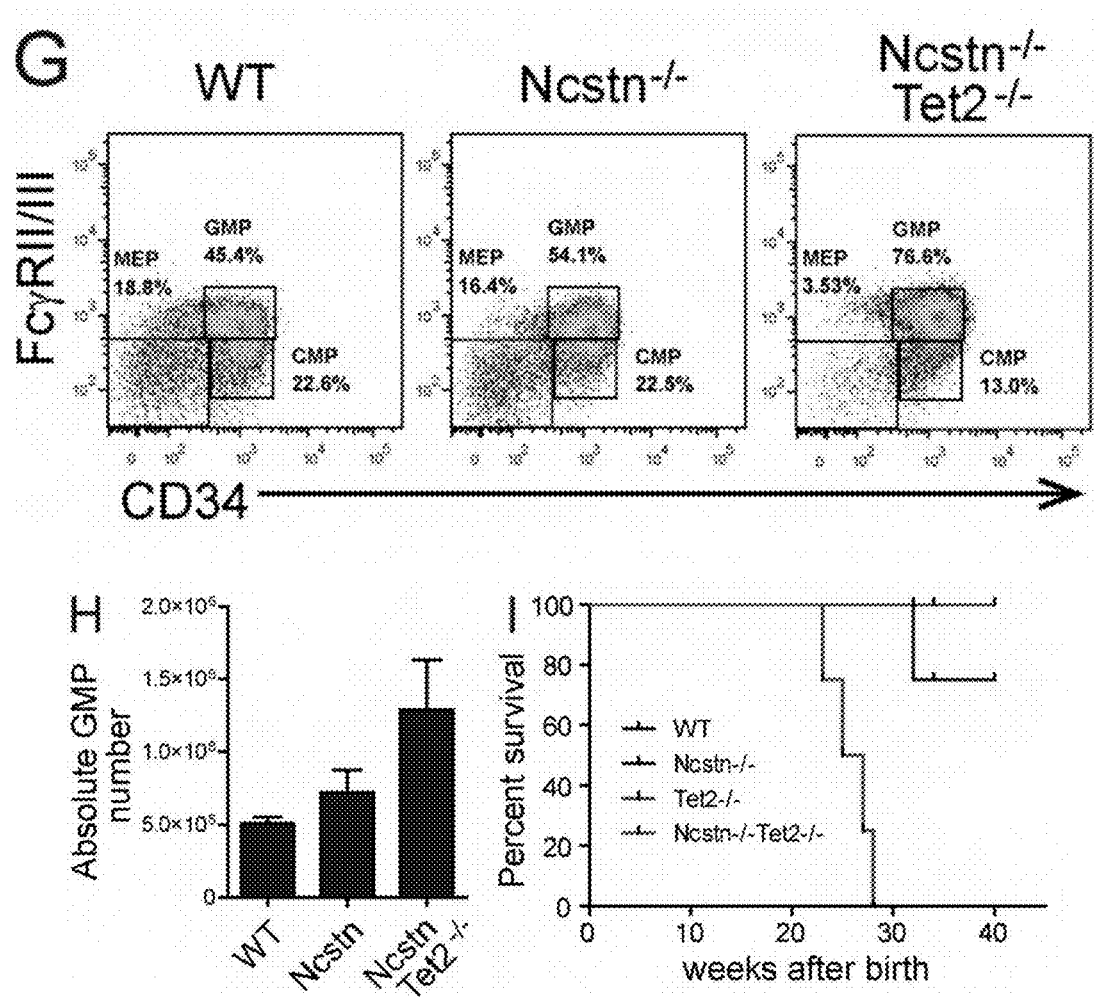
Figures 9J, 9K, 9L:
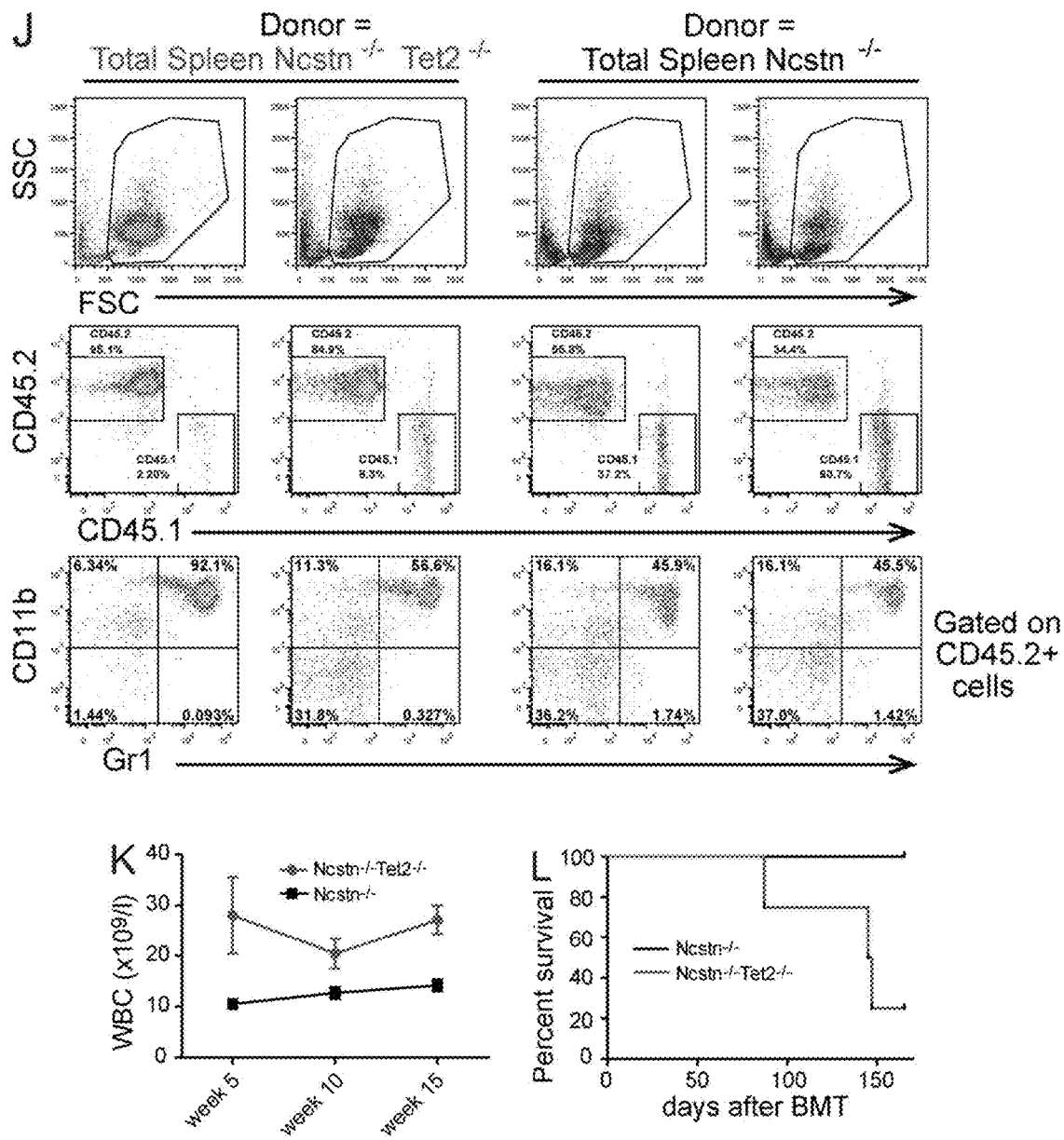

Ncstn$^{-/-}$Tet2$^{-/-}$ compound animals presented with significantly enlarged spleens (FIG. 9D) and histological and FACS analysis of tissues showed massive infiltration of both differentiated and blast-like myeloid cells (FIG. 9E-F). Detailed FACS analysis of bone marrow myeloid progenitor compartment showed enlargement of GMP compartment in both relative proportion and absolute number (FIG. 9G-H). Ncstn$^{-/-}$Tet2$^{-/-}$ compound animals eventually died after an average of 26 weeks after birth whereas most of the WT, Ncstn$^{-/-}$ and Tet2$^{-/-}$ littermates survived (FIG. 9I). To address whether the induced disease is transplantable, total spleen tumor cells from Ncstn$^{-/-}$Tet2$^{-/-}$ or Ncstn$^{-/-}$ littermate mice (used as control) were transplanted in lethally irradiated congenic recipient mice together with a radioprotective dose of wild type bone marrow. Despite myeloid bias that was cell-autonomous (FIG. 9J), Ncstn$^{-/-}$ cells failed to induce lethal disease in transplanted mice. Ncstn$^{-/-}$Tet2$^{-/-}$ splenocytes outcompeted wild type support bone marrow and led to elevated blood counts, starting as early as 5 weeks after transplantation (FIG. 9K). Approximately 75% of animals transplanted with Ncstn$^{-/-}$Tet2$^{-/-}$ splenocytes died within 150 days post transplantation whereas animals transplanted with Ncstn$^{-/-}$ splenocytes showed increased myeloid cells counts in peripheral blood but did not develop lethal myeloid leukemia (FIG. 9L). These results demonstrate that Notch signaling can function as a tumor suppressor as, when silenced can co-operate with additional genetic lesions and lead to the rapid induction of transplantable myeloid disease reminiscent of human AML.

Discussion of Examples 1-7

These studies demonstrate that the Notch signaling pathway is silenced in both human and mouse AML and that this suppression is evident also in AML leukemia-initiating cells in an MLL-AF9 induced mouse model of AML as well as in stem and progenitor cell compartment of AML patient that likely contain leukemic initiating cells. Notch pathway silencing in AML is in part due to increased levels of H3K27me3 on Notch target promoters, a histone mark associated with transcriptional repression. These studies indicate that Notch pathway inactivation is mediated by reversible epigenetic silencing. Indeed, Notch pathway re-activation, either through inducible expression of Notch-IC transgenes or by treatment with Dll4-Fc fusion molecules, efficiently targets both human and mouse AML, leading to growth inhibition, differentiation and cell death. Pathway re-activation could thus be an effective therapeutic approach in AML. In agreement with this notion, the studies described herein have demonstrated that AML cells and most importantly AML-initiating cells uniformly express the NOTCH2 receptor, which allows for Notch pathway reactivation. Most importantly, Notch2-mediated pathway reactivation fails to induce T cell leukemia. This last finding conflicts with an earlier report in which virally-driven NOTCH2-IC lead to T-ALL (Witt et al., "Activated Notch2 Potentiates CD8 Lineage Maturation and Promotes the Selective Development of B1 B Cells," *Mol. Cell. Biol.* 23:8637-8650 (2003), which is hereby incorporated by reference in its entirety). However, that was an artificial system that led to non-physiological expression levels, unlike the monoallelic, Rosa26-driven model employed here which more closely mimics the physiological situation. Accordingly, reversible Notch pathway activation, through NOTCH2 receptor (i.e. using NOTCH2 specific agonistic antibodies), could indeed be a, specific, viable therapeutic approach for treating established disease and targeting AML-initiating cells that contribute to relapse disease. Similar approaches utilizing NOTCH1-activating antibodies have been previously successfully tested in animal studies of tissue regeneration (Conboy et al., Notch-Mediated Restoration of Regenerative Potential to Aged Muscle," *Science* 302:1575-1577 (2003), which is hereby incorporated by reference in its entirety).

It is unlikely that NOTCH2 expression is a "genetic switch" placed on stem and progenitor cells to merely suppress their ability to generate leukemia. Based on previous studies of Notch function in the bone marrow (Klinakis et al., "A Novel Tumour-Suppressor Function for the Notch Pathway in Myeloid Leukaemia," *Nature* 473:230-233 (2011), which is hereby incorporated by reference in its entirety), it is likely defined Notch expression levels and pathway activation can control cellular differentiation during early hematopoiesis. In agreement with this notion, Notch pathway reactivation led to ectopic differentiation of both mouse and human AML cells towards the macrophage and dendritic lineages. In agreement with these findings, key roles for the Notch pathway in the differentiation of dendritic cells from bone marrow progenitors have been suggested (Lewis et al., "Notch2 Receptor Signaling Controls Functional Differentiation of Dendritic Cells in the Spleen and Intestine," *Immunity* 35(5):780-91 (2011), which is hereby incorporated by reference in its entirety). Further mapping of Notch receptor expression and activation in the bone marrow is essential for the complete understanding of Notch-regulated programs of differentiation during early hematopoiesis.

Notch signaling inactivation can lead to myeloproliferative disease in mouse models but not overt AML. In an identical fashion, Tet2 mutations leads to similar CMML-like disease that only infrequently develops to AML. Strikingly, combinatorial silencing of both genes leads to rapid and transplantable disease reminiscent of human AML. At this point, the mechanisms of cooperation between Notch and Tet2 silencing remain elusive. However two recent studies using DNA methylation and gene expression analyses in human patient samples and a mouse model of myeloid leukemia induced by the IDH1R132H mutant show that several Notch target genes and Notch pathway genes are hyper-methylated and silenced in IDH1/2 mutant AML (Akalin et al., "Base-Pair Resolution DNA Methylation Sequencing Reveals Profoundly Divergent Epigenetic Landscapes in Acute Myeloid Leukemia," *PLoS Genet.* 8:e1002781 (2012); Sasaki et al., "IDH1(R132H) Mutation Increases Murine Haematopoietic Progenitors and Alters Epigenetics," *Nature* 488:656-659 (2012), which are hereby incorporated by reference in their entirety). As it has been shown that IDH1/2 acts upstream of Tet2 and that IDH1/2 and Tet2 mutations are mutually exclusive in AML (Figueroa et al., "Leukemic IDH1 and IDH2 Mutations Result in a Hypermethylation Phenotype, Disrupt TET2 Function, and Impair Hematopoietic Differentiation," *Cancer Cell* 18:553-567 (2010), which is hereby incorporated by reference in its entirety), one can hypothesize that IDH1/2 or Tet2 mutations will impinge on a set of Notch targets and help to either maintain their silencing or silence them further. As several Notch target genes are also under control of multiple transcription factors, hypermethylation of these genes due to IDH/Tet2 mutations could block their reactivation. This is the first demonstration of genetic co-operation between the two pathways and the first genetic event cooperating with Tet2 loss in vivo. It also suggests that targeting both the Notch pathway and disrupting the aberrant DNA methylation, characteristic of TET2 deficiency (i.e. using hypo-methylating agents) could represent a powerful combinatorial therapeutic approach in AML.

In summary, provide herein is the first example of anti-tumor activity of Notch pathway reactivation which indicates that therapeutic approaches using Notch activating ligand, agonistic Notch receptor-specific antibodies or small molecule agonists may have potent activity in the treatment of certain subtypes of AML, particularly acute myelo-monocytic leukemias by targeting AML-initiating cells. The specific surface expression of NOTCH2 could potentially maximize specificity of targeting and minimize potential side-effects. Moreover, as Notch has been recently suggested to play a tumor suppressor roles in a number of solid tumors (Agrawal et al., "Exome Sequencing of Head and Neck Squamous Cell Carcinoma Reveals Inactivating Mutations in NOTCH1," *Science* 333:1154-1157 (2011); Lobry et al., "Oncogenic and Tumor Suppressor Functions of Notch in Cancer: It's NOTCH What You Think," *J. Exp. Med.* 208:1931-1935 (2011); Stransky et al., "The Mutational Landscape of Head and Neck Squamous Cell Carcinoma," *Science* 333:1157-1160 (2011); Viatour et al., "Notch Signaling Inhibits Hepatocellular Carcinoma Following Inactivation of the RB Pathway," *J. Exp. Med.* 208:1963-1976 (2011), which are hereby incorporated by reference in their entirety), Notch receptor-specific activation could therefore constitute a novel effective therapy in a wide spectrum of human malignancies.

Example 8

Notch2 Activation Using Notch2 Agonist Antibody Induces Apoptosis of AML Cell Line THP1

The use of a Notch2 specific agonist antibody to achieve Notch2 receptor activation was examined. Anti-Human specific Notch2 antibody MHN2-25 (Haraguchi et al., "Notch Activation Induces the Generation of Functional NK Cells from Human Cord Blood CD34-Positive Cells Devoid of IL-15," *J. Immunol.* 182(10): 6168-78 (2009), which is hereby incorporated by reference in its entirety) was coated on tissue culture plates using a 5 ug/ml antibody/PBS solution. As a positive control, tissue culture plates were coated with a Dll4-Fc solution at 10 ug/ml concentration in PBS, and as a negative control, tissue culture plates were coated with a solution of unspecific mouse IgG2a antibody at 5 ug/ml concentration in PBS. Coating was done overnight at 4° C. Plates were rinsed once with cold PBS prior to culture with cells.

THP1 cells (AML cell line) were grown for 24 h on coated tissue culture plates in RPMI complemented with 10% FBS. After 24 hours in culture, cells were harvested for Annexin V/7AAD staining following manufacturer's recommendation (BD Pharmingen) and RNA extraction using RNeasy mini kit following manufacturer's instruction (Qiagen). All experiments were carried out in triplicates.

Figures 10A, 10B, 10C:
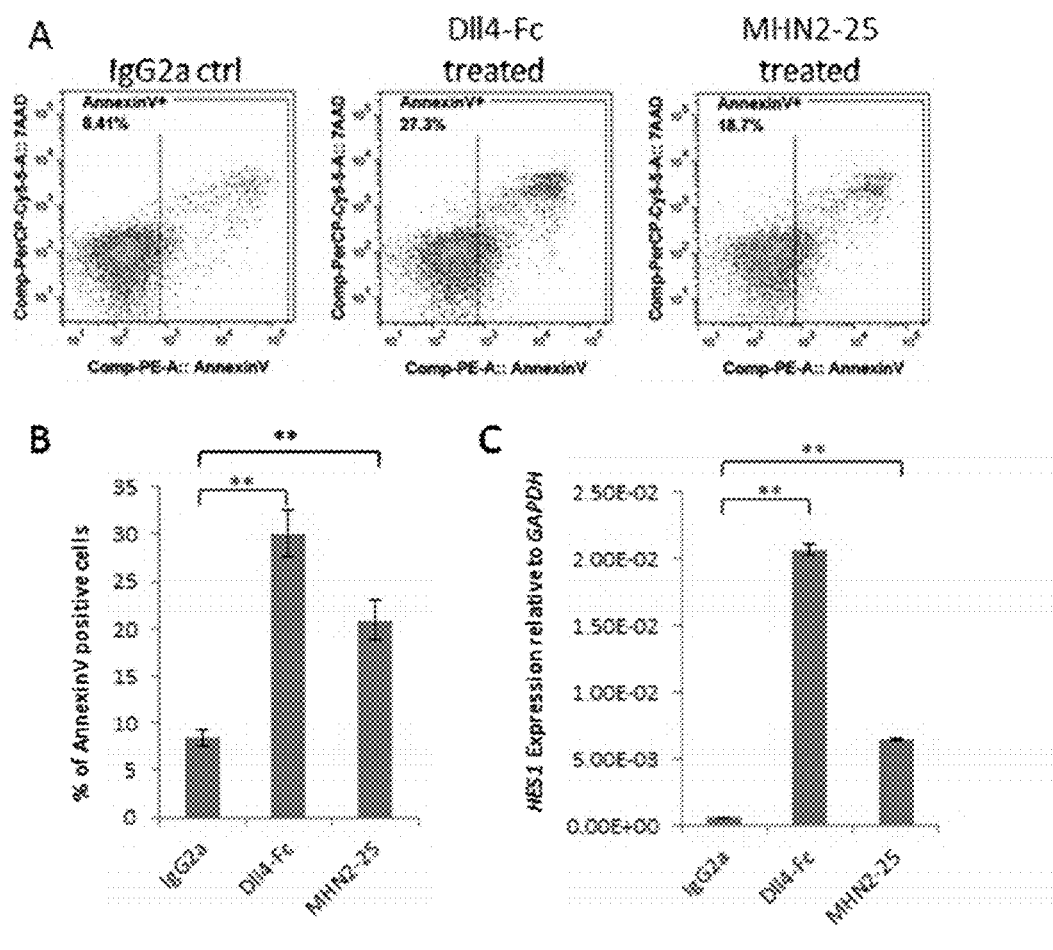
FIGS. 10A-10C show that Notch2 activation using Notch2 agonist antibody induces apoptosis of AML cell line THP1.

FACS analysis of Annexin V/7AAD staining showed an increased apoptosis level of THP1 cells following Dll4-Fc treatment as well as Notch2 agonist antibody treatment (FIGS. 10A-10B). To control that treatment induced Notch activation, cDNA was synthesized from extracted RNA using SuperScript II first strand synthesis kit following manufacturer's recommendation (Invitrogen) then quantitative RT-PCR was performed to monitor expression of well characterized Notch target gene Hes1. As previously shown, Dll4-Fc stimulation led to increased activation of Hes1 expression. Similarly, THP1 treatment with Notch2 agonist antibody also significantly increased Hes1 expression (FIG. 10C). Taken together, these results demonstrate that specific activation of the Notch2 receptor using a Notch2 agonist antibody induces Notch2 specific signaling and induce apoptosis of human AML cells.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of inducing cell differentiation and cell death in a population of acute myeloid leukemia leukemia-initiating cells (LICs), said method comprising:
   administering a Notch receptor agonist to the population of acute myeloid leukemia LICs under conditions effective to induce cell differentiation and cell death in the population of acute myeloid leukemia LICs.

2. The method of claim 1, wherein the population of acute myeloid leukemia LICs comprises a population of Lin$^-$CD34$^+$ acute myeloid leukemia cells.

3. The method of claim 1, wherein the population of acute myeloid leukemia LICs comprises a population of Lin$^-$CD34$^+$CD38$^-$ acute myeloid leukemia cells.

4. The method of claim 1, wherein the Notch receptor agonist is a Notch 1 receptor agonist, a Notch 2 receptor agonist, or a combination thereof.

5. The method of claim 1, wherein the Notch receptor agonist is a Notch receptor-activating peptide ligand, or a Notch receptor agonist antibody or active binding fragment thereof.

6. The method of claim 1, wherein the Notch receptor agonist is a Notch 2 receptor agonist antibody selected from the group consisting of an MHN2-25 antibody, an active binding fragment of the MHN2-25 antibody, an HMN2-29 antibody, and an active binding fragment of the HMN2-29 antibody.

7. The method of claim 1, wherein said administering is carried out in vivo.

8. The method of claim 1, wherein said administering is repeated periodically.

9. A method of treating acute myeloid leukemia in a subject, said method comprising:
   selecting a subject having acute myeloid leukemia and
   administering, to the selected subject, a Notch 2 receptor agonist, wherein said Notch 2 receptor agonist is an antibody or active binding fragment thereof that binds to the NRR or EGF domain of Notch 2, under conditions effective to treat the acute myeloid leukemia in the subject.

10. The method of claim 9, wherein the Notch 2 receptor agonist antibody is selected from the group consisting of an MHN2-25 antibody, an active binding fragment of the MHN2-25 antibody, an HMN2-29 antibody, and an active binding fragment of the HMN2-29 antibody.

11. The method of claim 9, wherein said administering is repeated periodically.

12. The method of claim 9, wherein said administering is carried out in combination with another acute myeloid leukemia therapy.

13. The method of claim 12, wherein the other acute myeloid leukemia therapy is selected from the group consisting of chemotherapy, stem cell transplantation therapy, a hypomethylating agent therapy, a FLT3 inhibitor therapy, a farnesyltransferase inhibitor therapy, and combinations thereof.

14. A method of inhibiting the development of acute myeloid leukemia relapse disease in a subject comprising:
   selecting a subject having had acute myeloid leukemia and
   administering, to the selected subject, a Notch receptor agonist under conditions effective to inhibit the development of acute myeloid leukemia relapse disease in the subject.

15. The method of claim 14, wherein the selected subject is in complete remission of acute myeloid leukemia.

16. The method of claim 14, wherein the selected subject has a measurable amount of minimal residual disease.

17. The method of claim 14, wherein the Notch receptor agonist is a Notch 1 receptor agonist, a Notch 2 receptor agonist, or a combination thereof.

18. The method of claim 14, wherein the Notch receptor agonist is a Notch receptor-activating peptide ligand or a Notch receptor agonist antibody or active binding fragment thereof.

19. The method of claim 14, wherein the Notch receptor agonist is a Notch 2 receptor agonist antibody selected from the group consisting of an MHN2-25 antibody, an active binding fragment of the MHN2-25 antibody, an HMN2-29 antibody, and an active binding fragment of the HMN2-29 antibody.

20. The method of claim 14, wherein said administering is carried out in combination with another acute myeloid leukemia therapy.

21. The method according to claim 20, wherein the other acute myeloid leukemia therapy is selected from the group consisting of chemotherapy, stem cell transplantation therapy, a hypomethylating agent therapy, a FLT3 inhibitor therapy, a farnesyltransferase inhibitor therapy, and combinations thereof.

* * * * *

UNITED STATES PATENT AND TRADEMARK OFFICE
CERTIFICATE OF CORRECTION

PATENT NO. : 9,683,039 B2
APPLICATION NO. : 14/212418
DATED : June 20, 2017
INVENTOR(S) : Aifantis et al.

It is certified that error appears in the above-identified patent and that said Letters Patent is hereby corrected as shown below:

In the Specification

Column 1 at Lines 7-10, delete "This invention was made with government support under grant number 5R01CA105129 awarded by the National Institutes of Health. The government has certain rights in this invention." and insert --This invention was made with government support under P30 CA016087, R01 CA133379, R01 GM0888, R01 CA105129, and R21 CA141399 awarded by National Institutes of Health. The government has certain rights in the invention.--

Signed and Sealed this
Twenty-first Day of August, 2018

Andrei Iancu
*Director of the United States Patent and Trademark Office*

SEQUENCE LISTING

```
<160> NUMBER OF SEQ ID NOS: 59

<210> SEQ ID NO 1
<211> LENGTH: 2555
<212> TYPE: PRT
<213> ORGANISM: Homo sapiens

<400> SEQUENCE: 1

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
                20                  25                  30

Asn Gly Gly Lys Cys Glu Ala Ala Asn Gly Thr Glu Ala Cys Val Cys
            35                  40                  45

Gly Gly Ala Phe Val Gly Pro Arg Cys Gln Asp Pro Asn Pro Cys Leu
        50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160
```

```
Ser Tyr Ile Cys His Cys Pro Pro Ser Phe His Gly Pro Thr Cys Arg
            165                 170                 175

Gln Asp Val Asn Glu Cys Gly Gln Lys Pro Gly Leu Cys Arg His Gly
        180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
        210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
            245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
            275                 280                 285

Gly Gln Tyr Cys Thr Glu Asp Val Asp Glu Cys Gln Leu Met Pro Asn
        290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
            325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
            355                 360                 365

Leu Cys His Leu Asn Asp Ala Cys Ile Ser Asn Pro Cys Asn Glu Gly
            370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
                420                 425                 430

Leu Gly Ser Phe Glu Cys Gln Cys Leu Gln Gly Tyr Thr Gly Pro Arg
                435                 440                 445

Cys Glu Ile Asp Val Asn Glu Cys Val Ser Asn Pro Cys Gln Asn Asp
            450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
                500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
        530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575
```

```
Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
        835                 840                 845

Asp Tyr Glu Ser Phe Ser Cys Val Cys Pro Thr Gly Trp Gln Gly Gln
    850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
            900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Arg Gly Thr Phe Cys Glu Glu
    930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
            980                 985                 990

Phe Asn Gly Gly Thr Cys Val Asp  Gly Ile Asn Ser Phe  Thr Cys Leu
```

```
                995              1000            1005
Cys Pro Pro Gly Phe Thr Gly Ser Tyr Cys Gln His Asp Val Asn
    1010            1015            1020

Glu Cys Asp Ser Gln Pro Cys Leu His Gly Gly Thr Cys Gln Asp
    1025            1030            1035

Gly Cys Gly Ser Tyr Arg Cys Thr Cys Pro Gln Gly Tyr Thr Gly
    1040            1045            1050

Pro Asn Cys Gln Asn Leu Val His Trp Cys Asp Ser Ser Pro Cys
    1055            1060            1065

Lys Asn Gly Gly Lys Cys Trp Gln Thr His Thr Gln Tyr Arg Cys
    1070            1075            1080

Glu Cys Pro Ser Gly Trp Thr Gly Leu Tyr Cys Asp Val Pro Ser
    1085            1090            1095

Val Ser Cys Glu Val Ala Ala Gln Arg Gln Gly Val Asp Val Ala
    1100            1105            1110

Arg Leu Cys Gln His Gly Gly Leu Cys Val Asp Ala Gly Asn Thr
    1115            1120            1125

His His Cys Arg Cys Gln Ala Gly Tyr Thr Gly Ser Tyr Cys Glu
    1130            1135            1140

Asp Leu Val Asp Glu Cys Ser Pro Ser Pro Cys Gln Asn Gly Ala
    1145            1150            1155

Thr Cys Thr Asp Tyr Leu Gly Gly Tyr Ser Cys Lys Cys Val Ala
    1160            1165            1170

Gly Tyr His Gly Val Asn Cys Ser Glu Glu Ile Asp Glu Cys Leu
    1175            1180            1185

Ser His Pro Cys Gln Asn Gly Gly Thr Cys Leu Asp Leu Pro Asn
    1190            1195            1200

Thr Tyr Lys Cys Ser Cys Pro Arg Gly Thr Gln Gly Val His Cys
    1205            1210            1215

Glu Ile Asn Val Asp Asp Cys Asn Pro Pro Val Asp Pro Val Ser
    1220            1225            1230

Arg Ser Pro Lys Cys Phe Asn Asn Gly Thr Cys Val Asp Gln Val
    1235            1240            1245

Gly Gly Tyr Ser Cys Thr Cys Pro Pro Gly Phe Val Gly Glu Arg
    1250            1255            1260

Cys Glu Gly Asp Val Asn Glu Cys Leu Ser Asn Pro Cys Asp Ala
    1265            1270            1275

Arg Gly Thr Gln Asn Cys Val Gln Arg Val Asn Asp Phe His Cys
    1280            1285            1290

Glu Cys Arg Ala Gly His Thr Gly Arg Arg Cys Glu Ser Val Ile
    1295            1300            1305

Asn Gly Cys Lys Gly Lys Pro Cys Lys Asn Gly Gly Thr Cys Ala
    1310            1315            1320

Val Ala Ser Asn Thr Ala Arg Gly Phe Ile Cys Lys Cys Pro Ala
    1325            1330            1335

Gly Phe Glu Gly Ala Thr Cys Glu Asn Asp Ala Arg Thr Cys Gly
    1340            1345            1350

Ser Leu Arg Cys Leu Asn Gly Gly Thr Cys Ile Ser Gly Pro Arg
    1355            1360            1365

Ser Pro Thr Cys Leu Cys Leu Gly Pro Phe Thr Gly Pro Glu Cys
    1370            1375            1380

Gln Phe Pro Ala Ser Ser Pro Cys Leu Gly Gly Asn Pro Cys Tyr
    1385            1390            1395
```

```
Asn Gln Gly Thr Cys Glu Pro Thr Ser Glu Ser Pro Phe Tyr Arg
    1400            1405            1410

Cys Leu Cys Pro Ala Lys Phe Asn Gly Leu Leu Cys His Ile Leu
    1415            1420            1425

Asp Tyr Ser Phe Gly Gly Ala Gly Arg Asp Ile Pro Pro Pro
    1430            1435            1440

Leu Ile Glu Glu Ala Cys Glu Leu Pro Glu Cys Gln Glu Asp Ala
    1445            1450            1455

Gly Asn Lys Val Cys Ser Leu Gln Cys Asn Asn His Ala Cys Gly
    1460            1465            1470

Trp Asp Gly Gly Asp Cys Ser Leu Asn Phe Asn Asp Pro Trp Lys
    1475            1480            1485

Asn Cys Thr Gln Ser Leu Gln Cys Trp Lys Tyr Phe Ser Asp Gly
    1490            1495            1500

His Cys Asp Ser Gln Cys Asn Ser Ala Gly Cys Leu Phe Asp Gly
    1505            1510            1515

Phe Asp Cys Gln Arg Ala Glu Gly Gln Cys Asn Pro Leu Tyr Asp
    1520            1525            1530

Gln Tyr Cys Lys Asp His Phe Ser Asp Gly His Cys Asp Gln Gly
    1535            1540            1545

Cys Asn Ser Ala Glu Cys Glu Trp Asp Gly Leu Asp Cys Ala Glu
    1550            1555            1560

His Val Pro Glu Arg Leu Ala Ala Gly Thr Leu Val Val Val Val
    1565            1570            1575

Leu Met Pro Pro Glu Gln Leu Arg Asn Ser Ser Phe His Phe Leu
    1580            1585            1590

Arg Glu Leu Ser Arg Val Leu His Thr Asn Val Val Phe Lys Arg
    1595            1600            1605

Asp Ala His Gly Gln Gln Met Ile Phe Pro Tyr Tyr Gly Arg Glu
    1610            1615            1620

Glu Glu Leu Arg Lys His Pro Ile Lys Arg Ala Ala Glu Gly Trp
    1625            1630            1635

Ala Ala Pro Asp Ala Leu Leu Gly Gln Val Lys Ala Ser Leu Leu
    1640            1645            1650

Pro Gly Gly Ser Glu Gly Gly Arg Arg Arg Arg Glu Leu Asp Pro
    1655            1660            1665

Met Asp Val Arg Gly Ser Ile Val Tyr Leu Glu Ile Asp Asn Arg
    1670            1675            1680

Gln Cys Val Gln Ala Ser Ser Gln Cys Phe Gln Ser Ala Thr Asp
    1685            1690            1695

Val Ala Ala Phe Leu Gly Ala Leu Ala Ser Leu Gly Ser Leu Asn
    1700            1705            1710

Ile Pro Tyr Lys Ile Glu Ala Val Gln Ser Glu Thr Val Glu Pro
    1715            1720            1725

Pro Pro Pro Ala Gln Leu His Phe Met Tyr Val Ala Ala Ala Ala
    1730            1735            1740

Phe Val Leu Leu Phe Phe Val Gly Cys Gly Val Leu Leu Ser Arg
    1745            1750            1755

Lys Arg Arg Arg Gln His Gly Gln Leu Trp Phe Pro Glu Gly Phe
    1760            1765            1770

Lys Val Ser Glu Ala Ser Lys Lys Lys Arg Arg Glu Pro Leu Gly
    1775            1780            1785
```

```
Glu Asp Ser Val Gly Leu Lys Pro Leu Lys Asn Ala Ser Asp Gly
1790                1795                1800

Ala Leu Met Asp Asp Asn Gln Asn Glu Trp Gly Asp Glu Asp Leu
1805                1810                1815

Glu Thr Lys Lys Phe Arg Phe Glu Glu Pro Val Val Leu Pro Asp
1820                1825                1830

Leu Asp Asp Gln Thr Asp His Arg Gln Trp Thr Gln Gln His Leu
1835                1840                1845

Asp Ala Ala Asp Leu Arg Met Ser Ala Met Ala Pro Thr Pro Pro
1850                1855                1860

Gln Gly Glu Val Asp Ala Asp Cys Met Asp Val Asn Val Arg Gly
1865                1870                1875

Pro Asp Gly Phe Thr Pro Leu Met Ile Ala Ser Cys Ser Gly Gly
1880                1885                1890

Gly Leu Glu Thr Gly Asn Ser Glu Glu Glu Glu Asp Ala Pro Ala
1895                1900                1905

Val Ile Ser Asp Phe Ile Tyr Gln Gly Ala Ser Leu His Asn Gln
1910                1915                1920

Thr Asp Arg Thr Gly Glu Thr Ala Leu His Leu Ala Ala Arg Tyr
1925                1930                1935

Ser Arg Ser Asp Ala Ala Lys Arg Leu Leu Glu Ala Ser Ala Asp
1940                1945                1950

Ala Asn Ile Gln Asp Asn Met Gly Arg Thr Pro Leu His Ala Ala
1955                1960                1965

Val Ser Ala Asp Ala Gln Gly Val Phe Gln Ile Leu Ile Arg Asn
1970                1975                1980

Arg Ala Thr Asp Leu Asp Ala Arg Met His Asp Gly Thr Thr Pro
1985                1990                1995

Leu Ile Leu Ala Ala Arg Leu Ala Val Glu Gly Met Leu Glu Asp
2000                2005                2010

Leu Ile Asn Ser His Ala Asp Val Asn Ala Val Asp Asp Leu Gly
2015                2020                2025

Lys Ser Ala Leu His Trp Ala Ala Ala Val Asn Asn Val Asp Ala
2030                2035                2040

Ala Val Val Leu Leu Lys Asn Gly Ala Asn Lys Asp Met Gln Asn
2045                2050                2055

Asn Arg Glu Glu Thr Pro Leu Phe Leu Ala Ala Arg Glu Gly Ser
2060                2065                2070

Tyr Glu Thr Ala Lys Val Leu Leu Asp His Phe Ala Asn Arg Asp
2075                2080                2085

Ile Thr Asp His Met Asp Arg Leu Pro Arg Asp Ile Ala Gln Glu
2090                2095                2100

Arg Met His His Asp Ile Val Arg Leu Leu Asp Glu Tyr Asn Leu
2105                2110                2115

Val Arg Ser Pro Gln Leu His Gly Ala Pro Leu Gly Gly Thr Pro
2120                2125                2130

Thr Leu Ser Pro Pro Leu Cys Ser Pro Asn Gly Tyr Leu Gly Ser
2135                2140                2145

Leu Lys Pro Gly Val Gln Gly Lys Lys Val Arg Lys Pro Ser Ser
2150                2155                2160

Lys Gly Leu Ala Cys Gly Ser Lys Glu Ala Lys Asp Leu Lys Ala
2165                2170                2175

Arg Arg Lys Lys Ser Gln Asp Gly Lys Gly Cys Leu Leu Asp Ser
```

```
                2180               2185               2190

Ser Gly Met Leu Ser Pro Val Asp Ser Leu Glu Ser Pro His Gly
    2195               2200               2205

Tyr Leu Ser Asp Val Ala Ser Pro Pro Leu Leu Pro Ser Pro Phe
    2210               2215               2220

Gln Gln Ser Pro Ser Val Pro Leu Asn His Leu Pro Gly Met Pro
    2225               2230               2235

Asp Thr His Leu Gly Ile Gly His Leu Asn Val Ala Ala Lys Pro
    2240               2245               2250

Glu Met Ala Ala Leu Gly Gly Gly Gly Arg Leu Ala Phe Glu Thr
    2255               2260               2265

Gly Pro Pro Arg Leu Ser His Leu Pro Val Ala Ser Gly Thr Ser
    2270               2275               2280

Thr Val Leu Gly Ser Ser Ser Gly Gly Ala Leu Asn Phe Thr Val
    2285               2290               2295

Gly Gly Ser Thr Ser Leu Asn Gly Gln Cys Glu Trp Leu Ser Arg
    2300               2305               2310

Leu Gln Ser Gly Met Val Pro Asn Gln Tyr Asn Pro Leu Arg Gly
    2315               2320               2325

Ser Val Ala Pro Gly Pro Leu Ser Thr Gln Ala Pro Ser Leu Gln
    2330               2335               2340

His Gly Met Val Gly Pro Leu His Ser Ser Leu Ala Ala Ser Ala
    2345               2350               2355

Leu Ser Gln Met Met Ser Tyr Gln Gly Leu Pro Ser Thr Arg Leu
    2360               2365               2370

Ala Thr Gln Pro His Leu Val Gln Thr Gln Gln Val Gln Pro Gln
    2375               2380               2385

Asn Leu Gln Met Gln Gln Gln Asn Leu Gln Pro Ala Asn Ile Gln
    2390               2395               2400

Gln Gln Gln Ser Leu Gln Pro Pro Pro Pro Pro Gln Pro His
    2405               2410               2415

Leu Gly Val Ser Ser Ala Ala Ser Gly His Leu Gly Arg Ser Phe
    2420               2425               2430

Leu Ser Gly Glu Pro Ser Gln Ala Asp Val Gln Pro Leu Gly Pro
    2435               2440               2445

Ser Ser Leu Ala Val His Thr Ile Leu Pro Gln Glu Ser Pro Ala
    2450               2455               2460

Leu Pro Thr Ser Leu Pro Ser Ser Leu Val Pro Pro Val Thr Ala
    2465               2470               2475

Ala Gln Phe Leu Thr Pro Pro Ser Gln His Ser Tyr Ser Ser Pro
    2480               2485               2490

Val Asp Asn Thr Pro Ser His Gln Leu Gln Val Pro Glu His Pro
    2495               2500               2505

Phe Leu Thr Pro Ser Pro Glu Ser Pro Asp Gln Trp Ser Ser Ser
    2510               2515               2520

Ser Pro His Ser Asn Val Ser Asp Trp Ser Glu Gly Val Ser Ser
    2525               2530               2535

Pro Pro Thr Ser Met Gln Ser Gln Ile Ala Arg Ile Pro Glu Ala
    2540               2545               2550

Phe Lys
    2555

<210> SEQ ID NO 2
```

```
<211> LENGTH: 2471
<212> TYPE: PRT
<213> ORGANISM: Homo sapiens

<400> SEQUENCE: 2
```

| | | | | | | | | | | | | | | |
|---|---|---|---|---|---|---|---|---|---|---|---|---|---|---|
| Met | Pro | Ala | Leu | Arg | Pro | Ala | Leu | Leu | Trp | Ala | Leu | Leu | Ala | Leu | Trp |
| 1 | | | | 5 | | | | | 10 | | | | | 15 | |

| Leu | Cys | Cys | Ala | Ala | Pro | Ala | His | Ala | Leu | Gln | Cys | Arg | Asp | Gly | Tyr |
| | | | 20 | | | | | 25 | | | | | 30 | | |

| Glu | Pro | Cys | Val | Asn | Glu | Gly | Met | Cys | Val | Thr | Tyr | His | Asn | Gly | Thr |
| | | 35 | | | | | 40 | | | | | 45 | | | |

| Gly | Tyr | Cys | Lys | Cys | Pro | Glu | Gly | Phe | Leu | Gly | Glu | Tyr | Cys | Gln | His |
| | 50 | | | | | 55 | | | | | 60 | | | | |

| Arg | Asp | Pro | Cys | Glu | Lys | Asn | Arg | Cys | Gln | Asn | Gly | Gly | Thr | Cys | Val |
| 65 | | | | | 70 | | | | | 75 | | | | | 80 |

| Ala | Gln | Ala | Met | Leu | Gly | Lys | Ala | Thr | Cys | Arg | Cys | Ala | Ser | Gly | Phe |
| | | | | 85 | | | | | 90 | | | | | 95 | |

| Thr | Gly | Glu | Asp | Cys | Gln | Tyr | Ser | Thr | Ser | His | Pro | Cys | Phe | Val | Ser |
| | | | 100 | | | | | 105 | | | | | 110 | | |

| Arg | Pro | Cys | Leu | Asn | Gly | Gly | Thr | Cys | His | Met | Leu | Ser | Arg | Asp | Thr |
| | | 115 | | | | | 120 | | | | | 125 | | | |

| Tyr | Glu | Cys | Thr | Cys | Gln | Val | Gly | Phe | Thr | Gly | Lys | Glu | Cys | Gln | Trp |
| | 130 | | | | | 135 | | | | | 140 | | | | |

| Thr | Asp | Ala | Cys | Leu | Ser | His | Pro | Cys | Ala | Asn | Gly | Ser | Thr | Cys | Thr |
| 145 | | | | | 150 | | | | | 155 | | | | | 160 |

| Thr | Val | Ala | Asn | Gln | Phe | Ser | Cys | Lys | Cys | Leu | Thr | Gly | Phe | Thr | Gly |
| | | | | 165 | | | | | 170 | | | | | 175 | |

| Gln | Lys | Cys | Glu | Thr | Asp | Val | Asn | Glu | Cys | Asp | Ile | Pro | Gly | His | Cys |
| | | 180 | | | | | 185 | | | | | 190 | | | |

| Gln | His | Gly | Gly | Thr | Cys | Leu | Asn | Leu | Pro | Gly | Ser | Tyr | Gln | Cys | Gln |
| | 195 | | | | | 200 | | | | | 205 | | | | |

| Cys | Pro | Gln | Gly | Phe | Thr | Gly | Gln | Tyr | Cys | Asp | Ser | Leu | Tyr | Val | Pro |
| 210 | | | | | 215 | | | | | 220 | | | | | |

| Cys | Ala | Pro | Ser | Pro | Cys | Val | Asn | Gly | Gly | Thr | Cys | Arg | Gln | Thr | Gly |
| 225 | | | | 230 | | | | | 235 | | | | | 240 | |

| Asp | Phe | Thr | Phe | Glu | Cys | Asn | Cys | Leu | Pro | Gly | Phe | Glu | Gly | Ser | Thr |
| | | | | 245 | | | | | 250 | | | | | 255 | |

| Cys | Glu | Arg | Asn | Ile | Asp | Asp | Cys | Pro | Asn | His | Arg | Cys | Gln | Asn | Gly |
| | | | 260 | | | | | 265 | | | | | 270 | | |

| Gly | Val | Cys | Val | Asp | Gly | Val | Asn | Thr | Tyr | Asn | Cys | Arg | Cys | Pro | Pro |
| | | 275 | | | | | 280 | | | | | 285 | | | |

| Gln | Trp | Thr | Gly | Gln | Phe | Cys | Thr | Glu | Asp | Val | Asp | Glu | Cys | Leu | Leu |
| | 290 | | | | | 295 | | | | | 300 | | | | |

| Gln | Pro | Asn | Ala | Cys | Gln | Asn | Gly | Gly | Thr | Cys | Ala | Asn | Arg | Asn | Gly |
| 305 | | | | | 310 | | | | | 315 | | | | | 320 |

| Gly | Tyr | Gly | Cys | Val | Cys | Val | Asn | Gly | Trp | Ser | Gly | Asp | Asp | Cys | Ser |
| | | | | 325 | | | | | 330 | | | | | 335 | |

| Glu | Asn | Ile | Asp | Asp | Cys | Ala | Phe | Ala | Ser | Cys | Thr | Pro | Gly | Ser | Thr |
| | | | 340 | | | | | 345 | | | | | 350 | | |

| Cys | Ile | Asp | Arg | Val | Ala | Ser | Phe | Ser | Cys | Met | Cys | Pro | Glu | Gly | Lys |
| | | 355 | | | | | 360 | | | | | 365 | | | |

| Ala | Gly | Leu | Leu | Cys | His | Leu | Asp | Asp | Ala | Cys | Ile | Ser | Asn | Pro | Cys |
| | 370 | | | | | 375 | | | | | 380 | | | | |

| His | Lys | Gly | Ala | Leu | Cys | Asp | Thr | Asn | Pro | Leu | Asn | Gly | Gln | Tyr | Ile |

```
            385                 390                 395                 400
        Cys Thr Cys Pro Gln Gly Tyr Lys Gly Ala Asp Cys Thr Glu Asp Val
                        405                 410                 415
        Asp Glu Cys Ala Met Ala Asn Ser Asn Pro Cys Glu His Ala Gly Lys
                        420                 425                 430
        Cys Val Asn Thr Asp Gly Ala Phe His Cys Glu Cys Leu Lys Gly Tyr
                        435                 440                 445
        Ala Gly Pro Arg Cys Glu Met Asp Ile Asn Gly Cys His Ser Asp Pro
                        450                 455                 460
        Cys Gln Asn Asp Ala Thr Cys Leu Asp Lys Ile Gly Gly Phe Thr Cys
        465                 470                 475                 480
        Leu Cys Met Pro Gly Phe Lys Gly Val His Cys Glu Leu Glu Ile Asn
                        485                 490                 495
        Glu Cys Gln Ser Asn Pro Cys Val Asn Asn Gly Gln Cys Val Asp Lys
                        500                 505                 510
        Val Asn Arg Phe Gln Cys Leu Cys Pro Pro Gly Phe Thr Gly Pro Val
                        515                 520                 525
        Cys Gln Ile Asp Ile Asp Asp Cys Ser Ser Thr Pro Cys Leu Asn Gly
                        530                 535                 540
        Ala Lys Cys Ile Asp His Pro Asn Gly Tyr Glu Cys Gln Cys Ala Thr
        545                 550                 555                 560
        Gly Phe Thr Gly Val Leu Cys Glu Glu Asn Ile Asp Asn Cys Asp Pro
                        565                 570                 575
        Asp Pro Cys His His Gly Gln Cys Gln Asp Gly Ile Asp Ser Tyr Thr
                        580                 585                 590
        Cys Ile Cys Asn Pro Gly Tyr Met Gly Ala Ile Cys Ser Asp Gln Ile
                        595                 600                 605
        Asp Glu Cys Tyr Ser Ser Pro Cys Leu Asn Asp Gly Arg Cys Ile Asp
                        610                 615                 620
        Leu Val Asn Gly Tyr Gln Cys Asn Cys Gln Pro Gly Thr Ser Gly Val
        625                 630                 635                 640
        Asn Cys Glu Ile Asn Phe Asp Asp Cys Ala Ser Asn Pro Cys Ile His
                        645                 650                 655
        Gly Ile Cys Met Asp Gly Ile Asn Arg Tyr Ser Cys Val Cys Ser Pro
                        660                 665                 670
        Gly Phe Thr Gly Gln Arg Cys Asn Ile Asp Ile Asp Glu Cys Ala Ser
                        675                 680                 685
        Asn Pro Cys Arg Lys Gly Ala Thr Cys Ile Asn Gly Val Asn Gly Phe
                        690                 695                 700
        Arg Cys Ile Cys Pro Glu Gly His His Pro Ser Cys Tyr Ser Gln
        705                 710                 715                 720
        Val Asn Glu Cys Leu Ser Asn Pro Cys Ile His Gly Asn Cys Thr Gly
                        725                 730                 735
        Gly Leu Ser Gly Tyr Lys Cys Leu Cys Asp Ala Gly Trp Val Gly Ile
                        740                 745                 750
        Asn Cys Glu Val Asp Lys Asn Glu Cys Leu Ser Asn Pro Cys Gln Asn
                        755                 760                 765
        Gly Gly Thr Cys Asp Asn Leu Val Asn Gly Tyr Arg Cys Thr Cys Lys
                        770                 775                 780
        Lys Gly Phe Lys Gly Tyr Asn Cys Gln Val Asn Ile Asp Glu Cys Ala
        785                 790                 795                 800
        Ser Asn Pro Cys Leu Asn Gln Gly Thr Cys Phe Asp Asp Ile Ser Gly
                        805                 810                 815
```

-continued

```
Tyr Thr Cys His Cys Val Leu Pro Tyr Thr Gly Lys Asn Cys Gln Thr
            820                 825                 830

Val Leu Ala Pro Cys Ser Pro Asn Pro Cys Glu Asn Ala Ala Val Cys
            835                 840                 845

Lys Glu Ser Pro Asn Phe Glu Ser Tyr Thr Cys Leu Cys Ala Pro Gly
850                 855                 860

Trp Gln Gly Gln Arg Cys Thr Ile Asp Ile Asp Glu Cys Ile Ser Lys
865                 870                 875                 880

Pro Cys Met Asn His Gly Leu Cys His Asn Thr Gln Gly Ser Tyr Met
                885                 890                 895

Cys Glu Cys Pro Pro Gly Phe Ser Gly Met Asp Cys Glu Glu Asp Ile
            900                 905                 910

Asp Asp Cys Leu Ala Asn Pro Cys Gln Asn Gly Gly Ser Cys Met Asp
            915                 920                 925

Gly Val Asn Thr Phe Ser Cys Leu Cys Leu Pro Gly Phe Thr Gly Asp
            930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
                965                 970                 975

Ala Gly Phe Asp Gly Val His Cys Glu Asn Asn Ile Asn Glu Cys Thr
            980                 985                 990

Glu Ser Ser Cys Phe Asn Gly Gly Thr Cys Val Asp Gly Ile Asn Ser
            995                 1000                1005

Phe Ser Cys Leu Cys Pro Val Gly Phe Thr Gly Ser Phe Cys Leu
    1010                1015                1020

His Glu Ile Asn Glu Cys Ser Ser His Pro Cys Leu Asn Glu Gly
    1025                1030                1035

Thr Cys Val Asp Gly Leu Gly Thr Tyr Arg Cys Ser Cys Pro Leu
    1040                1045                1050

Gly Tyr Thr Gly Lys Asn Cys Gln Thr Leu Val Asn Leu Cys Ser
    1055                1060                1065

Arg Ser Pro Cys Lys Asn Lys Gly Thr Cys Val Gln Lys Lys Ala
    1070                1075                1080

Glu Ser Gln Cys Leu Cys Pro Ser Gly Trp Ala Gly Ala Tyr Cys
    1085                1090                1095

Asp Val Pro Asn Val Ser Cys Asp Ile Ala Ala Ser Arg Arg Gly
    1100                1105                1110

Val Leu Val Glu His Leu Cys Gln His Ser Gly Val Cys Ile Asn
    1115                1120                1125

Ala Gly Asn Thr His Tyr Cys Gln Cys Pro Leu Gly Tyr Thr Gly
    1130                1135                1140

Ser Tyr Cys Glu Glu Gln Leu Asp Glu Cys Ala Ser Asn Pro Cys
    1145                1150                1155

Gln His Gly Ala Thr Cys Ser Asp Phe Ile Gly Gly Tyr Arg Cys
    1160                1165                1170

Glu Cys Val Pro Gly Tyr Gln Gly Val Asn Cys Glu Tyr Glu Val
    1175                1180                1185

Asp Glu Cys Gln Asn Gln Pro Cys Gln Asn Gly Gly Thr Cys Ile
    1190                1195                1200

Asp Leu Val Asn His Phe Lys Cys Ser Cys Pro Pro Gly Thr Arg
    1205                1210                1215
```

-continued

Gly Leu Leu Cys Glu Glu Asn Ile Asp Asp Cys Ala Arg Gly Pro
    1220                1225                1230

His Cys Leu Asn Gly Gly Gln Cys Met Asp Arg Ile Gly Gly Tyr
    1235                1240                1245

Ser Cys Arg Cys Leu Pro Gly Phe Ala Gly Glu Arg Cys Glu Gly
    1250                1255                1260

Asp Ile Asn Glu Cys Leu Ser Asn Pro Cys Ser Ser Glu Gly Ser
    1265                1270                1275

Leu Asp Cys Ile Gln Leu Thr Asn Asp Tyr Leu Cys Val Cys Arg
    1280                1285                1290

Ser Ala Phe Thr Gly Arg His Cys Glu Thr Phe Val Asp Val Cys
    1295                1300                1305

Pro Gln Met Pro Cys Leu Asn Gly Gly Thr Cys Ala Val Ala Ser
    1310                1315                1320

Asn Met Pro Asp Gly Phe Ile Cys Arg Cys Pro Pro Gly Phe Ser
    1325                1330                1335

Gly Ala Arg Cys Gln Ser Ser Cys Gly Gln Val Lys Cys Arg Lys
    1340                1345                1350

Gly Glu Gln Cys Val His Thr Ala Ser Gly Pro Arg Cys Phe Cys
    1355                1360                1365

Pro Ser Pro Arg Asp Cys Glu Ser Gly Cys Ala Ser Ser Pro Cys
    1370                1375                1380

Gln His Gly Gly Ser Cys His Pro Gln Arg Gln Pro Pro Tyr Tyr
    1385                1390                1395

Ser Cys Gln Cys Ala Pro Pro Phe Ser Gly Ser Arg Cys Glu Leu
    1400                1405                1410

Tyr Thr Ala Pro Pro Ser Thr Pro Pro Ala Thr Cys Leu Ser Gln
    1415                1420                1425

Tyr Cys Ala Asp Lys Ala Arg Asp Gly Val Cys Asp Glu Ala Cys
    1430                1435                1440

Asn Ser His Ala Cys Gln Trp Asp Gly Gly Asp Cys Ser Leu Thr
    1445                1450                1455

Met Glu Asn Pro Trp Ala Asn Cys Ser Ser Pro Leu Pro Cys Trp
    1460                1465                1470

Asp Tyr Ile Asn Asn Gln Cys Asp Glu Leu Cys Asn Thr Val Glu
    1475                1480                1485

Cys Leu Phe Asp Asn Phe Glu Cys Gln Gly Asn Ser Lys Thr Cys
    1490                1495                1500

Lys Tyr Asp Lys Tyr Cys Ala Asp His Phe Lys Asp Asn His Cys
    1505                1510                1515

Asp Gln Gly Cys Asn Ser Glu Glu Cys Gly Trp Asp Gly Leu Asp
    1520                1525                1530

Cys Ala Ala Asp Gln Pro Glu Asn Leu Ala Glu Gly Thr Leu Val
    1535                1540                1545

Ile Val Val Leu Met Pro Pro Glu Gln Leu Leu Gln Asp Ala Arg
    1550                1555                1560

Ser Phe Leu Arg Ala Leu Gly Thr Leu Leu His Thr Asn Leu Arg
    1565                1570                1575

Ile Lys Arg Asp Ser Gln Gly Glu Leu Met Val Tyr Pro Tyr Tyr
    1580                1585                1590

Gly Glu Lys Ser Ala Ala Met Lys Lys Gln Arg Met Thr Arg Arg
    1595                1600                1605

Ser Leu Pro Gly Glu Gln Glu Gln Glu Val Ala Gly Ser Lys Val

```
            1610                1615                1620

Phe Leu Glu Ile Asp Asn Arg Gln Cys Val Gln Asp Ser Asp His
    1625                1630                1635

Cys Phe Lys Asn Thr Asp Ala Ala Ala Leu Leu Ala Ser His
    1640                1645                1650

Ala Ile Gln Gly Thr Leu Ser Tyr Pro Leu Val Ser Val Val Ser
    1655                1660                1665

Glu Ser Leu Thr Pro Glu Arg Thr Gln Leu Leu Tyr Leu Leu Ala
    1670                1675                1680

Val Ala Val Val Ile Ile Leu Phe Ile Ile Leu Leu Gly Val Ile
    1685                1690                1695

Met Ala Lys Arg Lys Arg Lys His Gly Ser Leu Trp Leu Pro Glu
    1700                1705                1710

Gly Phe Thr Leu Arg Arg Asp Ala Ser Asn His Lys Arg Arg Glu
    1715                1720                1725

Pro Val Gly Gln Asp Ala Val Gly Leu Lys Asn Leu Ser Val Gln
    1730                1735                1740

Val Ser Glu Ala Asn Leu Ile Gly Thr Gly Thr Ser Glu His Trp
    1745                1750                1755

Val Asp Asp Glu Gly Pro Gln Pro Lys Lys Val Lys Ala Glu Asp
    1760                1765                1770

Glu Ala Leu Leu Ser Glu Glu Asp Asp Pro Ile Asp Arg Arg Pro
    1775                1780                1785

Trp Thr Gln Gln His Leu Glu Ala Ala Asp Ile Arg Arg Thr Pro
    1790                1795                1800

Ser Leu Ala Leu Thr Pro Pro Gln Ala Glu Gln Glu Val Asp Val
    1805                1810                1815

Leu Asp Val Asn Val Arg Gly Pro Asp Gly Cys Thr Pro Leu Met
    1820                1825                1830

Leu Ala Ser Leu Arg Gly Gly Ser Ser Asp Leu Ser Asp Glu Asp
    1835                1840                1845

Glu Asp Ala Glu Asp Ser Ser Ala Asn Ile Ile Thr Asp Leu Val
    1850                1855                1860

Tyr Gln Gly Ala Ser Leu Gln Ala Gln Thr Asp Arg Thr Gly Glu
    1865                1870                1875

Met Ala Leu His Leu Ala Ala Arg Tyr Ser Arg Ala Asp Ala Ala
    1880                1885                1890

Lys Arg Leu Leu Asp Ala Gly Ala Asp Ala Asn Ala Gln Asp Asn
    1895                1900                1905

Met Gly Arg Cys Pro Leu His Ala Ala Val Ala Ala Asp Ala Gln
    1910                1915                1920

Gly Val Phe Gln Ile Leu Ile Arg Asn Arg Val Thr Asp Leu Asp
    1925                1930                1935

Ala Arg Met Asn Asp Gly Thr Thr Pro Leu Ile Leu Ala Ala Arg
    1940                1945                1950

Leu Ala Val Glu Gly Met Val Ala Glu Leu Ile Asn Cys Gln Ala
    1955                1960                1965

Asp Val Asn Ala Val Asp Asp His Gly Lys Ser Ala Leu His Trp
    1970                1975                1980

Ala Ala Ala Val Asn Asn Val Glu Ala Thr Leu Leu Leu Leu Lys
    1985                1990                1995

Asn Gly Ala Asn Arg Asp Met Gln Asp Asn Lys Glu Glu Thr Pro
    2000                2005                2010
```

```
Leu Phe Leu Ala Ala Arg Glu Gly Ser Tyr Glu Ala Ala Lys Ile
    2015                2020                2025

Leu Leu Asp His Phe Ala Asn Arg Asp Ile Thr Asp His Met Asp
    2030                2035                2040

Arg Leu Pro Arg Asp Val Ala Arg Asp Arg Met His His Asp Ile
    2045                2050                2055

Val Arg Leu Leu Asp Glu Tyr Asn Val Thr Pro Ser Pro Pro Gly
    2060                2065                2070

Thr Val Leu Thr Ser Ala Leu Ser Pro Val Ile Cys Gly Pro Asn
    2075                2080                2085

Arg Ser Phe Leu Ser Leu Lys His Thr Pro Met Gly Lys Lys Ser
    2090                2095                2100

Arg Arg Pro Ser Ala Lys Ser Thr Met Pro Thr Ser Leu Pro Asn
    2105                2110                2115

Leu Ala Lys Glu Ala Lys Asp Ala Lys Gly Ser Arg Arg Lys Lys
    2120                2125                2130

Ser Leu Ser Glu Lys Val Gln Leu Ser Glu Ser Ser Val Thr Leu
    2135                2140                2145

Ser Pro Val Asp Ser Leu Glu Ser Pro His Thr Tyr Val Ser Asp
    2150                2155                2160

Thr Thr Ser Ser Pro Met Ile Thr Ser Pro Gly Ile Leu Gln Ala
    2165                2170                2175

Ser Pro Asn Pro Met Leu Ala Thr Ala Ala Pro Pro Ala Pro Val
    2180                2185                2190

His Ala Gln His Ala Leu Ser Phe Ser Asn Leu His Glu Met Gln
    2195                2200                2205

Pro Leu Ala His Gly Ala Ser Thr Val Leu Pro Ser Val Ser Gln
    2210                2215                2220

Leu Leu Ser His His His Ile Val Ser Pro Gly Ser Gly Ser Ala
    2225                2230                2235

Gly Ser Leu Ser Arg Leu His Pro Val Pro Val Pro Ala Asp Trp
    2240                2245                2250

Met Asn Arg Met Glu Val Asn Glu Thr Gln Tyr Asn Glu Met Phe
    2255                2260                2265

Gly Met Val Leu Ala Pro Ala Glu Gly Thr His Pro Gly Ile Ala
    2270                2275                2280

Pro Gln Ser Arg Pro Pro Glu Gly Lys His Ile Thr Thr Pro Arg
    2285                2290                2295

Glu Pro Leu Pro Pro Ile Val Thr Phe Gln Leu Ile Pro Lys Gly
    2300                2305                2310

Ser Ile Ala Gln Pro Ala Gly Ala Pro Gln Pro Gln Ser Thr Cys
    2315                2320                2325

Pro Pro Ala Val Ala Gly Pro Leu Pro Thr Met Tyr Gln Ile Pro
    2330                2335                2340

Glu Met Ala Arg Leu Pro Ser Val Ala Phe Pro Thr Ala Met Met
    2345                2350                2355

Pro Gln Gln Asp Gly Gln Val Ala Gln Thr Ile Leu Pro Ala Tyr
    2360                2365                2370

His Pro Phe Pro Ala Ser Val Gly Lys Tyr Pro Thr Pro Pro Ser
    2375                2380                2385

Gln His Ser Tyr Ala Ser Ser Asn Ala Ala Glu Arg Thr Pro Ser
    2390                2395                2400
```

His Ser Gly His Leu Gln Gly Glu His Pro Tyr Leu Thr Pro Ser
    2405                2410                2415

Pro Glu Ser Pro Asp Gln Trp Ser Ser Ser Pro His Ser Ala
    2420                2425                2430

Ser Asp Trp Ser Asp Val Thr Thr Ser Pro Thr Pro Gly Gly Ala
    2435                2440                2445

Gly Gly Gly Gln Arg Gly Pro Gly Thr His Met Ser Glu Pro Pro
    2450                2455                2460

His Asn Asn Met Gln Val Tyr Ala
    2465                2470

<210> SEQ ID NO 3
<211> LENGTH: 723
<212> TYPE: PRT
<213> ORGANISM: Homo sapiens

<400> SEQUENCE: 3

Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ala Gly Pro Pro Pro Cys Ala Cys Arg Thr Phe Phe Arg Val Cys Leu
    50                  55                  60

Lys His Tyr Gln Ala Ser Val Ser Pro Glu Pro Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
    130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
        275                 280                 285

Leu Asn Tyr Cys Thr His His Lys Pro Cys Lys Asn Gly Ala Thr Cys
    290                 295                 300

```
Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
            325                 330                 335

Cys Lys Asn Gly Gly Ser Cys Thr Asp Leu Glu Asn Ser Tyr Ser Cys
            340                 345                 350

Thr Cys Pro Pro Gly Phe Tyr Gly Lys Ile Cys Glu Leu Ser Ala Met
            355                 360                 365

Thr Cys Ala Asp Gly Pro Cys Phe Asn Gly Gly Arg Cys Ser Asp Ser
            370                 375                 380

Pro Asp Gly Gly Tyr Ser Cys Arg Cys Pro Val Gly Tyr Ser Gly Phe
385                 390                 395                 400

Asn Cys Glu Lys Lys Ile Asp Tyr Cys Ser Ser Ser Pro Cys Ser Asn
            405                 410                 415

Gly Ala Lys Cys Val Asp Leu Gly Asp Ala Tyr Leu Cys Arg Cys Gln
            420                 425                 430

Ala Gly Phe Ser Gly Arg His Cys Asp Asp Asn Val Asp Asp Cys Ala
            435                 440                 445

Ser Ser Pro Cys Ala Asn Gly Gly Thr Cys Arg Asp Gly Val Asn Asp
450                 455                 460

Phe Ser Cys Thr Cys Pro Pro Gly Tyr Thr Gly Arg Asn Cys Ser Ala
465                 470                 475                 480

Pro Val Ser Arg Cys Glu His Ala Pro Cys His Asn Gly Ala Thr Cys
            485                 490                 495

His Glu Arg Gly His Arg Tyr Val Cys Glu Cys Ala Arg Gly Tyr Gly
            500                 505                 510

Gly Pro Asn Cys Gln Phe Leu Leu Pro Glu Leu Pro Pro Gly Pro Ala
            515                 520                 525

Val Val Asp Leu Thr Glu Lys Leu Glu Gly Gln Gly Gly Pro Phe Pro
            530                 535                 540

Trp Val Ala Val Cys Ala Gly Val Ile Leu Val Leu Met Leu Leu Leu
545                 550                 555                 560

Gly Cys Ala Ala Val Val Val Cys Val Arg Leu Arg Leu Gln Lys His
            565                 570                 575

Arg Pro Pro Ala Asp Pro Cys Arg Gly Glu Thr Glu Thr Met Asn Asn
            580                 585                 590

Leu Ala Asn Cys Gln Arg Glu Lys Asp Ile Ser Val Ser Ile Ile Gly
            595                 600                 605

Ala Thr Gln Ile Lys Asn Thr Asn Lys Lys Ala Asp Phe His Gly Asp
            610                 615                 620

His Ser Ala Asp Lys Asn Gly Phe Lys Ala Arg Tyr Pro Ala Val Asp
625                 630                 635                 640

Tyr Asn Leu Val Gln Asp Leu Lys Gly Asp Asp Thr Ala Val Arg Asp
            645                 650                 655

Ala His Ser Lys Arg Asp Thr Lys Cys Gln Pro Gln Gly Ser Ser Gly
            660                 665                 670

Glu Glu Lys Gly Thr Pro Thr Thr Leu Arg Gly Gly Glu Ala Ser Glu
            675                 680                 685

Arg Lys Arg Pro Asp Ser Gly Cys Ser Thr Ser Lys Asp Thr Lys Tyr
            690                 695                 700

Gln Ser Val Tyr Val Ile Ser Glu Glu Lys Asp Glu Cys Val Ile Ala
705                 710                 715                 720
```

-continued

Thr Glu Val

<210> SEQ ID NO 4
<211> LENGTH: 618
<212> TYPE: PRT
<213> ORGANISM: Homo sapiens

<400> SEQUENCE: 4

Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
            20                  25                  30

Gln Ile His Ser Phe Gly Pro Gly Pro Gly Ala Pro Arg Ser
        35                  40                  45

Pro Cys Ser Ala Arg Leu Pro Cys Arg Leu Phe Phe Arg Val Cys Leu
    50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
        115                 120                 125

Glu Glu Leu Gly Asp Gln Ile Gly Gly Pro Ala Trp Ser Leu Leu Ala
    130                 135                 140

Arg Val Ala Gly Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
        195                 200                 205

Pro Leu Glu Asp Glu Cys Glu Ala Pro Leu Val Cys Arg Ala Gly Cys
    210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
                245                 250                 255

Cys Leu Ser Pro Arg Gly Pro Ser Ser Ala Thr Thr Gly Cys Leu Val
            260                 265                 270

Pro Gly Pro Gly Pro Cys Asp Gly Asn Pro Cys Ala Asn Gly Gly Ser
        275                 280                 285

Cys Ser Glu Thr Pro Arg Ser Phe Glu Cys Thr Cys Pro Arg Gly Phe
    290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Gly Ala Asp Pro Asp Ser Ala
                325                 330                 335

Tyr Ile Cys His Cys Pro Pro Gly Phe Gln Gly Ser Asn Cys Glu Lys
            340                 345                 350

Arg Val Asp Arg Cys Ser Leu Gln Pro Cys Arg Asn Gly Gly Leu Cys
        355                 360                 365

```
Leu Asp Leu Gly His Ala Leu Arg Cys Arg Cys Arg Ala Gly Phe Ala
    370                 375                 380

Gly Pro Arg Cys Glu His Asp Leu Asp Asp Cys Ala Gly Arg Ala Cys
385                 390                 395                 400

Ala Asn Gly Gly Thr Cys Val Glu Gly Gly Ala His Arg Cys Ser
                405                 410                 415

Cys Ala Leu Gly Phe Gly Gly Arg Asp Cys Arg Glu Arg Ala Asp Pro
                420                 425                 430

Cys Ala Ala Arg Pro Cys Ala His Gly Gly Arg Cys Tyr Ala His Phe
                435                 440                 445

Ser Gly Leu Val Cys Ala Cys Ala Pro Gly Tyr Met Gly Ala Arg Cys
    450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Pro Pro Ala
                485                 490                 495

Leu Gly Leu Leu Val Ala Ala Gly Val Ala Gly Ala Ala Leu Leu Leu
                500                 505                 510

Val His Val Arg Arg Arg Gly His Ser Gln Asp Ala Gly Ser Arg Leu
                515                 520                 525

Leu Ala Gly Thr Pro Glu Pro Ser Val His Ala Leu Pro Asp Ala Leu
    530                 535                 540

Asn Asn Leu Arg Thr Gln Glu Gly Ser Gly Asp Gly Pro Ser Ser Ser
545                 550                 555                 560

Val Asp Trp Asn Arg Pro Glu Asp Val Asp Pro Gln Gly Ile Tyr Val
                565                 570                 575

Ile Ser Ala Pro Ser Ile Tyr Ala Arg Glu Val Ala Thr Pro Leu Phe
                580                 585                 590

Pro Pro Leu His Thr Gly Arg Ala Gly Gln Arg Gln His Leu Leu Phe
                595                 600                 605

Pro Tyr Pro Ser Ser Ile Leu Ser Val Lys
    610                 615

<210> SEQ ID NO 5
<211> LENGTH: 685
<212> TYPE: PRT
<213> ORGANISM: Homo sapiens

<400> SEQUENCE: 5

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
                20                  25                  30

Gln Leu Gln Glu Phe Ile Asn Glu Arg Gly Val Leu Ala Ser Gly Arg
            35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
                100                 105                 110

Gly Thr Phe Ser Leu Ile Ile Glu Ala Trp His Ala Pro Gly Asp Asp
            115                 120                 125
```

-continued

```
Leu Arg Pro Glu Ala Leu Pro Pro Asp Ala Leu Ile Ser Lys Ile Ala
            130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
                180                 185                 190

Asp His Phe Gly His Tyr Val Cys Gln Pro Asp Gly Asn Leu Ser Cys
            195                 200                 205

Leu Pro Gly Trp Thr Gly Glu Tyr Cys Gln Gln Pro Ile Cys Leu Ser
210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
                260                 265                 270

Asp Glu Gly Trp Gly Gly Leu Phe Cys Asp Gln Asp Leu Asn Tyr Cys
            275                 280                 285

Thr His His Ser Pro Cys Lys Asn Gly Ala Thr Cys Ser Asn Ser Gly
290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
                340                 345                 350

Gly Tyr Tyr Gly Leu His Cys Glu His Ser Thr Leu Ser Cys Ala Asp
            355                 360                 365

Ser Pro Cys Phe Asn Gly Gly Ser Cys Arg Glu Arg Asn Gln Gly Ala
370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
                420                 425                 430

Thr Gly Thr Tyr Cys Glu Leu His Val Ser Asp Cys Ala Arg Asn Pro
            435                 440                 445

Cys Ala His Gly Gly Thr Cys His Asp Leu Glu Asn Gly Leu Met Cys
450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
                500                 505                 510

Val Gly Ser Arg Cys Glu Phe Pro Val Gly Leu Pro Pro Ser Phe Pro
            515                 520                 525

Trp Val Ala Val Ser Leu Gly Val Gly Leu Ala Val Leu Leu Val Leu
530                 535                 540
```

-continued

```
Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
            565                 570                 575

Asp Asn Leu Ile Pro Ala Ala Gln Leu Lys Asn Thr Asn Gln Lys Lys
        580                 585                 590

Glu Leu Glu Val Asp Cys Gly Leu Asp Lys Ser Asn Cys Gly Lys Gln
    595                 600                 605

Gln Asn His Thr Leu Asp Tyr Asn Leu Ala Pro Gly Pro Leu Gly Arg
610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
            645                 650                 655

Ala Ile Cys Ser Pro Arg Asp Ser Met Tyr Gln Ser Val Cys Leu Ile
        660                 665                 670

Ser Glu Glu Arg Asn Glu Cys Val Ile Ala Thr Glu Val
    675                 680                 685

<210> SEQ ID NO 6
<211> LENGTH: 1218
<212> TYPE: PRT
<213> ORGANISM: Homo sapiens

<400> SEQUENCE: 6

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240
```

-continued

```
Lys His Gly Ser Cys Lys Leu Pro Gly Asp Cys Arg Cys Gln Tyr Gly
            245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
            275                 280                 285

Gly Gly Gln Leu Cys Asp Lys Asp Leu Asn Tyr Cys Gly Thr His Gln
            290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
                340                 345                 350

Glu Thr Ser Leu Gly Phe Glu Cys Glu Cys Ser Pro Gly Trp Thr Gly
                355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
                420                 425                 430

Ser Tyr Tyr Cys Asp Cys Leu Pro Gly Trp Met Gly Gln Asn Cys Asp
                435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
                500                 505                 510

Cys Pro Thr Gly Phe Ser Gly Asn Leu Cys Gln Leu Asp Ile Asp Tyr
                515                 520                 525

Cys Glu Pro Asn Pro Cys Gln Asn Gly Ala Gln Cys Tyr Asn Arg Ala
                530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
                580                 585                 590

Tyr Ile Ser Ser Asn Val Cys Gly Pro His Gly Lys Cys Lys Ser Gln
                595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655
```

-continued

Asp Gly Trp Glu Gly Ala Tyr Cys Glu Thr Asn Ile Asn Asp Cys Ser
                660                 665                 670

Gln Asn Pro Cys His Asn Gly Gly Thr Cys Arg Asp Leu Val Asn Asp
            675                 680                 685

Phe Tyr Cys Asp Cys Lys Asn Gly Trp Lys Gly Lys Thr Cys His Ser
        690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
        755                 760                 765

Val Cys Lys Glu Gly Trp Glu Gly Pro Ile Cys Ala Gln Asn Thr Asn
770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
        835                 840                 845

Gly His Ser Gly Ala Lys Cys Gln Glu Val Ser Gly Arg Pro Cys Ile
        850                 855                 860

Thr Met Gly Ser Val Ile Pro Asp Gly Ala Lys Trp Asp Asp Cys
865                 870                 875                 880

Asn Thr Cys Gln Cys Leu Asn Gly Arg Ile Ala Cys Ser Lys Val Trp
            885                 890                 895

Cys Gly Pro Arg Pro Cys Leu Leu His Lys Gly His Ser Glu Cys Pro
        900                 905                 910

Ser Gly Gln Ser Cys Ile Pro Ile Leu Asp Asp Gln Cys Phe Val His
        915                 920                 925

Pro Cys Thr Gly Val Gly Glu Cys Arg Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser Pro Ser Ala
        995                 1000                1005

Asn Asn Glu Ile His Val Ala Ile Ser Ala Glu Asp Ile Arg Asp
        1010                1015                1020

Asp Gly Asn Pro Ile Lys Glu Ile Thr Asp Lys Ile Ile Asp Leu
        1025                1030                1035

Val Ser Lys Arg Asp Gly Asn Ser Ser Leu Ile Ala Ala Val Ala
        1040                1045                1050

Glu Val Arg Val Gln Arg Arg Pro Leu Lys Asn Arg Thr Asp Phe
        1055                1060                1065

Leu Val Pro Leu Leu Ser Ser Val Leu Thr Val Ala Trp Ile Cys

```
                    1070                1075                1080
Cys Leu Val Thr Ala Phe Tyr Trp Cys Leu Arg Lys Arg Arg Lys
        1085                1090                1095

Pro Gly Ser His Thr His Ser Ala Ser Glu Asp Asn Thr Thr Asn
            1100                1105                1110

Asn Val Arg Glu Gln Leu Asn Gln Ile Lys Asn Pro Ile Glu Lys
        1115                1120                1125

His Gly Ala Asn Thr Val Pro Ile Lys Asp Tyr Glu Asn Lys Asn
        1130                1135                1140

Ser Lys Met Ser Lys Ile Arg Thr His Asn Ser Glu Val Glu Glu
        1145                1150                1155

Asp Asp Met Asp Lys His Gln Gln Lys Ala Arg Phe Ala Lys Gln
        1160                1165                1170

Pro Ala Tyr Thr Leu Val Asp Arg Glu Glu Lys Pro Pro Asn Gly
        1175                1180                1185

Thr Pro Thr Lys His Pro Asn Trp Thr Asn Lys Gln Asp Asn Arg
        1190                1195                1200

Asp Leu Glu Ser Ala Gln Ser Leu Asn Arg Met Glu Tyr Ile Val
        1205                1210                1215

<210> SEQ ID NO 7
<211> LENGTH: 1238
<212> TYPE: PRT
<213> ORGANISM: Homo sapiens

<400> SEQUENCE: 7

Met Arg Ala Gln Gly Arg Gly Arg Leu Pro Arg Leu Leu Leu Leu
1               5                   10                  15

Leu Ala Leu Trp Val Gln Ala Ala Arg Pro Met Gly Tyr Phe Glu Leu
            20                  25                  30

Gln Leu Ser Ala Leu Arg Asn Val Asn Gly Glu Leu Leu Ser Gly Ala
        35                  40                  45

Cys Cys Asp Gly Asp Gly Arg Thr Thr Arg Ala Gly Gly Cys Gly His
    50                  55                  60

Asp Glu Cys Asp Thr Tyr Val Arg Val Cys Leu Lys Glu Tyr Gln Ala
65                  70                  75                  80

Lys Val Thr Pro Thr Gly Pro Cys Ser Tyr Gly His Gly Ala Thr Pro
                85                  90                  95

Val Leu Gly Gly Asn Ser Phe Tyr Leu Pro Pro Ala Gly Ala Ala Gly
            100                 105                 110

Asp Arg Ala Arg Ala Arg Ala Gly Gly Asp Gln Asp Pro Gly
        115                 120                 125

Leu Val Val Ile Pro Phe Gln Phe Ala Trp Pro Arg Ser Phe Thr Leu
    130                 135                 140

Ile Val Glu Ala Trp Asp Trp Asp Asn Asp Thr Thr Pro Asn Glu Glu
145                 150                 155                 160

Leu Leu Ile Glu Arg Val Ser His Ala Gly Met Ile Asn Pro Glu Asp
                165                 170                 175

Arg Trp Lys Ser Leu His Phe Ser Gly His Val Ala His Leu Glu Leu
            180                 185                 190

Gln Ile Arg Val Arg Cys Asp Glu Asn Tyr Tyr Ser Ala Thr Cys Asn
        195                 200                 205

Lys Phe Cys Arg Pro Arg Asn Asp Phe Phe Gly His Tyr Thr Cys Asp
    210                 215                 220
```

```
Gln Tyr Gly Asn Lys Ala Cys Met Asp Gly Trp Met Gly Lys Glu Cys
225                 230                 235                 240

Lys Glu Ala Val Cys Lys Gln Gly Cys Asn Leu Leu His Gly Gly Cys
            245                 250                 255

Thr Val Pro Gly Glu Cys Arg Cys Ser Tyr Gly Trp Gln Gly Arg Phe
        260                 265                 270

Cys Asp Glu Cys Val Pro Tyr Pro Gly Cys Val His Gly Ser Cys Val
    275                 280                 285

Glu Pro Trp Gln Cys Asn Cys Glu Thr Asn Trp Gly Gly Leu Leu Cys
290                 295                 300

Asp Lys Asp Leu Asn Tyr Cys Gly Ser His His Pro Cys Thr Asn Gly
305                 310                 315                 320

Gly Thr Cys Ile Asn Ala Glu Pro Asp Gln Tyr Arg Cys Thr Cys Pro
            325                 330                 335

Asp Gly Tyr Ser Gly Arg Asn Cys Glu Lys Ala Glu His Ala Cys Thr
        340                 345                 350

Ser Asn Pro Cys Ala Asn Gly Gly Ser Cys His Glu Val Pro Ser Gly
    355                 360                 365

Phe Glu Cys His Cys Pro Ser Gly Trp Ser Gly Pro Thr Cys Ala Leu
370                 375                 380

Asp Ile Asp Glu Cys Ala Ser Asn Pro Cys Ala Ala Gly Gly Thr Cys
385                 390                 395                 400

Val Asp Gln Val Asp Gly Phe Glu Cys Ile Cys Pro Glu Gln Trp Val
            405                 410                 415

Gly Ala Thr Cys Gln Leu Asp Ala Asn Glu Cys Glu Gly Lys Pro Cys
        420                 425                 430

Leu Asn Ala Phe Ser Cys Lys Asn Leu Ile Gly Gly Tyr Tyr Cys Asp
    435                 440                 445

Cys Ile Pro Gly Trp Lys Gly Ile Asn Cys His Ile Asn Val Asn Asp
450                 455                 460

Cys Arg Gly Gln Cys Gln His Gly Gly Thr Cys Lys Asp Leu Val Asn
465                 470                 475                 480

Gly Tyr Gln Cys Val Cys Pro Arg Gly Phe Gly Gly Arg His Cys Glu
            485                 490                 495

Leu Glu Arg Asp Glu Cys Ala Ser Ser Pro Cys His Ser Gly Gly Leu
        500                 505                 510

Cys Glu Asp Leu Ala Asp Gly Phe His Cys His Cys Pro Gln Gly Phe
    515                 520                 525

Ser Gly Pro Leu Cys Glu Val Asp Val Asp Leu Cys Glu Pro Ser Pro
530                 535                 540

Cys Arg Asn Gly Ala Arg Cys Tyr Asn Leu Glu Gly Asp Tyr Tyr Cys
545                 550                 555                 560

Ala Cys Pro Asp Asp Phe Gly Gly Lys Asn Cys Ser Val Pro Arg Glu
            565                 570                 575

Pro Cys Pro Gly Gly Ala Cys Arg Val Ile Asp Gly Cys Gly Ser Asp
        580                 585                 590

Ala Gly Pro Gly Met Pro Gly Thr Ala Ala Ser Gly Val Cys Gly Pro
    595                 600                 605

His Gly Arg Cys Val Ser Gln Pro Gly Gly Asn Phe Ser Cys Ile Cys
610                 615                 620

Asp Ser Gly Phe Thr Gly Thr Tyr Cys His Glu Asn Ile Asp Asp Cys
625                 630                 635                 640

Leu Gly Gln Pro Cys Arg Asn Gly Gly Thr Cys Ile Asp Glu Val Asp
```

```
                      645                 650                 655
Ala Phe Arg Cys Phe Cys Pro Ser Gly Trp Glu Gly Glu Leu Cys Asp
                660                 665                 670

Thr Asn Pro Asn Asp Cys Leu Pro Asp Pro Cys His Ser Arg Gly Arg
            675                 680                 685

Cys Tyr Asp Leu Val Asn Asp Phe Tyr Cys Ala Cys Asp Asp Gly Trp
    690                 695                 700

Lys Gly Lys Thr Cys His Ser Arg Glu Phe Gln Cys Asp Ala Tyr Thr
705                 710                 715                 720

Cys Ser Asn Gly Gly Thr Cys Tyr Asp Ser Gly Asp Thr Phe Arg Cys
                725                 730                 735

Ala Cys Pro Pro Gly Trp Lys Gly Ser Thr Cys Ala Val Ala Lys Asn
                740                 745                 750

Ser Ser Cys Leu Pro Asn Pro Cys Val Asn Gly Gly Thr Cys Val Gly
                755                 760                 765

Ser Gly Ala Ser Phe Ser Cys Ile Cys Arg Asp Gly Trp Glu Gly Arg
                770                 775                 780

Thr Cys Thr His Asn Thr Asn Asp Cys Asn Pro Leu Pro Cys Tyr Asn
785                 790                 795                 800

Gly Gly Ile Cys Val Asp Gly Val Asn Trp Phe Arg Cys Glu Cys Ala
                805                 810                 815

Pro Gly Phe Ala Gly Pro Asp Cys Arg Ile Asn Ile Asp Glu Cys Gln
                820                 825                 830

Ser Ser Pro Cys Ala Tyr Gly Ala Thr Cys Val Asp Glu Ile Asn Gly
                835                 840                 845

Tyr Arg Cys Ser Cys Pro Pro Gly Arg Ala Gly Pro Arg Cys Gln Glu
                850                 855                 860

Val Ile Gly Phe Gly Arg Ser Cys Trp Ser Arg Gly Thr Pro Phe Pro
865                 870                 875                 880

His Gly Ser Ser Trp Val Glu Asp Cys Asn Ser Cys Arg Cys Leu Asp
                885                 890                 895

Gly Arg Arg Asp Cys Ser Lys Val Trp Cys Gly Trp Lys Pro Cys Leu
                900                 905                 910

Leu Ala Gly Gln Pro Glu Ala Leu Ser Ala Gln Cys Pro Leu Gly Gln
                915                 920                 925

Arg Cys Leu Glu Lys Ala Pro Gly Gln Cys Leu Arg Pro Pro Cys Glu
                930                 935                 940

Ala Trp Gly Glu Cys Gly Ala Glu Glu Pro Ser Thr Pro Cys Leu
945                 950                 955                 960

Pro Arg Ser Gly His Leu Asp Asn Asn Cys Ala Arg Leu Thr Leu His
                965                 970                 975

Phe Asn Arg Asp His Val Pro Gln Gly Thr Thr Val Gly Ala Ile Cys
                980                 985                 990

Ser Gly Ile Arg Ser Leu Pro Ala  Thr Arg Ala Val Ala  Arg Asp Arg
                995                 1000                1005

Leu Leu  Val Leu Leu Cys Asp  Arg Ala Ser Ser Gly  Ala Ser Ala
    1010                1015                1020

Val Glu  Val Ala Val Ser Phe  Ser Pro Ala Arg Asp  Leu Pro Asp
    1025                1030                1035

Ser Ser  Leu Ile Gln Gly Ala  Ala His Ala Ile Val  Ala Ala Ile
    1040                1045                1050

Thr Gln  Arg Gly Asn Ser Ser  Leu Leu Leu Ala Val  Thr Glu Val
    1055                1060                1065
```

-continued

Lys Val Glu Thr Val Val Thr Gly Gly Ser Ser Thr Gly Leu Leu
1070            1075            1080

Val Pro Val Leu Cys Gly Ala Phe Ser Val Leu Trp Leu Ala Cys
1085            1090            1095

Val Val Leu Cys Val Trp Trp Thr Arg Lys Arg Arg Lys Glu Arg
1100            1105            1110

Glu Arg Ser Arg Leu Pro Arg Glu Glu Ser Ala Asn Asn Gln Trp
1115            1120            1125

Ala Pro Leu Asn Pro Ile Arg Asn Pro Ile Glu Arg Pro Gly Gly
1130            1135            1140

His Lys Asp Val Leu Tyr Gln Cys Lys Asn Phe Thr Pro Pro Pro
1145            1150            1155

Arg Arg Ala Asp Glu Ala Leu Pro Gly Pro Ala Gly His Ala Ala
1160            1165            1170

Val Arg Glu Asp Glu Glu Asp Glu Asp Leu Gly Arg Gly Glu Glu
1175            1180            1185

Asp Ser Leu Glu Ala Glu Lys Phe Leu Ser His Lys Phe Thr Lys
1190            1195            1200

Asp Pro Gly Arg Ser Pro Gly Arg Pro Ala His Trp Ala Ser Gly
1205            1210            1215

Pro Lys Val Asp Asn Arg Ala Val Arg Ser Ile Asn Glu Ala Arg
1220            1225            1230

Tyr Ala Gly Lys Glu
1235

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
ctgaagaacg gggctaacaa                                               20

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
caggttgtac tcgtccagca                                               20

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
ggctccgctg cagacacagg                                               20

<210> SEQ ID NO 11
<211> LENGTH: 20
<212> TYPE: DNA
<213> ORGANISM: Artificial
<220> FEATURE:

<223> OTHER INFORMATION: Primer

<400> SEQUENCE: 11
gctcgccgca agaggcttga                                               20

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
accagtgtga tgagctgtgc                                               20

<210> SEQ ID NO 13
<211> LENGTH: 20
<212> TYPE: DNA
<213> ORGANISM: Artificial
<220> FEATURE:
<223> OTHER INFORMATION: Primer

<400> SEQUENCE: 13
agggtacctt ctgccaggtt                                               20

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
gtgcctccaa cccctgtcgc                                               20

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15
accaacccag cctgcatcgc                                               20

<210> SEQ ID NO 16
<211> LENGTH: 20
<212> TYPE: DNA
<213> ORGANISM: Artificial
<220> FEATURE:
<223> OTHER INFORMATION: Primer

<400> SEQUENCE: 16
gtagagggca tggtggaaga                                               20

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
aagtggtcca acagcagctt                                               20

```
<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
cggagggagc ctgtgggaca                                              20

<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
ggagtcagcg ctgtggctgg                                              20

<210> SEQ ID NO 20
<211> LENGTH: 20
<212> TYPE: DNA
<213> ORGANISM: Artificial
<220> FEATURE:
<223> OTHER INFORMATION: Primer

<400> SEQUENCE: 20
ggcttctact ccgcttcctt                                              20

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21
gatgagctgg aggacgagaa                                              20

<210> SEQ ID NO 22
<211> LENGTH: 21
<212> TYPE: DNA
<213> ORGANISM: Artificial
<220> FEATURE:
<223> OTHER INFORMATION: Primer

<400> SEQUENCE: 22
aagcgacacg tacgagtctg g                                            21

<210> SEQ ID NO 23
<211> LENGTH: 21
<212> TYPE: DNA
<213> ORGANISM: Artificial
<220> FEATURE:
<223> OTHER INFORMATION: Primer

<400> SEQUENCE: 23
atagttgcca gctacttgtg g                                            21

<210> SEQ ID NO 24
<211> LENGTH: 20
<212> TYPE: DNA
<213> ORGANISM: Artificial
<220> FEATURE:
<223> OTHER INFORMATION: Primer
```

-continued

```
<400> SEQUENCE: 24
gcagatgacg gctgcgctga                                              20

<210> SEQ ID NO 25
<211> LENGTH: 22
<212> TYPE: DNA
<213> ORGANISM: Artificial
<220> FEATURE:
<223> OTHER INFORMATION: Primer

<400> SEQUENCE: 25
aagcgggtca cctcgttcat gc                                           22

<210> SEQ ID NO 26
<211> LENGTH: 21
<212> TYPE: DNA
<213> ORGANISM: Artificial
<220> FEATURE:
<223> OTHER INFORMATION: Primer

<400> SEQUENCE: 26
tccaagctag agaaggcaga c                                            21

<210> SEQ ID NO 27
<211> LENGTH: 20
<212> TYPE: DNA
<213> ORGANISM: Artificial
<220> FEATURE:
<223> OTHER INFORMATION: Primer

<400> SEQUENCE: 27
tgatctgggt catgcagttg                                              20

<210> SEQ ID NO 28
<211> LENGTH: 20
<212> TYPE: DNA
<213> ORGANISM: Artificial
<220> FEATURE:
<223> OTHER INFORMATION: Primer

<400> SEQUENCE: 28
aagtttcaca cgagccgttc                                              20

<210> SEQ ID NO 29
<211> LENGTH: 20
<212> TYPE: DNA
<213> ORGANISM: Artificial
<220> FEATURE:
<223> OTHER INFORMATION: Primer

<400> SEQUENCE: 29
gctgttatca gcaccagctc                                              20

<210> SEQ ID NO 30
<211> LENGTH: 20
<212> TYPE: DNA
<213> ORGANISM: Artificial
<220> FEATURE:
<223> OTHER INFORMATION: Primer

<400> SEQUENCE: 30
cgctgttgct ggtgttctaa                                              20

<210> SEQ ID NO 31
<211> LENGTH: 20
```

```
<212> TYPE: DNA
<213> ORGANISM: Artificial
<220> FEATURE:
<223> OTHER INFORMATION: Primer

<400> SEQUENCE: 31
cattgaccac gcagtgtttt                                              20

<210> SEQ ID NO 32
<211> LENGTH: 19
<212> TYPE: DNA
<213> ORGANISM: Artificial
<220> FEATURE:
<223> OTHER INFORMATION: Primer

<400> SEQUENCE: 32
accaactgcg agttcaacg                                               19

<210> SEQ ID NO 33
<211> LENGTH: 19
<212> TYPE: DNA
<213> ORGANISM: Artificial
<220> FEATURE:
<223> OTHER INFORMATION: Primer

<400> SEQUENCE: 33
agcttcacga gctccaggt                                               19

<210> SEQ ID NO 34
<211> LENGTH: 20
<212> TYPE: DNA
<213> ORGANISM: Artificial
<220> FEATURE:
<223> OTHER INFORMATION: Primer

<400> SEQUENCE: 34
ataacggagg ctgggtaggt                                              20

<210> SEQ ID NO 35
<211> LENGTH: 20
<212> TYPE: DNA
<213> ORGANISM: Artificial
<220> FEATURE:
<223> OTHER INFORMATION: Primer

<400> SEQUENCE: 35
cagccaggag aaatcaaaca                                              20

<210> SEQ ID NO 36
<211> LENGTH: 20
<212> TYPE: DNA
<213> ORGANISM: Artificial
<220> FEATURE:
<223> OTHER INFORMATION: Primer

<400> SEQUENCE: 36
tgggatgcct ttgtggaact                                              20

<210> SEQ ID NO 37
<211> LENGTH: 22
<212> TYPE: DNA
<213> ORGANISM: Artificial
<220> FEATURE:
<223> OTHER INFORMATION: Primer

<400> SEQUENCE: 37
```

```
acagccagga gaaatcaaac ag                                    22

<210> SEQ ID NO 38
<211> LENGTH: 20
<212> TYPE: DNA
<213> ORGANISM: Artificial
<220> FEATURE:
<223> OTHER INFORMATION: Primer

<400> SEQUENCE: 38
caacaccagt gtgtgggaac                                       20

<210> SEQ ID NO 39
<211> LENGTH: 20
<212> TYPE: DNA
<213> ORGANISM: Artificial
<220> FEATURE:
<223> OTHER INFORMATION: Primer

<400> SEQUENCE: 39
tcttgtcctg gcaaggtagc                                       20

<210> SEQ ID NO 40
<211> LENGTH: 20
<212> TYPE: DNA
<213> ORGANISM: Artificial
<220> FEATURE:
<223> OTHER INFORMATION: Primer

<400> SEQUENCE: 40
gactgcagtg aagcatccaa                                       20

<210> SEQ ID NO 41
<211> LENGTH: 20
<212> TYPE: DNA
<213> ORGANISM: Artificial
<220> FEATURE:
<223> OTHER INFORMATION: Primer

<400> SEQUENCE: 41
cgtattttgg ggcattcttc                                       20

<210> SEQ ID NO 42
<211> LENGTH: 20
<212> TYPE: DNA
<213> ORGANISM: Artificial
<220> FEATURE:
<223> OTHER INFORMATION: Primer

<400> SEQUENCE: 42
aggacagcct tgggggagac                                       20

<210> SEQ ID NO 43
<211> LENGTH: 21
<212> TYPE: DNA
<213> ORGANISM: Artificial
<220> FEATURE:
<223> OTHER INFORMATION: Primer

<400> SEQUENCE: 43
ctgtcctacc gctacgtggc a                                     21

<210> SEQ ID NO 44
<211> LENGTH: 19
<212> TYPE: DNA
<213> ORGANISM: Artificial
```

```
<220> FEATURE:
<223> OTHER INFORMATION: Primer

<400> SEQUENCE: 44
ccaggttgcc cagtgagaa                                                 19

<210> SEQ ID NO 45
<211> LENGTH: 18
<212> TYPE: DNA
<213> ORGANISM: Artificial
<220> FEATURE:
<223> OTHER INFORMATION: Primer

<400> SEQUENCE: 45
ctcagatggg cgggttca                                                  18

<210> SEQ ID NO 46
<211> LENGTH: 20
<212> TYPE: DNA
<213> ORGANISM: Artificial
<220> FEATURE:
<223> OTHER INFORMATION: Primer

<400> SEQUENCE: 46
atgctgctgt tcagcgggcg                                                20

<210> SEQ ID NO 47
<211> LENGTH: 20
<212> TYPE: DNA
<213> ORGANISM: Artificial
<220> FEATURE:
<223> OTHER INFORMATION: Primer

<400> SEQUENCE: 47
cgggaactca cgcgccagta                                                20

<210> SEQ ID NO 48
<211> LENGTH: 20
<212> TYPE: DNA
<213> ORGANISM: Artificial
<220> FEATURE:
<223> OTHER INFORMATION: Primer

<400> SEQUENCE: 48
cattcgcgtg gataaggagt                                                20

<210> SEQ ID NO 49
<211> LENGTH: 20
<212> TYPE: DNA
<213> ORGANISM: Artificial
<220> FEATURE:
<223> OTHER INFORMATION: Primer

<400> SEQUENCE: 49
tcacacgcca gaagaatttg                                                20

<210> SEQ ID NO 50
<211> LENGTH: 21
<212> TYPE: DNA
<213> ORGANISM: Artificial
<220> FEATURE:
<223> OTHER INFORMATION: Primer

<400> SEQUENCE: 50
tgggagcatc ggctactgct g                                              21
```

<210> SEQ ID NO 51
<211> LENGTH: 21
<212> TYPE: DNA
<213> ORGANISM: Artificial
<220> FEATURE:
<223> OTHER INFORMATION: Primer

<400> SEQUENCE: 51
tgctctcaca tggggactgg g                                    21

<210> SEQ ID NO 52
<211> LENGTH: 21
<212> TYPE: DNA
<213> ORGANISM: Artificial
<220> FEATURE:
<223> OTHER INFORMATION: Primer

<400> SEQUENCE: 52
ccaacgcgac ctcatctcta a                                    21

<210> SEQ ID NO 53
<211> LENGTH: 17
<212> TYPE: DNA
<213> ORGANISM: Artificial
<220> FEATURE:
<223> OTHER INFORMATION: Primer

<400> SEQUENCE: 53
agggcggttg cccagta                                         17

<210> SEQ ID NO 54
<211> LENGTH: 20
<212> TYPE: DNA
<213> ORGANISM: Artificial
<220> FEATURE:
<223> OTHER INFORMATION: Primer

<400> SEQUENCE: 54
tgcgccagct gaggtgtgag                                      20

<210> SEQ ID NO 55
<211> LENGTH: 20
<212> TYPE: DNA
<213> ORGANISM: Artificial
<220> FEATURE:
<223> OTHER INFORMATION: Primer

<400> SEQUENCE: 55
tcgctgtcca ctgggccgaa                                      20

<210> SEQ ID NO 56
<211> LENGTH: 20
<212> TYPE: DNA
<213> ORGANISM: Artificial
<220> FEATURE:
<223> OTHER INFORMATION: Primer

<400> SEQUENCE: 56
cttttgcgtc gccagccgag                                      20

<210> SEQ ID NO 57
<211> LENGTH: 20
<212> TYPE: DNA
<213> ORGANISM: Artificial
<220> FEATURE:
<223> OTHER INFORMATION: Primer

```
<400> SEQUENCE: 57
ccaggcgccc aatacgacca                                               20

<210> SEQ ID NO 58
<211> LENGTH: 20
<212> TYPE: DNA
<213> ORGANISM: Artificial
<220> FEATURE:
<223> OTHER INFORMATION: Primer

<400> SEQUENCE: 58
tggtgaaggt cggtgtgaac                                               20

<210> SEQ ID NO 59
<211> LENGTH: 24
<212> TYPE: DNA
<213> ORGANISM: Artificial
<220> FEATURE:
<223> OTHER INFORMATION: Primer

<400> SEQUENCE: 59
ccatgtagtt gaggtcaatg aagg                                          24
```